/

US008287851B2

(12) United States Patent
Wright et al.

(10) Patent No.: US 8,287,851 B2
(45) Date of Patent: Oct. 16, 2012

(54) USE OF INTERLEUKIN 17E FOR THE TREATMENT OF CANCER

(75) Inventors: Jim A. Wright, Oakville (CA); Aiping H. Young, North York (CA); Yoon Lee, Mississauga (CA); Ming Yu Cao, Mississauga (CA)

(73) Assignee: Lorus Therapeutics Inc., Toronto (CA)

( * ) Notice: Subject to any disclaimer, the term of this patent is extended or adjusted under 35 U.S.C. 154(b) by 994 days.

(21) Appl. No.: 11/817,914

(22) PCT Filed: Mar. 8, 2006

(86) PCT No.: PCT/CA2006/000311
§ 371 (c)(1),
(2), (4) Date: Sep. 17, 2008

(87) PCT Pub. No.: WO2006/094384
PCT Pub. Date: Sep. 14, 2006

(65) Prior Publication Data
US 2011/0158936 A1 Jun. 30, 2011

Related U.S. Application Data

(60) Provisional application No. 60/659,857, filed on Mar. 8, 2005, provisional application No. 60/713,335, filed on Sep. 2, 2005.

(51) Int. Cl.
*A61K 38/20* (2006.01)
(52) U.S. Cl. ........................................ 424/85.2; 530/351
(58) Field of Classification Search .................... None
See application file for complete search history.

(56) References Cited

U.S. PATENT DOCUMENTS

| | | | |
|---|---|---|---|
| 6,280,774 B1 | 8/2001 | Rang | |
| 6,569,645 B2 | 5/2003 | Chen | |
| 6,579,520 B2 * | 6/2003 | Chen et al. ................... | 424/85.2 |
| 6,596,319 B2 | 7/2003 | Rang | |
| 2002/0037524 A1 | 3/2002 | Medlock | |
| 2002/0177188 A1 | 11/2002 | Chen | |
| 2002/0182672 A1 | 12/2002 | Kolkman | |
| 2002/0182673 A1 | 12/2002 | Chen | |
| 2003/0003546 A1 | 1/2003 | Chen | |
| 2003/0008815 A1 | 1/2003 | Chen | |
| 2003/0054442 A1 | 3/2003 | Chen | |
| 2003/0124092 A1 | 7/2003 | Medlock | |
| 2003/0180255 A1 | 9/2003 | Goddard | |
| 2003/0186306 A1 | 10/2003 | Goddard | |
| 2003/0199044 A1 | 10/2003 | Goddard | |
| 2003/0203451 A1 | 10/2003 | Chen | |
| 2004/0043397 A1 | 3/2004 | Chen | |
| 2004/0091503 A1 | 5/2004 | Segal | |
| 2004/0106184 A1 | 6/2004 | Senesac | |
| 2004/0122217 A1 | 6/2004 | Segal | |
| 2004/0126357 A1 | 7/2004 | Segal | |
| 2004/0126793 A1 | 7/2004 | Segal | |
| 2004/0136963 A1 | 7/2004 | Wilson | |
| 2004/0142889 A1 | 7/2004 | Segal | |
| 2004/0151728 A1 | 8/2004 | Segal | |
| 2004/0170960 A1 | 9/2004 | Segal | |
| 2004/0180389 A1 | 9/2004 | Segal | |
| 2004/0241137 A1 | 12/2004 | Segal | |
| 2005/0003451 A1 | 1/2005 | Medlock | |
| 2005/0048029 A1 | 3/2005 | Medlock | |
| 2005/0064391 A1 | 3/2005 | Segal | |
| 2005/0069866 A1 | 3/2005 | Wilson | |
| 2005/0074427 A1 | 4/2005 | Medlock | |

FOREIGN PATENT DOCUMENTS

| | | |
|---|---|---|
| WO | WO 95/07089 A1 | 3/1995 |
| WO | WO 96/28175 A1 | 9/1996 |
| WO | WO 02/38164 A1 | 5/2002 |

OTHER PUBLICATIONS

Activated Eosinophils Infiltrate MCF-7 Breast Multicellular Tumor Spheroids, Paulette M. Furbert-Harris, Ibrahim Laniyan, Dana Harris, Georgia M. Dunston, Theresa Vaughn, Abier Abdelnaby, Debra Parish-Gause and Oladipo A. Oredipe; Anti-Cancer Research 23: pp. 71-78 (2003).
Inhibition of Prostate Cancer Cell Growth by Activated Eosinophils, Paulette M. Furbert-Harris, Debra ParishGause, Ibrahim Laniyan, Keith A. Hunter, Josephine Okomo-Awich, Theresa Vaughn, Kesha C. Forrest, Christina Howland, Abier Abdelnaby, and Oladipo A. Oredipe; The Prostate, 57: pp. 165-175 (2003).
Transgenic overexpression of human IL-17E results in eosinophilia, B-lymphocyte hyperplasia, and altered antibody production, Mee Rhan Kim, Raffi Manoukian, Richard Yeh, Scott M. Silbiger, Dimitry M. Danilenko, Sheila Scully, Jiin Sun, Margaret L. DeRose, Marina Stolina, David Chang, Gwyneth Y. Van, Kristie Clarkin, Hung Q. Nguyen, Yan Bin Yu, Shuclian Jing, Giorgio Senakti, Gary Elliott and Eugene S. Medlock; Blood, vol. 100, No. 7, pp. 2330-2340. Oct. 1, 2002.
IL-25 Induces IL-4, IL-5, and IL-13 and Th2-Associated Pathologies In Vivo, Madeline M. Fort, Heanne Cheung, David Yen, Joana Li, Sandra M. Zurawski, Sylvia Lo, Satish Menon, Teresa Clifford, Brisdell Hunte, Robin Lesley, Tony Muchamuel, Stephen D. Hurst, Gerard Zurawski, Michael W. Leach, Daniel M. Gorman, and Donna M. Rennick; Immunity. vol. 15, pp. 985-995, Dec. 2001.
GenBank Accession No. AAG40848 "Interleukin 17E [*Homo sapiens*]" dated Jan. 9, 2001.
GenBank Accession No. AAL57622 "IL25 [*Homo sapiens*]" dated Jan. 15, 2002.
GenBank Accession No. AAL57623 IL25 [*Mus musculus*] dated Jan. 15, 2002.
GenBank Accession No. AAN39038 "Interleukin 17E [*Homo sapiens*]" Oct. 9, 2002.
GenBank Accession No. AF305200 "*Homo sapiens* interleukin 17E (IL17E) mRNA, complete cds" dated Jan. 9, 2001.
GenBank Accession No. AF458059 "*Homo sapiens* IL25 mRNA, complete cds" Jan. 15, 2002.

(Continued)

*Primary Examiner* — Dong Jiang
(74) *Attorney, Agent, or Firm* — Carol L. Francis; Bozicevic, Field & Francis LLP

(57) ABSTRACT

The use of interleukin 17E to inhibit tumor growth in a subject is provided. The interleukin 17E can be provided to the subject exogenously, as an interleukin 17E polypeptide or a polynucleotide encoding an interleukin 17E polypeptide, or it can be provided by stimulating production of endogenous interleukin 17E. Also provided is the use of interleukin 17E in combination with one or more anti-cancer therapeutics for inhibiting tumor growth in a subject. Anti-cancer therapeutics include, for example, standard chemotherapeutic drugs, immunotherapeutics, radiation, gene therapy, hormone manipulation and antisense therapy.

31 Claims, 44 Drawing Sheets

OTHER PUBLICATIONS

GenBank Accession No. AF458060 "*Mus musculus* IL25 mRNA, complete cds" dated Jan. 15, 2002.
GenBank Accession No. AF461739 "*Homo sapiens* interleukin 17E (IL17E) mRNA, complete cds" dated Oct. 9, 2002.
GenBank Accession No. NM_022789 "*Homo sapiens* interleukin 25 (IL25), transcript variant 1, mRNA" dated May 22, 2011.
GenBank Accession No. NM_080729 "*Mus musculus* interleukin 25 (Il25), mRNA" dated Dec. 24, 2011.
GenBank Accession No. NM_172314 "*Homo sapiens* interleukin 25 (IL25), transcript variant 2, mRNA" dated May 22, 2011.
GenBank Accession No. NP.073626 "Interleukin-25 isoform 1 precursor [*Homo sapiens*]" dated May 22, 2011.
GenBank Accession No. NP_542767 "Interleukin-25 [*Mus musculus*]" dated Jul. 24, 2011.
GenBank Accession No. NP_758525 "Interleukin-25 isoform 2 precursor [*Homo sapiens*]" dated May 22, 2011.
GenBank Accession No. Q9H293 "RecName: Full=Interleukin-25; Short=IL-25; AltName: Full=Interleukin-17E; Short=IL-17E; Flags: Precursor" dated Jan. 25, 2012.
Aggarwal, S., et al. "IL-17: prototype member of an emerging cytokine family". Journal of Leukocyte Biology, Jan. 2002, vol. 71, pp. 1-8.
Axdorph U, Porwit-MacDonald A, Grimfors G, Bjorkholm M. Tissue eosinophilia in relation to immunopathological and clinical characteristics in Hodgkin's disease. Leuk Lymphoma. 2001.42:1055-65.
Cao, M., et al. "NK cell activation and tumor infiltration are involved in the antitumor mechanism of Virulizin". Cancer Immunol Immunother, Epub Sep. 2004, vol. 54, pp. 229-242.
Critchley RJ, Jezzard S, Radford KJ, Goussard S, Lemoine NR, Grillot-Courvalin C, Vassaux G. Potential therapeutic applications of recombinant, invasive *E. coli*. Gene Ther. 2004. 11:1224-33.
Dorta RG, Landman G, Kowalski LP, Lauris JR, Latorre MR, Oliveira DT. Tumour-associated tissue eosinophilia as a prognostic factor in oral squamous cell carcinomas. Histopathology. 2002. 41:152-7.
Ferdinandi, E., et al. "Virulizin®—a review of its antineoplastic activity". Expert Opinion on Investigational Drugs, 1999, vol. 8, pp. 1721-1735.
Fernandez-Acenero MJ, Galindo-Gallego M, Sanz J, Aljama A. Prognostic influence of tumor-associated eosinophilic infiltrate in colorectal carcinoma. Cancer. 88(7):1544-8, 2000.
Grillot-Courvalin C, Goussard S, Huetz F, Ojcius DM, Courvalin P. Functional gene transfer from intracellular bacteria to mammalian cells. Nat Biotechnol. 1998. 16:862-6.
Hanamoto H, Nakayama T, Miyazato H, Takegawa S, Hieshima K, Tatsumi Y, Kanamaru A, Yoshie O. Expression of CCL28 by Reed-Sternberg cells defines a major subtype of classical Hodgkin's disease with frequent infiltration of eosinophils and/or plasma cells. Am J Pathol. 2004. 164:997-1006.
Hogan, S. "Recent Advances in Eosinophil Biology". International Archives of Allergy & Immunology, published online May 2007, vol. 143 (suppl 1), pp. 3-14.
Horiuchi K, Mishima K, Ohsawa M, Sugimura M, Aozasa K. Prognostic factors for well-differentiated squamous cell carcinoma in the oral cavity with emphasis on immunohistochemical evaluation. J Surg Oncol. 1993. 53:92-6.
Hurst, S., et al. "New IL-17 Family Members Promote Th1 or Th2 Responses in the Lung: In Vivo Function of the Novel Cytikine IL-251". The Journal of Immunology, Apr. 2002, vol. 169, pp. 443-453.
Ikeda, K., et al. "Mast cells produce interleukin-25 upon FœRI-mediated activation". Blood, May 2003, vol. 101, pp. 3594-3596.
Kang, C., et al. "Interleukin-25 and Interleukin-13 Production by Alveolar Macrophages in Response to Particles". American Journal of Respiratory Cell and Molecular Biology, Jun. 2005, vol. 33, pp. 290-296.
Kolls, J., et al. "Interleukin-17 Family Members and Inflammation". Immunity, Oct. 2004, vol. 21, pp. 467-476.
Kaminsky RG et al., Intestinal parasitic infections and eosinophilia in an human immunedeficiency virus positive population in Honduras. Mem Inst. Oswaldo Cruz. 2004 99:773-8.
Lee, J., et al. "Il-17E, a Novel Proinflammatory Ligand for the IL-17 Receptor Homolog IL-17Rh1*". The Journal of Biological Chemistry, Jan. 2001, vol. 276, No. 2, pp. 1660-1664.
Liu, C., et al. "Virulizin®-2γ. Biological response modifier treatment of pancreatic cancer". Drugs of the Future, 2000, vol. 25, pp. 356-359.
Lowe DG. Carcinoma of the cervix with massive eosinophilia. Br J Obstet Gynaecol. 1988. 95:393-401.
Ohashi Y, Ishibashi S, Suzuki T, Shineha R, Moriya T, Satomi S, Sasano H. Significance of tumor associated tissue eosinophilia and other inflammatory cell infiltrate in early esophageal squamous cell carcinoma. Anticancer Res. 2000. 20:3025-30.
Pan, G., et al. "Forced Expression of Murine IL-17E Induces Growth Retardation, Jaundice, a Th2-Biased Response, and Multiorgan Inflammation in Mice". The Journal of Immunology, 2001, vol. 167, pp. 6559-6567.
Pretlow TP, Keith EF, Cryar AK, Bartolucci AA, Pitts AM, Pretlow TG 2nd, Kimball PM, Boohaker EA. Eosinophil infiltration of human colonic carcinomas as a prognostic indicator. Cancer Res. 1983. 43:2997-3000.
Pitman MB, Young RH, Clement PB, Dickersin GR, Scully RE. Endometrioid carcinoma of the ovary and endometrium, oxyphilic cell type: a report of nine cases. Int J Gynecol Pathol. 1994. 13:290-301.
Romano F, Cesana G, Berselli M, Gaia Piacentini M, Caprotti R, Bovo G, Uggeri F. Biological, histological, and clinical impact of preoperative IL-2 administration in radically operable gastric cancer patients. J Surg Oncol. 2004a. 88:240-7.
Romano F, Piacentini Mg, Franciosi C, Caprotti R, De Fina S, Cesana G, Uggeri F, Conti M, Uggeri F. Phase-II randomized study of preoperative IL-2 administration in radically operable gastric cancer patients. Hepatogastroenterology. 2004b, 51:1872-6.
Suckow, MA et al., "Prevention of de novo prostate cancer by immunization with tumor-derived vaccines". Cancer Immunol Immunother. 54: 571-576, 2005.
Takanami I, Takeuchi K, Gika M. Immunohistochemical detection of eosinophilic infiltration in pulmonary adenocarcinoma. Anticancer Res. 2002. 22:2391-6.
Tani K, et al., Phase 1 Study of Autologous Tumor Vaccines Transduced with the GM-CSF gene in four patients with stage IV renal cell cancer in Japan: clinical and immunological findings. Mol Ther. 2004 10:799-816.
Lorus Therapeutics Inc., Virulizin Publication "We see hope in more directions. Immunotherapy. Antisense. Small Molecule. Gene Therapy." dated May 14, 2005.
Wong, D.T.W., et al. "Eosinophil ablation and tumor development". Oral Oncology, 1999, vol. 35, pp. 496-501.
Yamamoto T, Yokoyama A. Eosinophil infiltration in the sclerodermoid cutaneous metastasis of a breast cancer. J Dermatol. 2000. 27:552-3.
Press Release: "Lorus Describes Virulizin's Ability to Induce a Novel Cytokine IL-17E to Enhance Antitumor Activity" dated Mar. 9, 2005.
Benatar, et al. "Virulizin induces production of IL-17E to enhance antitumor activity by recruitment of eosinophils into tumors" Research & Development Department, Lorus Therapeutics Inc., May 13, 2005.
Press Release: "Lorus presents at American Society of Clinical Oncology Today" dated May 15, 2005.
Cao, et al. "IL-17E, a proinflammatory cytokine, has a novel anticancer function in vivo" Research & Development Department, Lorus Therapeutics Inc., Apr. 1, 2006.
Press Release: "Lorus Announces presentation of Anticancer Drug Platforms at the 2006 meeting of the American Association for Cancer Research (AACR)" Abstract for AACR meeting, Apr. 3, 2006.

* cited by examiner

>gi|18141561|ref|NP_542767.1| interleukin 17E [Mus musculus]

MYQAVAFLAMIVGTHTVSLRIQEGCSHLPSCCPSKEQEPPEEWLKWSSASVSP
PEPLSHTHHAESCRASKDGPLNSRAISPWSYELDRDLNRVPQDLYHARCLCPH
CVSLQTGSHMDPLGNSVPLYHNQTVFYRRPCHGE
EGTHRRYCLERRLYRVSLACVCVRPRVMA

FIGURE 32 gi|20138730|sp|Q9H293|IL17E_HUMAN Interleukin-17E precursor (IL-17E) (Interleukin-25) (IL-25)

MRERPRLGEDSSLISLFLQVVAFLAMVMGTHTYSHWPSCCPSKGQDTSEELL
RWSTVPVPPLEPARPNRHPESCRASEDGPLNSRAISPWRYELDRDLNRLPQDL
YHARCLCPHCVSLQTGSHMDPRGNSELLYHNQTVFYRRPCHGEKGTHKGYC
LERRLYRVSLACVCVRPRVMG

FIGURE 33

>gi|23600388|gb|AAN39038.1|AF461739_1 interleukin 17E [Homo sapiens]

MYQVVAFLAMVMGTHTYSHWPSCCPSKGQDTSEELLRWSTVPVPPLEPARP
NRHPESCRASEDGPLNSRAISPWRYELDRDLNRLPQDLYHARCLCPHCVSLQT
GSHMDPRGNSELLYHNQTVFYRRPCHGEKGTHKGYCLERRLYRVSLACVCV
RPRVMG

FIGURE 34

>gi|18034676|gb|AAL57622.1|AF458059_1 IL25 [Homo sapiens]

MYQVVAFLAMVMGTHTYSHWPSCCPSKGQDTSEELLRWSTVPVPPLEPARP
NRHPESCRASEDGPLNSRAISPWRYELDRDLNRLPQDLYHARCLCPHCVSLQT
GSHMDPRGNSELLYHNQTVFYRRPCHGEKGTHKGYCLERRLYRVSLACVCV
RPRVMA

FIGURE 35

>gi|18141560|ref|NM_080729.1| Mus musculus interleukin 17E (Il17e), mRNA
ATGTACCAGGCTGTTGCATTCTTGGCAATGATCGTGGGAACCCACACCGTC
AGCTTGCGGATCCAGGAGGGCTGCAGTCACTTGCCCAGCTGCTGCCCCAG
CAAAGAGCAAGAACCCCCGGAGGAGTGGCTGAAGTGGAGCTCTGCATCT
GTGTCCCCCCAGAGCCTCTGAGCCACACCCACCACGCAGAATCCTGCAG
GGCCAGCAAGGATGGCCCCCTCAACAGCAGGGCCATCTCTCCTTGGAGCT
ATGAGTTGGACAGGGACTTGAATCGGGTCCCCCAGGACCTGTACCACGCT
CGATGCCTGTGCCCACACTGCGTCAGCCTACAGACAGGCTCCCACATGGA
CCCGCTGGGCAACTCCGTCCCACTTTACCACAACCAGACGGTCTTCTACCG
GCGGCCATGCCATGGTGAGGAAGGTACCCATCGCCGCTACTGCTTGGAGC
GCAGGCTCTACCGAGTCTCCTTGGCTTGTGTGTGTGCGGCCCCGGGTCA
TGGCTTAGTCATGCTCACCACCTGCCTGAGGCTGATGCCCGGTTGGGAGA
GAGGGCCAGGTGTACAATCACCTTGCCAATGCGGGCCGGGTTCAAGCCCT
CCAAAGCCCTACCTGAAGCAGCAGGCTCCCGGGACAAGATGGAGGACTTG
GGGAGAAACTCTGACTTTTGCACTTTTTGGAAGCACTTTTGGGAAGGAGC
AGGTTCCGCTTGTGCTGCTAGAGGATGCTGTTGTGGCATTTCTACTCAGGA
ACGGACTCCAAAGGCCTGCTGACCCTGGAAGCCATACTCCTGGCTCCTTTC
CCCTGAATCCCCCAACTCCTGGCACAGGCACTTTCTCCACCTCTCCCCCTT
TGCCTTTTGTTGTGTTTGTTTGTGCATGCCAACTCTGCGTGCAGCCAGGTGT
AATTGCCTTGAAGGATGGTTCTGAGGTGAAAGCTGTTATCGAAAGTGAAG
AGATTTATCCAAATAAACATCTGTGTTT

FIGURE 36

>gi|11878209|gb|AF305200.1|AF305200 Homo sapiens interleukin 17E (IL17E) mRNA, complete cds
GGCTTGCTGAAAATAAAATCAGGACTCCTAACCTGCTCCAGTCAGCCTGC
TTCCACGAGGCCTGTCAGTCAGTGCCCGACTTGTGACTGAGTGTGCAGTGC
CCAGCATGTACCAGGTCAGTGCAGAGGGCTGCCTGAGGGCTGTGCTGAGA
GGGAGAGGAGCAGAGATGCTGCTGAGGGTGGAGGGAGGCCAAGCTGCCA
GGTTTGGGGCTGGGGGCCAAGTGGAGTGAGAAACTGGGATCCCAGGGGG
AGGGTGCAGATGAGGGAGCGACCCAGATTAGGTGAGGACAGTTCTCTCAT
TAGCCTTTTCCTACAGGTGGTTGCATTCTTGGCAATGGTCATGGGAACCCA
CACCTACAGCCACTGGCCCAGCTGCTGCCCCAGCAAAGGGCAGGACACCT
CTGAGGAGCTGCTGAGGTGGAGCACTGTGCCTGTGCCTCCCCTAGAGCCT
GCTAGGCCCAACCGCCACCCAGAGTCCTGTAGGGCCAGTGAAGATGGACC
CCTCAACAGCAGGGCCATCTCCCCCTGGAGATATGAGTTGGACAGAGACT
TGAACCGGCTCCCCCAGGACCTGTACCACGCCCGTTGCCTGTGCCCGCACT
GCGTCAGCCTACAGACAGGCTCCCACATGGACCCCCGGGGCAACTCGGAG
CTGCTCTACCACAACCAGACTGTCTTCTACAGGCGGCCATGCCATGGCGA
GAAGGGCACCCACAAGGGCTACTGCCTGGAGCGCAGGCTGTACCGTGTTT
CCTTAGCTTGTGTGTGTGTGCGGCCCCGTGTGATGGGCTAGCCGGACCTGC
TGGAGGCTGGTCCCTTTTGGGAAACCTGGAGCCAGGTGTACAACCACTT
GCCATGAAGGGCCAGGATGCCCAGATGCTTGGCCCCTGTGAAGTGCTGTC
TGGAGCAGCAGGATCCCGGGACAGGATGGGGGGCTTTGGGGAAAACCTG
CACTTCTGCACATTTTGAAAAGAGCAGCTGCTGCTTAGGGCCGCCGGAAG
CTGGTGTCCTGTCATTTCTCTCAGGAAAGGTTTTCAAAGTTCTGCCCATTT
CTGGAGGCCACCACTCCTGTCTCTTCCTCTTTTCCCATCCCCTGCTACCCTG
GCCCAGCACAGGCACTTTCTAGATATTTCCCCCTTGCTGGAGAAGAAAGA
GCCCCTGGTTTTATTTGTTTGTTTACTCATCACTCAGTGAGCATCTACTTTG
GGTGCATTCTAGTGTAGTTACTAGTCTTTGACATGGATGATTCTGAGGAG
GAAGCTGTTATTGAATGTATAGAGATTTATCCAAATAAATATCTTTATTTA
AAAATGAAAAAAAAAAAAAAAAAAAA

FIGURE 37

>gi|23600387|gb|AF461739.1| Homo sapiens interleukin 17E (IL17E) mRNA, complete cds
CTCAAGTCACTCCCTAAAAAGACAGTGGAAATAAATTTGAATAAACAAAA
CAGGCTTGCTGAAAATAAAATCAGGACTCCTAACCTGCTCCAGTCAGCCT
GCTTCCACGAGGCCTGTCAGTCAGTGCCCCACTTGTGACTGAGTGTGCAGT
GCCCAGCATGTACCAGGTGGTTGCATTCTTGGCAATGGTCATGGGAACCC
ACACCTACAGCCACTGGCCCAGCTGCTGCCCCAGCAAAGGGCAGGACACC
TCTGAGGAGCTGCTGAGGTGGAGCACTGTGCCTGTGCCTCCCCTAGAGCC
TGCTAGGCCCAACCGCCACCCAGAGTCCTGTAGGGCCAGTGAAGATGGAC
CCCTCAACAGCAGGGCCATCTCCCCCTGGAGATATGAGTTGGACAGAGAC
TTGAACCGGCTCCCCCAGGACCTGTACCACGCCCGTTGCCTGTGCCCGCAC
TGCGTCAGCCTACAGACAGGCTCCCACATGGACCCCCGGGGCAACTCGGA
GCTGCTCTACCACAACCAGACTGTCTTCTACCGGCGGCCATGCCATGGCG
AGAAGGGCACCCACAAGGGCTACTGCCTGGAGCGCAGGCTGTACCGTGTT
TCCTTAGCTTGTGTGTGTGTGCGGCCC GTGTGATGGGCTAG

FIGURE 38

>gi|18034675|gb|AF458059.1|AF458059 Homo sapiens IL25 mRNA, complete cds
ATGTACCAGGTGGTTGCATTCTTGGCAATGGTCATGGGAACCCACACCTA
CAGCCACTGGCCCAGCTGCTGCCCCAGCAAAGGGCAGGACACCTCTGAGG
AGCTGCTGAGGTGGAGCACTGTGCCTGTGCCTCCCCTAGAGCCTGCTAGG
CCCAACCGCCACCCAGAGTCCTGTAGGGCCAGTGAAGATGGACCCCTCAA
CAGCAGGGCCATCTCCCCCTGGAGATATGAGTTGGACAGAGACTTGAACC
GGCTCCCCCAGGACCTGTACCACGCCCGTTGCCTGTGCCCGCACTGCGTCA
GCCTACAGACAGGCTCCCACATGGACCCCGGGGCAACTCGGAGCTGCTC
TACCACAACCAGACTGTCTTCTACCGGCGGCCATGCCATGGCGAGAAGGG
CACCCACAAGGGCTACTGCCTGGAGCGCAGGCTGTACCGTGTTTCCTTGG
CTTGTGTGTGTGTGCGGCCCCGGGTCATGGCTTAG

USE OF INTERLEUKIN 17E FOR THE TREATMENT OF CANCER

CROSS-REFERENCE TO RELATED APPLICATIONS

This is a National Phase Filing Under 35 U.S.C. 371, of International Application No. PCT/CA06/000311, filed Mar. 8, 2006, which claims the benefit of priority of U.S. Provisional Patent Application Ser. No. 60/659,857 filed Mar. 8, 2005, and U.S. Provisional Patent Application Ser. No. 60/713,335 filed Sep. 2, 2005, all of which are incorporated herein by reference.

FIELD OF THE INVENTION

The present invention relates to the field of cancer therapeutics and in particular to the use of interleukin 17E for the treatment of cancer.

BACKGROUND OF THE INVENTION

Cytokines are a large family of more than 160 soluble intercellular signaling proteins involved in the regulation of the immune system. IL-17E (IL-25) belongs to a family of cytokines which possess homology to IL-17 (Aggarwal et al., (2002) *J. Leukoc Biol* 71: 1-8; and Hurst et al., (2002) *J Immunol* 169: 443-453). The interleukin 17 family of cytokines share a conserved cysteine-knot fold near the C-terminus. All interleukin 17 family members, except interleukin 17B, are disulfide-linked dimers. Interleukin 17E proteins from a variety of species share significant amino acid sequence identity. For example, mature human interleukin 17E shares 76% identity with mature mouse interleukin 17E. Various isoforms of human interleukin 17E which share significant homology have been identified (Kim et al., (2002) *Blood* 100: 2330-2340; Lee et al. (2001) *J. Biol. Chem.* 276: 1660-1664 and Fort et al. (2001) *Immunity* 15:985-995).

Although IL-17E is structurally related to IL-17, its biological effects differ dramatically from those described for IL-17 and other IL-17 family cytokines. The expression of IL-17E in mice results in the expansion of eosinophils through the production of IL-5 from an unidentified non-T-cell population (Hurst et al., (2002) *J Immunol* 169: 443-453; Pan et al., (2001) *J Immunol* 167: 6559-6567; and Fort et al., (2001) *Immunity* 15: 985-995). In addition, IL-17E induces elevated gene expression of IL-4 and IL-13 in multiple tissues and the resultant T helper 2 ($T_H2$)-type immune response which manifests as increased serum immunoglobulin E (IgE) levels and pathological changes in the lungs and digestive tract with eosinophilic infiltrates, increased mucus production, and epithelial cell hyperplasia (Hurst et al., (2002) *J Immunol* 169: 443-453; Pan et al., (2001) *J Immunol* 167: 6559-6567; and Fort et al., (2001) *Immunity* 15: 985-995), indicating that IL-17E is capable of amplifying inflammatory responses.

Although IL-17E mRNA was shown to be expressed in polarized $T_H2$ cells (Fort et al., (2001) *Immunity* 15: 985-995), IL-17E mRNA was also detected in multiple tissues, including colon, uterus, stomach, small intestine, kidney and lung (Hurst et al., (2002) *J Immunol* 169: 443-453; Pan et al., (2001) *J Immunol* 167: 6559-6567; and Fort et al., (2001) *Immunity* 15: 985-995), suggesting that in addition to $T_H2$ cells, other cell types may produce IL-17E. Bone marrow-derived mast cells are also capable of producing IL-17E upon IgE crosslinking, therefore, mast cell-derived IL-17E may be involved in the augmentation of $T_H2$-type immune responses (Ikeda et al., (2003) *Blood* 101: 1341-1346).

The identification of polypeptides having sequence similarity to interleukin-17, including two isoforms of IL-17E, and their therapeutic use has been described. For example, U.S. Pat. Nos. 6,579,520, and 6,569,645, and U.S. patent Application Nos. 20040043397; 20030203451; 20030199044; 20030186306; 20030180255; 20030054442; 20030008815; 20030003546; 20020182673 and 20020177188 describe a family of polypeptides, including interleukin 17E, which have sequence identity with interleukin 17, as well as interleukin 17 receptors and the nucleic acid molecules encoding these polypeptides. The family of polypeptides are shown to stimulate T-cell proliferation/activation and it is, therefore, speculated that they may be useful as adjuvants to stimulate T cell proliferation/activation to tumour antigens and thereby promote an anti-tumour response. No experimental data, however, is provided to demonstrate the immunoadjuvant effect of these polypeptides.

In direct contrast to the teaching in above-noted patents and patent applications, U.S. Patent Application Nos. 20050074427; 20050048029; 20050003451; 20030124092; 20020037524 describe a potential role for interleukin 17-like polypeptides in progression of cancers such as lymphoma and suggest the use of antagonists to the interleukin 17-like polypeptides for the treatment of cancerous or lymphoma conditions.

U.S. Patent Application Nos. 20050064391; 20040241137; 20040126357; 20040091503; 20040180389; 20040151728; 20040170960; 20040142889; 20040126793 and 20040122217 describe lectin compositions and methods of using same for modulating an immune response to an antigen. The compositions comprise an antigen bearing target and a fusion polypeptide that comprises a first part which is capable of binding to a carbohydrate and a second part which is capable of binding to a cell. The second part of the fusion polypeptide is a ligand, such as a ligand for a cytokine receptor, CD40, an adhesion molecule, a defensin receptor, a heat shock protein receptor, a T cell costimulatory molecule, or a counterreceptor for a T cell costimulatory molecule. Exemplary ligands for cytokine receptors described in these applications include various interleukins, amongst which IL-25 is contemplated as an option. While the methods described in the applications include methods of modulating an immune response, treating a disease or reducing the number of metastases in a subject, these patent applications do not provide any experimental data demonstrating the anti-tumour activity of the described compositions.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a use of interleukin 17E for the treatment of cancer. In accordance with an aspect of the present invention, there is provided a pharmaceutical composition for inhibiting tumour growth in a subject, said pharmaceutical composition comprising an effective amount of an interleukin 17E (IL-17E) polypeptide or a polynucleotide encoding an IL-17E polypeptide and a pharmaceutically acceptable carrier, wherein said IL-17E polypeptide is provided in an amount effective to inhibit tumour growth.

In accordance with, another aspect of the present invention, there is provided a combination product for inhibiting tumour growth in a subject, said combination product comprising an effective amount of an interleukin 17E (IL-17E) polypeptide or a polynucleotide encoding an IL-17E polypeptide and one or more anticancer therapeutics, wherein said IL-17E polypeptide is provided in an amount effective to inhibit tumour growth.

In accordance with another aspect of the present invention, there is provided a use of an interleukin 17E (IL-17E) polypeptide or a polynucleotide encoding an IL-17E polypeptide to inhibit tumour growth in a subject.

In accordance with another aspect of the present invention, there is provided a use of an interleukin 17E (IL-17E) polypeptide or a polynucleotide encoding an IL-17E polypeptide in combination with one or more anticancer therapeutics to inhibit tumour growth in a subject.

In accordance with another aspect of the present invention, there is provided a use of an interleukin 17E (IL-17E) polypeptide or a polynucleotide encoding an IL-17E polypeptide in the manufacture of a medicament for inhibition of tumour growth.

In accordance with another aspect of the present invention, there is provided a method of inhibiting tumour growth in a subject by increasing the levels of an interleukin 17E (IL-17E) polypeptide in said subject.

In accordance with another aspect of the present invention, there is provided a method of inhibiting tumour growth in a subject by increasing the levels of an interleukin 17E (IL-17E) polypeptide in said subject in combination with administering one or more anti-cancer therapeutics to said subject.

BRIEF DESCRIPTION OF THE DRAWINGS

These and other features of the invention will become more apparent in the following detailed description in which reference is made to the appended drawings.

FIG. 29A), IL17BR (FIG. 29B) and total Lyn protein (FIG. 29C). Molecular weight markers in kilodaltons (kD) are shown.

FIG. 31 provides the sequence for a murine interleukin 17E polypeptide (GenBank Accession No. NP_542767)[SEQ ID NO:7].

FIG. 32 provides the sequence for a human interleukin 17E polypeptide precursor (GenBank Accession No. Q9H293) [SEQ ID NO:1].

FIG. 33 provides the sequence for a human interleukin 17E polypeptide precursor (GenBank Accession No. AAN39038) [SEQ ID NO:2].

FIG. 34 provides the sequence for a human interleukin 25 polypeptide (GenBank Accession No. AAL57622) [SEQ ID NO:3].

FIG. 35 provides the nucleic acid sequence encoding a murine interleukin 17E polypeptide (GenBank Accession No. NM_080729) [SEQ ID NO:8].

FIG. 36 provides the nucleic acid sequence encoding a human interleukin 17E polypeptide precursor (GenBank Accession No. AF305200) [SEQ ID NO:4].

FIG. 37 provides the nucleic acid sequence encoding a human interleukin 17E polypeptide precursor (GenBank Accession No. AF461739) [SEQ ID NO:5].

FIG. 38 provides the nucleic acid sequence encoding a human interleukin 25 polypeptide (GenBank Accession No. AF458059) [SEQ ID NO:6].

DETAILED DESCRIPTION OF THE INVENTION

Figure 1:
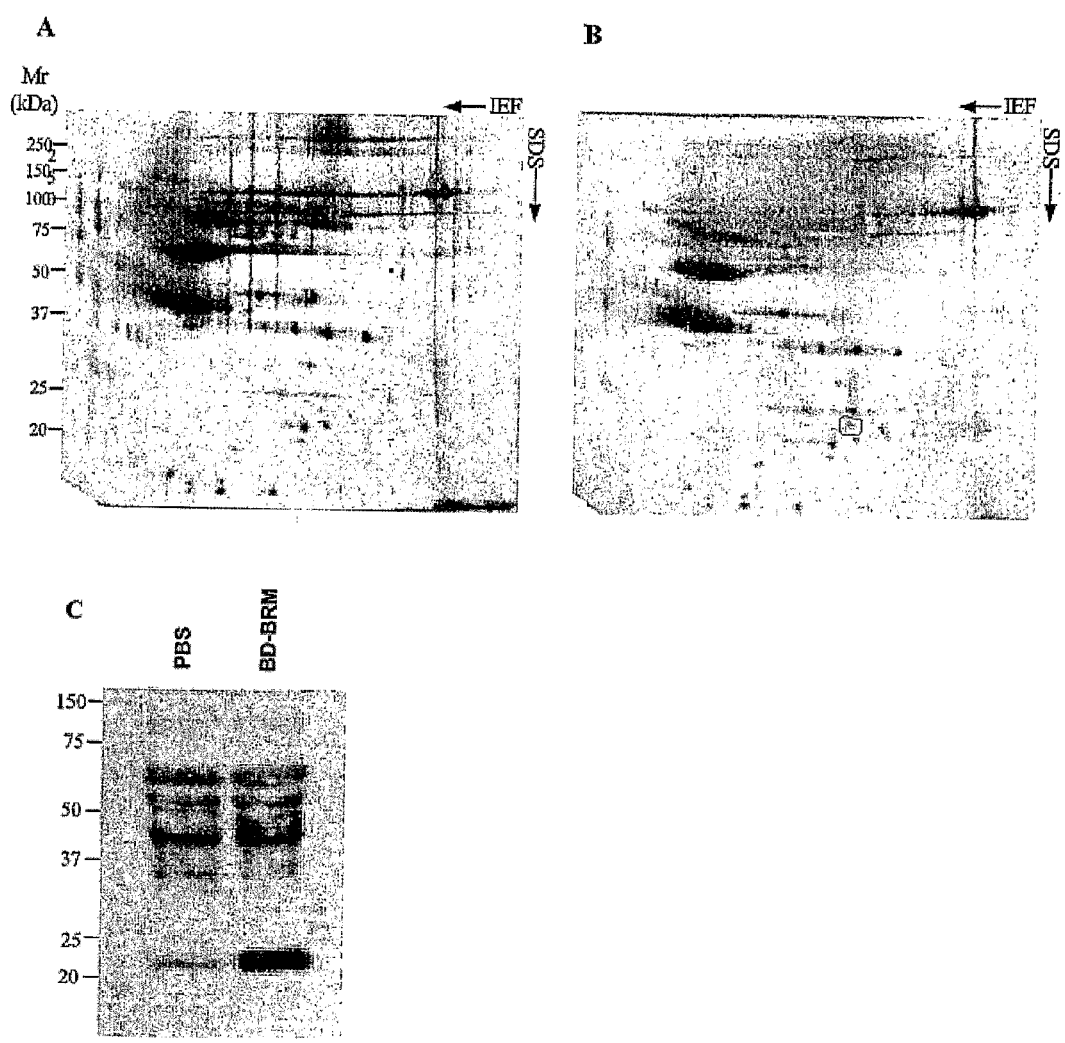
FIG. 1 depicts protein expression changes in sera collected from CD-1 nude mice bearing human melanoma tumour cells treated with a bile-derived biological response modifier (BD-BRM) composition (FIG. 1A) or PBS (FIG. 1B), and identification of IL-17E expression (FIG. 1C).

The present invention provides for the use of interleukin 17E (also known as interleukin 25) for the treatment of various types of cancers. As described above, previous reports of a family of IL-17 related polypeptides described the ability of these polypeptides (including an isoform of interleukin 17E) to stimulate T-cell proliferation/activation and have speculated that the polypeptides may be useful as adjuvants to increase the efficiency of standard chemotherapeutics through the stimulation of a T-cell response. No experimental data relating to this proposed anti-tumour immunoadjuvant effect, however, was provided.

In contrast, the present invention provides in vivo data demonstrating that interleukin 17E as a single agent is capable of inhibiting the growth of cancer cells and, moreover, that this anti-cancer effect is independent of T-cell activation. As shown in the Examples provided herein, this inhibitory effect of interleukin 17E on tumour growth was initially demonstrated by stimulation of endogenous interleukin 17E production in T-cell deficient nude mice. Administration of exogenous interleukin 17E to nude mice was demonstrated to have the same effect and both endogenous and exogenous interleukin 17E increased eosinophil infiltration into the tumour. The ability of interleukin 17E to inhibit tumour growth in the absence of a T-cell response indicates that interleukin 17E has a broad utility as an anti-cancer agent.

Accordingly, the present invention provides for a method of inhibiting tumour growth in a subject by increasing interleukin 17E levels in the subject. interleukin 17E levels can be increased by administering to the subject exogenous interleukin 17E, in the form of an interleukin 17E polypeptide or a polynucleotide encoding an interleukin 17E polypeptide, or the interleukin 17E levels can be increased by stimulating production of endogenous interleukin 17E, for example, through the administration of an inducer of interleukin 17E. The present invention further provides for a method of stimulating eosinophil infiltration into a tumour, and thereby inhibiting the growth of the tumour, by increasing interleukin 17E levels in a subject. The methods of the present invention are broadly applicable to a range of cancer patients, including immunocompromised patients with low levels of T-cells.

As demonstrated herein, interleukin 17E is capable of inhibiting tumour growth in vivo either as a single agent, or in combination with an anti-cancer therapeutic. The present invention thus also provides for the use of interleukin 17E alone, or in combination with one or more anti-cancer therapeutics, for inhibiting tumour growth in a subject. The interleukin 17E can be provided to the subject exogenously, as an interleukin 17E polypeptide or a polynucleotide encoding an interleukin 17E polypeptide, or it can be provided by stimulating production of endogenous interleukin 17E. Anti-cancer therapeutics contemplated by the present invention include, for example, standard chemotherapeutic drugs, immunotherapeutics, radiation, gene therapy, hormone manipulation and antisense therapy.

DEFINITIONS

Unless defined otherwise, all technical and scientific terms used herein have the same meaning as commonly understood by one of ordinary skill in the art to which this invention belongs.

The terms "therapy" and "treatment," as used interchangeably herein, refer to an intervention performed with the intention of alleviating the symptoms associated with, preventing the development of, or altering the pathology of a cancer. Thus, the terms therapy and treatment are used in the broadest sense, and include the prevention (prophylaxis), moderation, reduction, stabilisation or curing of a cancer at various stages. Those in need of therapy/treatment include those already having cancer as well as those prone to, or at risk of developing, cancer and those in whom cancer is to be prevented.

An "inducer of interleukin-17E", as used herein, refers to a compound, composition or treatment which induces or stimulates directly or indirectly endogenous production of interleukin 17E and/or the release of interleukin 17E in a subject.

An "anti-cancer therapeutic", as used herein, is a compound, composition or treatment that prevents or delays the growth and/or metastasis of cancer cells. Such anti-cancer therapeutics include, but are not limited to, chemotherapeutic drug treatment, radiation, gene therapy, hormonal manipulation, immunotherapy and antisense oligonucleotide therapy.

The term "subject" or "patient," as used herein, refers to a mammal in need of treatment.

The term "ameliorate" includes the arrest, prevention, decrease, or improvement in one or more the symptoms, signs, and features of the cancer being treated, both temporary and long-term.

The term "inhibit", as used herein, means to decrease, reduce, slow-down or prevent.

Administration of a compound "in combination with" one or more further therapeutic agents, is intended to include simultaneous (concurrent) administration and consecutive administration. Consecutive administration is intended to encompass various orders of administration of interleukin 17E and the one or more anticancer therapeutic(s) to the subject.

The term "polypeptide" is used herein as a generic term to refer to an amino acid sequence of at least 20 amino acids in length that can be a wild-type (naturally-occurring) protein sequence, a fragment of a wild-type protein sequence, a variant of a wild-type protein sequence, a derivative of a wild-type protein sequence, or an analogue of a wild-type protein sequence. Hence, native protein sequences and fragments, variants, derivatives and analogues of native protein sequences, as defined herein, are considered to be species of the polypeptide genus.

The term "isolated polypeptide," as used herein, refers to a polypeptide which by virtue of its origin is not associated with other polypeptides with which it is normally associated with in nature, and/or is isolated from the cell in which it normally occurs, and/or is free of other polypeptides from the same cellular source, and/or is expressed by a cell from a different species, and/or does not occur in nature.

"Naturally-occurring," as used herein, as applied to an object, refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The following terms are used herein to describe the sequence relationships between two or more polypeptides: "reference sequence," "window of comparison," "sequence identity" and "percent sequence identity." A "reference sequence" is a defined sequence used as a basis for a sequence comparison; a reference sequence may be a subset of a larger sequence, for example, as a segment of a full-length protein sequence, or may comprise a complete protein sequence. Generally, a reference polypeptide sequences is at least 7 amino acids in length and often at least 17 amino acids in length.

A "window of comparison", as used herein, refers to a conceptual segment of the reference sequence of at least 5 contiguous amino acid positions over which a candidate sequence may be compared to the reference sequence and wherein the portion of the candidate sequence in the window of comparison may comprise additions or deletions (i.e. gaps) of 20 percent or less as compared to the reference sequence (which does not comprise additions or deletions) for optimal alignment of the two sequences. The present invention contemplates various lengths for the window of comparison, up to and including the full length of either the reference or candidate sequence. Optimal alignment of sequences for aligning a comparison window may be conducted using the local homology algorithm of Smith and Waterman (*Adv. Appl. Math.* (1981) 2:482), the homology alignment algorithm of Needleman and Wunsch (*J. Mol. Biol.* (1970) 48:443), the search for similarity method of Pearson and Lipman (*Proc. Natl. Acad. Sci.* (*U.S.A.*) (1988) 85:2444), using computerised implementations of these algorithms (such as GAP, BESTFIT, FASTA, and TFASTA in the Wisconsin Genetics Software Package Release 7.0, Genetics Computer Group, 573 Science Dr., Madison, Wis.), using publicly available computer software such as ALIGN or Megalign (DNASTAR), or by inspection. The best alignment (i.e. resulting in the highest percentage of identity over the comparison window) is then selected.

The term "sequence identity" means that two polypeptide sequences are identical (i.e. on an amino acid-by-amino acid basis) over the window of comparison.

The term "percent (%) sequence identity," as used herein with respect to a reference sequence is defined as the percentage of amino acid residues in a candidate sequence that are identical with the residues in the reference polypeptide sequence over the window of comparison after optimal alignment of the sequences and introducing gaps, if necessary, to achieve the maximum percent sequence identity, without considering any conservative substitutions as part of the sequence identity.

As used herein, the term "about" refers to a +/−10% variation from the nominal value. It is to be understood that such a variation is always included in any given value provided herein, whether or not it is specifically referred to.

Interleukin 17E

In the context of the present invention, interleukin 17E for the treatment of cancer can be provided as a polypeptide or as a polynucleotide encoding and capable of expressing the interleukin 17E polypeptide, or by stimulation of endogenous production and/or release of interleukin 17E in vivo.

Interleukin 17E Polypeptides

It is known in the art that various isoforms of interleukin 17E (IL-17E; also known as IL-25) occur in nature. The isoforms, while possessing significant sequence identity, exhibit differences in both the N- and C-termini. In addition, differences in the expression patterns of the various isoforms has been observed (Kim et al. *Blood* 100: 2330-2340, 2002). The present invention contemplates the use of the various known isoforms of interleukin 17E to treat cancer and/or inhibit tumour growth.

The amino acid sequences of various isoforms of interleukin 17E are known in the art (see, for example, Lee et al. *J. Biol. Chem.* 276: 1660-1664, 2001; Kim et al. *Blood* 100: 2330-2340; Fort et al. *Immunity* 15:985-995, 2001; U.S. Pat. Nos. 6,579,520 and 6,569,645; U.S. Patent Application Nos. 20050074427, 20050048029, 20050003451, 20030124092, 20020037524, 20040043397, 20030203451, 20030199044, 20030186306, 20030180255, 20030054442, 20003008815, 20030003546, 20020182672 and 20020177188). Amino acid sequences for various isoforms of human interleukin 17E are also available from the GenBank database maintained by the NCBI (for example, GenBank Accession Nos. AAG40848, Q9H293 and NP_073626 (interleukin-17E isoform 1 precursor; SEQ ID NO:1); AAN39038 and NP_758525 (interleukin 17E, isoform 2 precursor; SEQ ID NO:2), and AAL57622 (interleukin 25; SEQ ID NO:3)) and are provided herein as FIGS. 32-34, respectively. The nucleic acid sequences encoding various isoforms of human interleukin 17E are also available from GenBank (GenBank Accession Nos. AF305200 and NM_022789 (interleukin 17E, transcript variant 1; SEQ ID NO:4); AF461739 and NM_172314 (interleukin 17E, transcript variant 2; SEQ ID NO:5) and AF458059 (interleukin 25 mRNA; SEQ ID NO:6)) and are provided herein as FIGS. 32-34. Similarly, the amino acid sequence for murine interleukin 17E is available from GenBank (NP_542767 and AAL57623 (interleukin 17E (interleukin 25): SEQ ID NO:7)), together with the corresponding nucleic acid sequence (NM_080729 and AF'458060, respectively (SEQ ID NO:8)). The amino acid sequence for murine interleukin 17E is provided herein as FIG. 31 and the nucleic acid sequence encoding murine interleukin 17E is provided herein as FIG. 35.

The present invention contemplates the use of interleukin 17E from various species to treat cancer and/or inhibit tumour growth. One embodiment of the present invention thus provides for the use of a human interleukin 17E to treat cancer and/or inhibit tumour growth. Another embodiment of the present invention provides for the use of a murine interleukin 17E to treat cancer and/or inhibit tumour growth.

Interleukin 17E is produced in vivo as a precursor protein that contains a signal peptide which is subsequently cleaved to produce the mature protein. It is known in the art that the length of the signal peptide varies with the different isoforms of interleukin 17E. For example, the precursor protein of the human interleukin 17E isoform identified by Lee et al. ((2001) *J. Biol. Chem.* 276(2):1660-1664 (GenBank Accession No. Q9H293)) is 177 amino acid residues in length and comprises a 32 amino acid residue signal peptide, while the precursor protein of the human interleukin 17E isoform identified by Kim et al. ((2002) *Blood.* 100:2330-2340 GenBank Accession No. AAN39038)) is 161 amino acid residues in length and comprises a 16 amino acid residue signal peptide. The precursor protein of murine interleukin 17E (Fort et al. (2002) *Immunity* 15:985-995 (GenBank Accession No. NP_542767)) is 169 amino acid residues in length and comprises a 16 amino acid residue signal peptide. The present invention contemplates the use of either the precursor form of interleukin 17E (i.e. the full-length interleukin 17E protein) or the mature form of interleukin 17E or a combination thereof to treat cancer and/or inhibit tumour growth. One embodiment of the present invention provides for the use of the mature form of a human interleukin 17E. In another embodiment of the present invention, the human interleukin 17E has an amino acid sequence as set forth in any one of SEQ ID NOs: 1, 2 or 3. In another embodiment of the present invention, the human interleukin 17E has an amino acid sequence as set forth in SEQ ID NO: 1, from amino acid 33 to 177. In another embodiment of the present invention, the human interleukin 17E has an amino acid sequence as set forth in SEQ ID NO: 2, from amino acid 17 to 169. Another embodiment of the present invention, provides for the use of a mature form of a murine interleukin 17E. In a further embodiment, the murine interleukin 17E has an amino acid sequence as set forth in SEQ ID NO: 7.

As would be appreciated by a worker skilled in the art, a substantially pure preparation of mature interleukin 17E may contain small amounts of precursor protein. Similarly, substantially pure preparations of precursor interleukin 17E may contain small amounts of mature protein. Such substantially pure preparations of mature interleukin 17E or precursor interleukin 17E are also suitable for use in the present invention.

In addition to the full-length and mature forms of naturally-occurring interleukin 17E polypeptides, interleukin 17E polypeptides for the purposes of the present invention also include biologically active fragments or variants of naturally-occurring interleukin 17E polypeptides, as well as analogues, derivatives or peptidomimetics of naturally-occurring interleukin 17E polypeptides or said biologically active fragments or variants.

For example, it known in the art that fragments of a polypeptide can retain the function of the naturally occurring form of the polypeptide. As used herein, a biologically active fragment is a fragment of the naturally-occurring (or wild-type) polypeptide that retains substantially the same activity as the wild-type polypeptide. Fragments typically are at least about 20 amino acids long. In one embodiment of the present invention, the fragments are at least about 50 amino acids long. In another embodiment, the fragments are at least about 70 amino acids long. In a further embodiment, the fragments are at least about 100 amino acids long. In another embodiment, the fragments are at least about 150 amino acids long. The term "fragment" also encompasses polypeptides corresponding to the wild-type protein that contain a deletion of 1 to about 50 amino acids from the N-terminus, from the C-terminus or from both the N- and C-termini of the wild-type sequence. Candidate fragments can be selected from random fragments generated from the naturally occurring protein or can be specifically designed. The activity of the fragments is tested and compared to that of the wild-type polypeptide and those fragments with substantially the same activity as the wild-type polypeptide are selected.

A variant polypeptide is one in which one or more amino acid residues have been deleted, added or substituted for those that appear in the amino acid sequence of the corresponding naturally-occurring interleukin 17E polypeptide. In the context of the present invention, a variant also retains substantially the same activity as the naturally-occurring interleukin 17E polypeptide. In accordance with one embodiment of the present invention, a variant has an amino acid sequence at least 80% identical to the corresponding naturally-occurring interleukin 17E polypeptide. In another embodiment, a variant has an amino acid sequence at least 85% identical to the corresponding naturally-occurring interleukin 17E polypeptide. In other embodiments, a variant has an amino acid sequence at least 90%, at least 95% or at least 98% identical to the corresponding naturally-occurring interleukin 17E polypeptide. In a further embodiment, the naturally-occurring interleukin 17E polypeptide has an amino acid sequence as set forth in any one of SEQ ID NOs: 1, 2, 3 or 7.

Typically, when a variant contains one or more amino acid substitutions they are "conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains);

glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group.

As is known in the art, analogues and derivatives of naturally-occurring polypeptides, and peptidomimetic compounds based on the sequence of a naturally-occurring polypeptide may have advantages over the naturally-occurring form, including, for example, greater chemical stability, increased resistance to proteolytic degradation, enhanced pharmacological properties (such as, half-life, absorption, potency and efficacy), altered specificity (for example, a broad-spectrum of biological activities) and/or reduced antigenicity. The present invention therefore also contemplates the use of analogues and derivatives of interleukin 17E, and peptidomimetic compounds based on interleukin 17E to treat cancer and/or inhibit tumour growth.

In the context of the present invention, a "derivative" is a polypeptide containing additional chemical or biochemical moieties not normally a part of a naturally occurring sequence. Derivatives include polypeptides in which the amino-terminus and/or the carboxy-terminus and/or one or more amino acid side chain has been derivatised with a suitable chemical substituent group, as well as cyclic, dual and multimeric polypeptides, polypeptides fused to other proteins or carriers, glycosylated or phosphorylated polypeptides, polypeptides conjugated to lipophilic moieties (for example, caproyl, lauryl, stearoyl moieties) and polypeptides conjugated to an antibody or other biological ligand.

Examples of chemical substituent groups that may be used to derivatise polypeptides include, but are not limited to, short-chain (e.g. 1-10 carbon) alkyl, cycloalkyl and aryl groups; acyl groups, including short-chain (e.g. 1-10 carbon) alkanoyl and aroyl groups; esters; amides; halogens; hydroxyls; carbamyls; and the like. The substituent group may also be a blocking group such as Fmoc (fluorenylmethyl-O—CO—), carbobenzoxy (benzyl-O—CO—), monomethoxysuccinyl, naphthyl-NH—CO—, acetylaminocaproyl and adamantyl-NH—CO—. Other derivatives include C-terminal hydroxymethyl derivatives, O-modified derivatives (for example, C-terminal hydroxymethyl benzyl ether) and N-terminally modified derivatives including substituted amides such as alkylamides and hydrazides.

The term "cyclic" polypeptide refers to a cyclic derivative of a polypeptide to which, for example, two or more additional amino acid residues suitable for cyclisation have been added. These additional amino acids may be added at the carboxyl terminus and at the amino terminus, or they may be at internal positions.

Alternatively, a cyclic polypeptide may take advantage of cysteine residues that occur naturally in the amino acid sequence to form a disulphide bond and thereby cyclise the polypeptide. A cyclic polypeptide can contain either an intramolecular disulphide bond, i.e., —S—S—; an intramolecular amide bond between the two added residues, i.e., —CONH— or —NHCO—; or intramolecular S-alkyl bonds, i.e., —S—(CH$_2$)—CONH— or —NH—CO(CH$_2$)$_n$—S—, wherein n is 1, 2, or more.

A dual polypeptide consists of two of the same, or two different, polypeptides/peptides covalently linked to one another, either directly or through a spacer such as a short stretch of alanine residues or a putative site for proteolysis (see, for example, U.S. Pat. No. 5,126,249 and European Patent No. 495,049). Multimers are polymeric molecules formed from a number of the same or different polypeptides. The polymerisation is carried out with a suitable polymerisation agent, such as 0.1% glutaraldehyde (see, for example, Audibert et al., 1981, *Nature* 289:593).

In the context of the present invention, an "analogue" is a polypeptide comprising one or more non-naturally occurring amino acid. For example, a polypeptide analogue of the invention may have one or more amino acid residues replaced by the corresponding D-amino acid residue or with another non-naturally occurring amino acid. Examples of non-naturally occurring amino acids include, but are not limited to, N-α-methyl amino acids, C-α-methyl amino acids, β-methyl amino acids, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP), phenylglycine, 2-naphthylalanine (2-Nal), 1,2,3,4-tetrahydroisoquinoline-3-carboxylic acid (Tic), β-2-thienylalanine (Thi), methionine sulphoxide (MSO) and homoarginine (Har).

Peptidomimetics are compounds that are structurally similar to polypeptides and contain chemical moieties that mimic the function of the polypeptides. For example, if a polypeptide contains two charged chemical moieties having functional activity, a mimetic places two charged chemical moieties in a spatial orientation and constrained structure so that the charged chemical function is maintained in three-dimensional space. The term peptidomimetic thus is intended to include isosteres. The term "isostere," as used herein, refers to a chemical structure that can be substituted for a polypeptide because the steric conformation of the chemical structure is similar to that of the polypeptide, for example, the structure fits a binding site specific for the polypeptide. Examples of peptidomimetics include polypeptides comprising one or more backbone modifications (i.e., amide bond mimetics), which are well known in the art. Examples of amide bond mimetics include, but are not limited to, —CH$_2$NH—, —CH$_2$S—, —CH$_2$CH$_2$—, —CH=CH— (cis and trans), —COCH$_2$—, —CH(OH)CH$_2$—, and —CH$_2$SO—(see, for example, Spatola, Vega Data Vol. 1, Issue 3, (1983); Spatola, in *Chemistry and Biochemistry of Amino Acids Peptides and Proteins*, Weinstein, ed., Marcel Dekker, New York, p. 267 (1983); Morley, J. S., *Trends Pharm. Sci.* pp. 463-468 (1980); Hudson et al., *Int. J. Pept. Prot. Res.* 14:177-185 (1979); Spatola et al., *Life Sci.* 38:1243-1249 (1986); Hann, *J. Chem. Soc. Perkin Trans. I* 307-314 (1982); Almquist et al., *J. Med. Chem.* 23:1392-1398 (1980); Jennings-White et al., *Tetrahedron Lett.* 23:2533 (1982); Szelke et al., EP 45665 (1982); Holladay et al., *Tetrahedron Lett.* 24:4401-4404 (1983); and Hruby, *Life Sci.* 31:189-199 (1982)). Other examples of peptidomimetics include polypeptides substituted with one or more benzodiazepine molecules (see, for example, James, G. L. et al. (1993) *Science* 260:1937-1942) and polypeptides comprising backbones crosslinked to form lactams or other cyclic structures.

One skilled in the art will appreciate that not all amino acids in a polypeptide need be modified. Similarly not all amino acids need be modified in the same way. Polypeptide derivatives, analogues and peptidomimetics of the present invention thus include chimeric molecules that contain two or more chemically distinct regions, each region comprising at least one amino acid or modified version thereof.

In accordance with the present invention, an analogue, derivative, variant or biologically active fragment has substantially identical activity as a naturally occurring interleukin 17E polypeptide. The term "substantially identical activity" indicates an activity that is about 50% of the corresponding activity of a naturally-occurring interleukin 17E polypeptide. In one embodiment, substantially identical activity indicates an activity that is about 60% of the corresponding activity of a naturally-occurring interleukin 17E polypeptide. In another embodiment, it indicates an activity that is about 75% of the corresponding activity of a naturally-occurring interleukin 17E polypeptide. In the context of the present invention, biological activity of interleukin 17E refers to one or more of the following: the ability of the polypeptide to bind the interleukin 17E receptor (IL17Rh1; also known as IL-17 B Receptor (1L-17B R)), the ability of the polypeptide to stimulate production of IL-8, the ability of the polypeptide to promote expression of prototypical Th2 genes (such as IL-4, IL-5, IL-6 and IL-10), the ability of the polypeptide to induce eosinophilia and the ability of the polypeptide to inhibit tumour growth. Methods of assessing these biological activities for a candidate IL-17E polypeptide are well known in the art and include the methods described below.

Preparation of Interleukin 17E Polypeptides

Mature interleukin 17E polypeptides are available commerically. For example, recombinant human interleukin 17E in the form of an amino acid disulfide-linked homo-dimer (each dimer comprising amino acids 33-177 of the sequence as set forth in Genbank Accession No. Q9H293) can be purchased from R&D Systems, Inc. (Minneapolis, Minn.). Recombinant human interleukin 17E can also be purchased from PeproTech, Inc. (Rocky Hill, N.J.) as a 33.8 kDa disulfide-linked homodimer of two 145 amino acid polypeptide chains of the sequence set forth in AAG40848 from amino acid 33 to 177); and from Antigenix America, Inc. (Huntington Station, N.Y.) and Cell Sciences (Canton, Mass.). Recombinant murine interleukin 17E is also available commercially from R&D Systems, Inc.

Alternatively, the interleukin 17E polypeptides can be isolated or prepared using techniques well known in the art, such as purification from cell extracts or the use of recombinant techniques (see, for example, Coligan, et al., eds., *Current Protocols in Protein Science*, J. Wiley & Sons, Inc., New York, N.Y., and Ausubel et al. (1994 & updates) *Current Protocols in Molecular Biology*, John Wiley & Sons, New York). Methods for generating polypeptide fragments are well known in the art and include enzymatic, chemical or mechanical cleavage of the wild-type protein or a recombinant version thereof, expression of nucleic acids encoding such fragments, and the like.

Shorter sequences, such as biologically active fragments, can also be chemically synthesised by methods known in the art including, but not limited to, exclusive solid phase synthesis, partial solid phase synthesis, fragment condensation or classical solution synthesis (Merrifield (1963) *J. Am. Chem. Soc.* 85:2149; Merrifield (1986) *Science* 232:341).

Modifications of the polypeptides to provide analogues and derivatives of naturally-occurring polypeptides can be introduced using standard peptide chemistry techniques. Methods of synthesizing peptides having one or more modified peptide bonds are known in the art (see, for example, "Solid Phase Peptide Synthesis" *Methods in Enzymology* (ed. Fields, G. B. (1997) Academic Press, San Diego). Covalent modifications of the polypeptide can be introduced, for example, by reacting targeted amino acid residues with an organic derivatising agent that is capable of reacting with selected side chains or terminal residues as is known in the art. Selection of appropriate derivatising agent(s) can be readily accomplished by a worker skilled in the art.

Cyclic polypeptides containing an intramolecular disulphide bond may be prepared by conventional solid phase synthesis while incorporating suitable S-protected cysteine or homocysteine residues at the positions selected for cyclisation (see, for example, Sahm et al., 1996, *J. Pharm. Pharmacol.* 48:197). Following completion of the chain assembly, cyclisation can be performed either by selective removal of the S-protecting groups with a consequent on-support oxidation of free corresponding SH-functions, to form S—S bonds, followed by conventional removal of the product from the support and appropriate purification procedure, or by removal of the polypeptide from the support along with complete side-chain deprotection, followed by oxidation of the free SH-functions in highly dilute aqueous solution. Similarly, cyclic derivatives containing an intramolecular amide bond may be prepared by conventional solid phase synthesis while incorporating suitable amino and carboxyl side-chain protected amino acid derivatives at the positions selected for cyclisation, and cyclic polypeptides containing intramolecular —S-alkyl bonds can be prepared by conventional solid phase synthesis while incorporating an amino acid residue with a suitable amino-protected side chain, and a suitable S-protected cysteine or homocysteine residue at the positions selected for cyclisation.

The interleukin 17E polypeptides can be purified when necessary using standard techniques such as chromatography (e.g. ion exchange, affinity, and sizing column chromatography or high performance liquid chromatography), centrifugation, differential solubility, or by other techniques familiar to a worker skilled in the art.

Interleukin 17E Polynucleotides and Recombinant Techniques

As indicated above, for the purposes of the present invention, interleukin 17E can be provided as a polypeptide, by stimulating endogenous production and/or release of interleukin 17E in vivo or as a polynucleotide capable of expressing the polypeptide. Accordingly, the present invention also provides for interleukin 17E polynucleotides. The polynucleotides can be used directly to express the polypeptide in vivo or can be used to produce interleukin 17E polypeptides by recombinant techniques. Typically recombinant techniques involve transformation (including transfection, transduction, or infection) of a suitable host cell with an expression vector comprising a polynucleotide encoding the polypeptide.

As indicated above, the polynucleotide sequences for various isoforms of interleukin 17E are known in the art and may be used as a basis for the polynucleotides for the purposes of the invention. The polynucleotides can be derived or purified from a suitable source by standard techniques. The polynucleotides can be genomic DNA or RNA or cDNA prepared from isolated mRNA. Alternatively, the known sequences may be used to prepare probes to obtain other polynucleotide sequences encoding an interleukin 17E polypeptide from various sources using standard techniques.

Polynucleotides encoding fragments or variants of a naturally-occurring interleukin 17E polypeptide can be constructed by deletion, addition, and/or substitution of one or more nucleotides within the coding sequence using standard techniques, such as site-directed mutagenesis techniques.

The interleukin 17E polypeptides can also be produced as fusion proteins. One use of such fusion proteins is to improve the purification or detection of the polypeptide. For example, an interleukin 17E polypeptide can be fused to an immunoglobulin Fc domain and the resultant fusion protein can be readily purified using a protein A column. Other examples of fusion proteins include polypeptides fused to histidine tags (allowing for purification on $Ni^{2+}$ resin columns), to glutathione-S-transferase (allowing purification on glutathione columns) or to biotin (allowing purification on streptavidin columns or with streptavidin labelled magnetic beads). Once the fusion protein has been purified, the tag may be removed by site-specific cleavage using chemical or enzymatic methods known in the art. Alternatively, if the tag does not interfere with the activity of the interleukin 17E polypeptide, the fusion protein can be left intact.

Specific initiation signals may be required for efficient translation of a cloned polynucleotide. These signals include, for example an ATG initiation codon and adjacent sequences. In cases where an entire wild-type gene or cDNA, including its own initiation codon and adjacent sequences, is inserted into the appropriate expression vector, additional translational control signals may not be needed. In other cases, exogenous translational control signals, including, for example, the ATG initiation codon, must be provided. One skilled in the art will understand that the initiation codon should be in phase with the reading frame of the desired coding sequence to ensure translation of the entire insert. The exogenous translational control signals and initiation codons can be natural or synthetic. The efficiency of expression may be enhanced by the inclusion of appropriate transcription enhancer elements and/or transcription terminators (Bittner et al. (1987) *Methods in Enzymol.* 153, 516).

Suitable expression vectors for use with the polynucleotide sequences contemplated by the present invention include, but are not limited to, plasmids, phagemids, viral particles and vectors, phage and the like. For insect cells, baculovirus expression vectors are suitable. For plant cells viral expression vectors (such as cauliflower mosaic virus and tobacco mosaic virus) and plasmid expression vectors (such as the Ti plasmid) are suitable. The entire expression vector, or a part thereof, can be integrated into the host cell genome. In some circumstances, it is desirable to employ an inducible expression vector as known in the art.

Those skilled in the field of molecular biology will understand that a wide variety of expression systems can be used to provide the recombinant polypeptide. The precise host cell used is not critical to the invention. The polypeptide can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, or HeLa cells; insect cells; or plant cells). The methods of transformation or transfection and the choice of expression vector will depend on the host system selected and can be readily determined by one skilled in the art. Transformation and transfection methods are described, for example, in Ausubel et al. (1994) *Current Protocols in Molecular Biology*, John Wiley & Sons, New York; and various expression vectors may be chosen from those provided, e.g., in Cloning Vectors: A Laboratory Manual (Pouwels et al., 1985, Supp. 1987) and by various commercial suppliers.

In addition, a host cell may be chosen which modulates the expression of the inserted sequences, or modifies and processes the gene product in a specific, desired fashion. Such modifications (e.g., glycosylation) and processing (e.g., cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed heterologous protein.

The host cells harbouring the expression vehicle can be cultured in conventional nutrient media adapted as needed for activation of a chosen gene, repression of a chosen gene, selection of transformants, or amplification of a chosen gene according to known procedures.

Biological Activity of the Interleukin 17E Polypeptides

As indicated above, candidate interleukin 17E polypeptides that are analogues, derivatives, variants or biologically active fragments of a naturally occurring IL-17E polypeptide have substantially identical activity as the naturally occurring interleukin 17E polypeptide, wherein the activity is one or more of the following: the ability of the polypeptide to bind the interleukin 17E receptor (IL17Rh1; also known as IL-17 B Receptor (1L-17B R)), the ability of the polypeptide to stimulate production of IL-8, the ability of the polypeptide to promote expression of prototypical Th2 genes (such as IL-4, IL-5, IL-6 and IL-10), the ability of the polypeptide to induce eosinophilia and the ability of the polypeptide to inhibit tumour growth.

The above biological activities for a candidate interleukin 17E polypeptide can be measured using standard techniques known in the art (see, for example, Coligan, et al., eds., *Current Protocols in Protein Science*, J. Wiley & Sons, Inc., New York, N.Y., and Coligan, et al., eds., *Current Protocols in Immunology*, J. Wiley & Sons, Inc., New York, N.Y.).

For example, the ability of the polypeptide to bind the interleukin 17E receptor can be measured by Western blot techniques (see Lee, et al, *J. Biol. Chem.*, 276:1660-1664 (2001)). The ability of the polypeptide to stimulate production of IL-8 can be assessed in vitro by contacting an appropriate cell line (for example, human TK-10 kidney-derived cell-lines) with the candidate polypeptide, or a polynucleotide encoding the polypeptide, and assessing the amount of IL-8 produced compared to an appropriate control (see, for example, Lee, et al, *J. Biol. Chem.*, 276:1660-1664 (2001)). The ability of the candidate interleukin 17E polypeptide to stimulate production of IL-8 can also be assessed in vivo by administering the candidate polypeptide, or a polynucleotide encoding the polypeptide, to an appropriate test animal and assessing the amount of IL-8 produced in selected tissues compared to an appropriate control. IL-8 production can be determined, for example, by standard ELISA. IL-8 ELISA kits are available commercially (for example from R&D Systems, Inc., Minneapolis, Minn.). Similar techniques can be employed to determine the ability of the polypeptide to promote expression of prototypical Th2 genes (such as IL-4, IL-5, IL-6 and IL-10) (see, for example, Kim, et al., *Blood,* 100:2330-2340 (2002); Pan et al., *J. Immunol.,* 167:6559-67 (2001)).

The ability of the polypeptide to induce eosinophilia can be assessed in vivo using techniques known in the art (see, for example, Kim, et al., *Blood,* 100:2330-2340 (2002) and the Examples provided herein). The ability of the polypeptide to inhibit tumour growth can also be assessed in vivo using Standard techniques for determining the anti-cancer activity of a compound (see, for example, Enna, et al., *Current Protocols in Pharmacology*, J. Wiley & Sons, Inc., New York, N.Y.). Exemplary methods are described in more detail below and in the Examples provided herein.

Inducers of Interleukin 17E

As indicated above, for the purposes of the present invention, interleukin 17E can also be provided by stimulating endogenous production and/or release of interleukin 17E in vivo. Accordingly, the present invention also provides for inducers of interleukin 17E to stimulate endogenous interleukin 17E production and/or release in vivo. Alternatively, the inducers may be used to stimulate interleukin 17E production and/or release in vitro for subsequent isolation and use. A worker skilled in the art would be able to readily isolate the interleukin 17E using techniques known in the art.

One example of an inducer of interleukin 17E is a bile-derived biological response modifier (BD-BRM) composition, as described in International Patent Application Nos. WO 95/07089, WO 96/28175 and WO 02/38164 and U.S. Pat. Nos. 6,280,774 and 6,596,319. The BD-BRM composition comprises small molecular weight components of less than 3000 daltons, and has at least one of the following properties:

a) is extracted from the bile of animals;
b) is capable of stimulating or activating monocytes and/or macrophages in vitro and/or in vivo;
c) is capable of modulating tumour necrosis factor production and/or release;
d) contains no measurable level of IL-1α, IL-1β, TNF, IL-6, IL-8, IL-4, GM-CSF or IFN-γ,
e) shows no cytotoxicity to human peripheral blood mononuclear cells or lymphocytes; and
f) is not an endotoxin.

Other inducers can be readily identified by a worker skilled in the art. The ability of the candidate compound or composition to stimulate IL-17E production and/or release can be tested by treating either an appropriate cell line or cells isolated from a test animal with the candidate compound or composition and analysing the amount of IL-17E produced, either directly by analysing the amount of protein produced, for example, using Western blot, ELISA or flow cytometry techniques, or indirectly by detecting the amount of IL-17E mRNA produced, for example, by hybridisation analysis, Northern blot analysis or RT-PCR. The amount of IL-17E produced in cells treated with the candidate compound or composition can then be compared with an appropriate control, such as untreated cells, or cells treated with a standard control compound known to stimulate IL-17E production. Alternatively, the ability of the candidate compound or composition to stimulate endogenous IL-17E production and/or release can be tested in vivo using similar methods in normal test animals or in an appropriate animal model of disease. For example, serum of mice treated with the candidate compound or composition can be analysed for interleukin 17E and compared with an appropriate control, such as serum from untreated animals, or serum from animals treated with a standard control compound known to stimulate IL-17E production.

A number of compounds have been identified that stimulate interleukin 17E (interleukin 25) production. For example, the calcium ionophore A23187 in combination with phorbol myristate acetate (PMA) has been shown to induce IL-25 production in mouse bone marrow-derived mast cells in vitro (Ikeda K., et al., (2003) Blood 101:3594-3596). Immunoglobin E (IgE) cross-linking of mouse bone marrow-derived mast cells has also been shown to induce IL-25 production in vitro (Ikeda K., et al., (2003) Blood 101:3594-3596). Titanium dioxide ($TiO_2$) particles given to rats by intratracheal administration has also been shown to induce IL-25 production in alveolar macrophages (Kang C M. et al., (2005) Am J Respir Cell Mol. Biol. 33:290-6). In addition, mice infected with either the fungus Aspergillus fumigatus or the nematode parasite Nippostrongylus brasiliensis show increased expression of IL-25 mRNA in the lung and gut, respectively (Hurst, S. D., et al., (2002) J. Immunol. 169:443-53.

Anti-Cancer Therapeutics

As indicated above, the present invention contemplates the use of interleukin 17E either alone or in combination with one or more anti-cancer therapeutics in the treatment of cancer. The anti-cancer therapeutics for use in the present invention include compounds, compositions or treatments that prevent or delay the growth and/or metastasis of cancer cells. Such anti-cancer therapeutics include, but are not limited to, chemotherapeutic drug treatment, radiation, gene therapy, hormonal manipulation, immunotherapy and antisense oligonucleotide therapy. It is to be understood that anti-cancer therapeutics for use in the present invention also include novel compounds or treatments developed in the future.

Chemotherapeutics

A wide variety of chemotherapeutics are known in the art and can be used in combination therapies with interleukin 17E. Known chemotherapeutic agents include those that are specific for the treatment of a particular type of cancer as well as those that are applicable to a range of cancers, such as doxorubicin, capecitabine, mitoxantrone, irinotecan (CPT-11), cisplatin and gemcitabine. Etoposide is generally applicable in the treatment of leukaemias (including acute lymphocytic leukaemia and acute myeloid leukaemia), germ cell tumours, Hodgkin's disease and various sarcomas. Cytarabine (Ara-C) is also applicable in the treatment of various leukaemias, including acute myeloid leukaemia, meningeal leukaemia, acute lymphocytic leukaemia, chronic myeloid leukaemia, erythroleukaemia; as well as non-Hodgkin's lymphoma.

The present invention contemplates the use of both types of chemotherapeutic agent in conjunction with interleukin 17E. Exemplary chemotherapeutics that can be used alone or in various combinations for the treatment specific cancers are provided in Table 1. One skilled in the art will appreciate that many other chemotherapeutics are available and that the following list is intended to provide non-limiting examples only.

TABLE 1

Exemplary Chemotherapeutics used in the Treatment of Some Common Cancers

| CANCER | CHEMOTHERAPEUTIC | |
|---|---|---|
| Acute lymphocytic leukaemia (ALL) | Pegaspargase (e.g. Oncaspar ®) Cytarabine | L-asparaginase |
| Acute myeloid leukaemia (AML) | Cytarabine | Idarubicin |
| Brain cancer | Procarbazine (e.g. Matulane ®) Platinum analogues | Nitrosoureas Temozolomide |
| Breast cancer | Capecitabine (e.g. Xeloda ®) 5-fluorouracil (5-FU) Paclitaxel (e.g. Taxol ®) Docetaxel (e.g. Taxotere ®) Epi-doxorubicin (epirubicin) Tamoxifen | Cyclophosphamide Carboplatin Cisplatin Ifosfamide Doxorubicin (e.g. Adriamycin ®) |

TABLE 1-continued

Exemplary Chemotherapeutics used in the Treatment of Some Common Cancers

| CANCER | CHEMOTHERAPEUTIC | |
| --- | --- | --- |
| Chronic myeloid leukaemia (CML) | Cytarabine | |
| Colon cancer | Edatrexate (10-ethyl-10-deaza-aminopterin) | |
| | Methyl-chloroethyl-cyclohexyl-nitrosourea | |
| | 5-fluorouracil (5-FU) | Levamisole |
| | Fluorodeoxyuridine (FUdR) | Vincristine |
| | Capecitabine (e.g. Xeloda ®) | Oxaliplatin |
| Colorectal cancer | Irinotecan (CPT-11, e.g. Camptosar ®) | |
| | Loperamide (e.g. Imodium ®) | 5-fluorouracil (5-FU) |
| | Topotecan (e.g. Hycamtin ®) | Methotrexate |
| | Capecitabine (e.g. Xeloda ®) | Oxaliplatin |
| Gall bladder | 5-fluorouracil (5-FU) | |
| Genitourinary cancer | Docetaxel (e.g. Taxotere ®) | |
| Head and neck cancer | Docetaxel (e.g. Taxotere ®) | Cisplatin |
| Non-Hodgkin's Lymphoma | Procarbazine (e.g. Matulane ®) | Cytarabine |
| | Etoposide | |
| Non-small-cell lung (NSCL) cancer | Vinorelbine Tartrate (e.g. Navelbine ®) | |
| | Irinotecan (CPT-11, e.g. Camptosar ®) | |
| | Docetaxel (e.g. Taxotere ®) | Paclitaxel (e.g. Taxol ®) |
| | Gemcitabine (e.g. Gemzar ®) | Topotecan |
| Oesophageal cancer | Porfimer Sodium (e.g. Photofrin ®) | |
| | Cisplatin, | |
| Ovarian cancer | Irinotecan (CPT-11, e.g. Camptosar ®) | |
| | Topotecan (e.g. Hycamtin ®) | |
| | Docetaxel (e.g. Taxotere ®) | Paclitaxel (e.g. Taxol ®) |
| | Gemcitabine (e.g. Gemzar ®) | Amifostine (e.g. Ethyol ®) |
| Pancreatic cancer | Irinotecan (CPT-11, e.g. Camptosar ®) | |
| | Gemcitabine (e.g. Gemzar ®) | 5-fluorouracil (5-FU) |
| Promyelocytic leukaemia | Tretinoin (e.g. Vesanoid ®) | |
| Prostate cancer | Goserelin Acetate (e.g. Zoladex ®) | |
| | Mitoxantrone (e.g. Novantrone ®) | |
| | Prednisone (e.g. Deltasone ®) | Liarozole |
| | Nilutamide (e.g. Nilandron ®) | Flutamide (e.g. Eulexin ®) |
| | Finasteride (e.g. Proscar ®) | Terazosin (e.g. Hytrin ®) |
| | Doxazosin (e.g. Cardura ®) | Cyclophosphamide |
| | Docetaxel (e.g. Taxotere ®) | Estramustine |
| | Luteinizing hormone releasing hormone agonist | |
| Renal cancer | Capecitabine (e.g. Xeloda ®) | Gemcitabine (e.g. Gemzar ®) |
| Small cell lung cancer | Cyclophosphamide | Vincristine |
| | Doxorubicin | Etoposide |
| Solid tumours | Gemicitabine (e.g. Gemzar ®) | Cyclophosphamide |
| | Capecitabine (e.g. Xeloda ®) | Ifosfamide |
| | Paclitaxel (e.g. Taxol ®) | Cisplatin |
| | Docetaxel (e.g. Taxotere ®) | Carboplatin |
| | Epi-doxorubicin (epirubicin) | Doxorubicin (e.g. Adriamycin ®) |
| | 5-fluorouracil (5-FU) | |

As indicated above, combinations of chemotherapeutics may be employed. Combination therapies using standard cancer chemotherapeutics are well known in the art and such combinations also can be used in conjunction with interleukin 17E.

Exemplary combination therapies include for the treatment of breast cancers the combination of epirubicin with paclitaxel or docetaxel, or the combination of doxorubicin or epirubicin with cyclophosphamide. Polychemotherapeutic regimens are also useful and may consist, for example, of doxorubicin/cyclophosphamide/5-fluorouracil or cyclophosphamide/epirubicin/5-fluorouracil. Many of the above combinations are useful in the treatment of a variety of other solid tumours.

Combinations of etoposide with either cisplatin or carboplatin are used in the treatment of small cell lung cancer. In the treatment of stomach or oesophageal cancer, combinations of doxorubicin or epirubicin with cisplatin and 5-fluorouracil are useful. For colorectal cancer, CPT-11 in combination with 5-fluorouracil-based drugs, or oxaliplatin in combination with 5-fluorouracil-based drugs can be used. Oxaliplatin may also be used in combination with capecitabine.

Other examples include the combination of cyclophosphamide, doxorubicin, vincristine and prednisone in the treatment of non-Hodgkin's lymphoma; the combination of doxorubicin, bleomycin, vinblastine and dacarbazine (DTIC) in the treatment of Hodgkin's disease and the combination of cisplatin or carboplatin with any one, or a combination, of gemcitabine, paclitaxel, docetaxel, vinorelbine or etoposide in the treatment of non-small cell lung cancer.

Various sarcomas are treated by combination therapy, for example, for osteosarcoma combinations of doxorubicin and cisplatin or methotrexate with leucovorin are used; for advanced sarcomas etoposide can be used in combination with ifosfamide; for soft tissue sarcoma doxorubicin or dacarbazine can be used alone or, for advanced sarcomas doxorubicin can be used in combination with ifosfamide or dacarbazine, or etoposide in combination with ifosfamide.

Ewing's sarcoma/peripheral neuroectodermal tumour (PNET) or rhabdomyosarcoma can be treated using etoposide and ifosfamide, or a combination of vincristine, doxorubicin and cyclophosphamide.

The alkylating agents cyclophosphamide, cisplatin and melphalan are also often used in combination therapies with other chemotherapeutics in the treatment of various cancers.

In one embodiment of the present invention, interleukin 17E is used in combination with one or more chemotherapeutics are used to treat cancer. In another embodiment of the present invention, at least one of the chemotherapeutics is a broad-spectrum chemotherapeutic. In a further embodiment, at least one of the chemotherapeutics is dacarbazine (DTIC), cisplatin, Taxotere®, Tarceva®, or CPT-11.

Immunotherapeutics

A wide variety of immunotherapeutics are also known in the art and can be used in combination therapies with interleukin 17E. Immunotherapy is a therapy that directly or indirectly stimulates or enhances the immune system's response to cancer cells and/or lessens the side effects that may have been caused by other anti-cancer agents. Immunotherapy is also referred to in the art as immunologic therapy, biological therapy, biological response modifier therapy and biotherapy. Examples of common immunotherapeutic agents known in the art and contemplated for inclusion in the combination products of the present invention include, but are not limited to, cytokines, non-cytokine adjuvants, antibodies (including, but not limited to monoclonal antibodies), vaccines (including, but not limited to cancer vaccines) and immunomodulatory compositions.

Immunotherapeutic agents can be non-specific, i.e. boost the immune system generally so that it becomes more effective in fighting the growth and/or spread of cancer cells, or they can be specific, i.e. targeted to the cancer cells themselves. Immunotherapy regimens may combine the use of non-specific and specific immunotherapeutic agents.

Non-specific immunotherapeutic agents are substances that stimulate or indirectly augment the immune system. Non-specific immunotherapeutic agents have been used alone as the main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines.

A number of cytokines have found application in the treatment of cancer either as general non-specific immunotherapies designed to boost the immune system, or as adjuvants provided with other therapies. Suitable cytokines for use in the combination therapies of the present invention include, but are not limited to, interferons, interleukins and colony-stimulating factors.

Interferons (IFNs) contemplated by the present invention for use in combination with interleukin 17E include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages.

Interleukins contemplated by the present invention for use in combination with interleukin 17E include IL-2, IL-4, IL-11 and IL-12 (or oprelvekin). Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Interleukins, alone or in combination with other immunotherapeutics or with chemotherapeutics, have shown efficacy in the treatment of various cancers including renal cancer (including metastatic renal cancer), melanoma (including metastatic melanoma), ovarian cancer (including recurrent ovarian cancer), cervical cancer (including metastatic cervical cancer), breast cancer, colorectal cancer, lung cancer, brain cancer, prostate cancer, leukemias and lymphomas.

An interleukin-immunotoxin conjugate known as denileukin diftitox (or Ontak; Seragen, Inc), which comprises IL-2 conjugated to diphtheria toxin, has been approved by the FDA for the treatment of cutaneous T cell lymphoma and may also be included in the combination therapies of the present invention.

Colony-stimulating factors (CSFs) contemplated by the present invention for use in the combination therapies include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in patients undergoing traditional chemotherapy. Accordingly, treatment with CSFs can be helpful in decreasing the side effects associated with chemotherapy and can allow for higher doses of chemotherapeutic agents to be used.

Examples of non-cytokine non-specific immunotherapeutic agents suitable for use in the combinations of the present invention include, but are not limited to, Levamisole, alum hydroxide (alum), *bacillus* Calmette-Guerin (BCG), incomplete Freund's Adjuvant (IFA), QS-21, DETOX, Keyhole limpet hemocyanin (KLH), dinitrophenyl (DNP) and bile-derived biological response modifier derived from bovine bile (BD-BRM) (described in International Patent Application Nos. WO 95/07089, WO 96/28175 and WO 02/38164 and U.S. Pat. Nos. 6,280,774 and 6,596,319). Non-cytokine adjuvants in combination with other immuno- and/or chemotherapeutics have demonstrated efficacy against various cancers including, for example, colon cancer and colorectal cancer (Levimasole); melanoma (BCG and QS-21); renal cancer and bladder cancer (BCG).

In one embodiment of the present invention, interleukin 17E is used in combination therapies with BD-BRM. The BD-BRM composition comprises small molecular weight components of less than 3000 daltons, and has at least one of the following properties:
a) is extracted from the bile of animals;
b) is capable of stimulating or activating monocytes and/or macrophages in vitro and/or in vivo;
c) is capable of modulating tumour necrosis factor production and/or release;
d) contains no measurable level of IL-1α, IL-1β, TNF, IL-6, IL-8, IL-4, GM-CSF or IFN-γ,
e) shows no cytotoxicity to human peripheral blood mononuclear cells or lymphocytes; and
f) is not an endotoxin.

The BD-BRM composition can be prepared as described in International Patent Application Nos. WO 95/07089, WO 96/28175 and WO 02/38164 and U.S. Pat. Nos. 6,280,774 and 6,596,319. The BD-BRM composition can be characterised by evaluation of its known immunomodulatory properties, i.e. the ability to stimulate monocytes and macophages in vitro and in vivo, and the ability to modulate tumour necrosis factor production and/or release as described previously (see U.S. Pat. Nos. 6,280,774 and 6,596,319). More recent studies have indicated that the BD-BRM composition may mediate its anti-tumour activity through the stimulation of a sustained expansion and infiltration of natural killer (NK) cells and macrophages into tumours with subsequent activation of NK cells (Cao M. Y., et al. (2005) *Cancer Immunol Immunother.* 54:229-42. (Epub 2004 Sep. 17)].

Several Phase I and Phase II clinical studies have demonstrated that the BD-BRM composition has antitumour activity against pancreatic cancer and melanoma, and to have a clinical effect on disease stabilization and survival in patients with pancreatic cancer and malignant melanoma (Ferdinandi et al., (1999) *Exp Opin Invest Drugs* 8: 1721-1735; and Liu et al., (2000) *Drugs of the Future* 25: 356-359).

In addition to having specific or non-specific targets, immunotherapeutic agents can be active, i.e. stimulate the body's own immune response, or they can be passive, i.e. comprise immune system components that were generated external to the body. Both types of immunotherapeutic agents are suitable for use with interleukin 17E in the combination therapies of the present invention.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22.

Monoclonal antibodies are used in the treatment of a wide range of cancers including lymphomas (such as non-Hodgkin's lymphoma, B cell chronic lymphocytic leukemia (B-CLL)), myelomas (such as multiple myeloma), leukemias (such as B cell leukemia or acute myelogenous leukemia), breast cancer (including advanced metastatic breast cancer), colorectal cancer (including advanced and/or metastatic colorectal cancer), ovarian cancer, lung cancer, prostate cancer, cervical cancer, melanoma and brain tumours. Monoclonal antibodies can be used alone or in combination with other immunotherapeutic agents or chemotherapeutic agents.

Active specific immunotherapy typically involves the use of cancer vaccines. Cancer vaccines have been developed that comprise whole cancer cells, parts of cancer cells or one or more antigens derived from cancer cells. Cancer vaccines, alone or in combination with one or more immuno- or chemotherapeutic agents are being investigated in the treatment of several types of cancer including melanoma, renal cancer, ovarian cancer, breast cancer, colorectal cancer, lung cancer and leukemia. Non-specific immunotherapeutics are useful in combination with cancer vaccines in order to enhance the body's immune response.

In one embodiment of the present invention, interleukin 17E is used in combination with one or more immunotherapeutics for the treatment of cancer. In another embodiment, interleukin 17E is used in combination with one or more specific immunotherapeutics. In another embodiment, interleukin 17E is used in combination with a monoclonal antibody. In another embodiment, interleukin 17E is used in combination with one or more non-specific non-cytokine immunotherapies for the treatment of cancer.

Efficacy of Interleukin 17E

The anticancer efficacy of interleukin 17E can be tested in vitro and in vivo using standard techniques known in the art. In the context of the present invention, the interleukin 17E is considered to demonstrate an anticancer efficacy when it inhibits proliferation of neoplastic cells and/or inhibits tumour growth. A worker skilled in the art would readily appreciate that both in vitro and in vivo testing may be required in order to confirm the anticancer activity of an interleukin 17E polypeptide and that a failure to demonstrate an anti-proliferative effect in a particular in vitro assay may not be indicative of a lack of anti-proliferative activity in other in vitro assays or in vivo. For example, some interleukin 17E polypeptides fail to demonstrate anti-proliferative activity in vitro when the XTT assay is used, but demonstrate anticancer activity in vivo. Accordingly, the ability of a candidate interleukin 17E to exert an anticancer effect may need to be tested in more that one type of assay.

In Vitro Testing

Initial determinations of the efficacy of the interleukin 17E can be made using one or more standard in vitro assays. For example, the ability of interleukin 17E to inhibit proliferation of neoplastic cells can be assayed in vitro using a suitable cancer cell line. In general, cells of the selected test cell line are grown to an appropriate density and the candidate compound is added. After an appropriate incubation time (for example, about 48 to 72 hours), cell survival is assessed. Methods of determining cell survival are well known in the art and include, but are not limited to, the resazurin reduction test (see Fields & Lancaster (1993) *Am. Biotechnol. Lab.* 11:48-50; O'Brien et al., (2000) *Eur. J. Biochem.* 267:5421-5426 and U.S. Pat. No. 5,501,959), the sulforhodamine assay (Rubinstein et al., (1990) *J. Natl. Cancer Inst.* 82:113-118), the neutral red dye test (Kitano et al., (1991) *Euro. J. Clin. Investg.* 21:53-58; West et al., (1992) *J. Investigative Derm.* 99:95-100) or the XTT assay. Comparison of cell survival in the treated culture with cell survival in one or more control cultures, for example, untreated cultures and/or cultures pre-treated with a control compound (typically a known therapeutic), provides an indication of the ability of the candidate interleukin 17E to inhibit proliferation of the cells.

Alternatively, interleukin 17E can be tested in vitro by determining its ability to inhibit anchorage-independent growth of tumour cells. Anchorage-independent growth is known in the art to be a good indicator of tumourigenicity. In general, anchorage-independent growth is assessed by plating cells from a selected cancer cell-line onto soft agar and determining the number of colonies formed after an appropriate incubation period. Growth of cells treated with interleukin 17E can then be compared with that of control cells (as described above).

A variety of cancer cell-lines suitable for testing interleukin 17E in accordance with the invention are known in the art and many are commercially available (for example, from the American Type Culture Collection, Manassas, Va.). In one embodiment of the present invention, in vitro testing of interleukin 17E is conducted in a human cancer cell-line. Examples of suitable cancer cell-lines for in vitro testing include, but are not limited to, mesothelial cell lines MSTO-211H, NCI-H2052 and NCI-H28, ovarian cancer cell-lines OV90 and SK-OV-3, breast cancer cell-lines MCF-7 and MDA-MB-231, colon cancer cell-lines CaCo, HCT116 and H1299, cervical cancer cell-line HeLa, non-small cell lung carcinoma cell-lines A549 and H1299, pancreatic cancer cell-lines MIA-PaCa-2 and AsPC-1, prostatic cancer-cell line PC-3, bladder cancer cell-line T24, liver cancer cell-line HepG2, brain cancer cell-line U-87 MG, melanoma cell-line A2058, lung cancer cell-line NCI-H460. Other examples of suitable cell-lines are known in the art.

If necessary, the toxicity of interleukin 17E can also be initially assessed in vitro using standard techniques. For example, human primary fibroblasts can be transfected in vitro with interleukin 17E and then tested at different time points following treatment for their viability using a standard viability assay, such as the assays described above, or the trypan-blue exclusion assay. Cells can also be assayed for their ability to synthesize DNA, for example, using a thymidine incorporation assay, and for changes in cell cycle dynamics, for example, using a standard cell sorting assay in conjunction with a fluorocytometer cell sorter (FACS).

In Vivo Testing

The ability of interleukin 17E to inhibit tumour growth or proliferation of neoplastic cells in vivo can be determined in an appropriate animal model using standard techniques known in the art (see, for example, Enna, et al., *Current Protocols in Pharmacology*, J. Wiley & Sons, Inc., New York, N.Y.). Tumour growth may be inhibited by directly or indirectly killing neoplastic cells, inhibiting neoplastic cell growth, inhibiting neoplastic cell proliferation or a combination thereof. The effect of interleukin 17E on tumour growth may be cytotoxic or cytostatic, and may result in an overall reduction in the size of the tumour or in a slowing or prevention of an increase in the size of the tumour.

Current animal models for screening anti-tumour compounds include xenograft models, in which a human tumour has been implanted into an animal. Examples of xenograft models of human cancer include, but are not limited to, human solid tumour xenografts, implanted by sub-cutaneous injection or implantation and used in tumour growth assays; human solid tumour isografts, implanted by fat pad injection and used in tumour growth assays; human solid tumour orthotopic xenografts, implanted directly into the relevant tissue and used in tumour growth assays; experimental models of lymphoma and leukaemia in mice, used in survival assays, and experimental models of lung metastasis in mice. In addition to the implanted human tumour cells, the xenograft models can further comprise transplanted human peripheral blood leukocytes, which allow for evaluation of the anti-cancer immune response.

Alternatively, murine cancer models can be used for screening anti-tumour compounds. Examples of appropriate murine cancer models are known in the art and include, but are not limited to, implantation models in which murine cancer cells are implanted by intravenous, subcutaneous, fat pad or orthotopic injection; murine metastasis models; transgenic mouse models; and knockout mouse models.

For example, the effect of interleukin 17E can be tested in vivo on solid tumours using mice that are subcutaneously grafted bilaterally with 30 to 60 mg of a tumour fragment, or implanted with an appropriate number of cancer cells, on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. The interleukin 17E can be administered to the animals, for example, by i.p. injection or bolus infusion. The different animal groups are weighed about 3 or 4 times a week until the maximum weight loss is attained, after which the groups are weighed at least once a week until the end of the trial.

The tumours are measured after a pre-determined time period, or they can be monitored continuously by measuring about 2 or 3 times a week until the tumour reaches a pre-determined size and/or weight, or until the animal dies if this occurs before the tumour reaches the pre-determined size/weight. The animals are then sacrificed and the tissue histology, size and/or proliferation of the tumour assessed.

For the study of the effect of interleukin 17E on leukaemias, the animals are grafted with a particular number of cells, and the anti-tumour activity is determined by the increase in the survival time of the treated mice relative to the controls.

To study the effect of interleukin 17E on tumour metastasis, tumour cells may be injected into a suitable test animal which is then treated with interleukin 17E. Alternatively, the tumour cells may be treated ex vivo with interleukin 17E and then injected into a suitable test animal. The spread of the tumour cells from the site of injection is then monitored over a suitable period of time.

In vivo toxic effects of interleukin 17E can be evaluated by measuring its effect on animal body weight during treatment and by performing haematological profiles, pathology studies and liver enzyme analysis after the animal has been sacrificed.

TABLE 2

Examples of xenograft models of human cancer

| Cancer Model | Cell Type |
|---|---|
| Tumour Growth Assay Human solid tumour xenografts in mice (sub-cutaneous injection) | Prostate (PC-3, DU145) Breast (MDA-MB-231, MVB-9) Colon (HT-29) Lung (NCI-H460, NCI-H209) Pancreatic (ASPC-1, SU86.86) Pancreatic: drug resistant (BxPC-3) Skin (A2058, C8161) Cervical (SIHA, HeLa-S3) Cervical: drug resistant (HeLa S3-HU-resistance)Liver (HepG2) Brain (U87-MG) Renal (Caki-1, A498) Ovary (SK-OV-3) |
| Tumour Growth Assay Human solid tumour isografts in mice (fat pad injection) | Breast: drug resistant (MDA-CDDP-S4, MDA-MB435-To.1) |
| Survival Assay Experimental model of lymphoma and leukaemia in mice | Human: Burkitts lymphoma (Non-Hodgkin's) (raji) Murine: erythroleukemia (CB7 Friend retrovirus-induced) |
| Experimental model of lung metastasis in mice | Human: melanoma (C8161) Murine: fibrosarcoma (R3) |

Efficacy of Interleukin 17E in Combination with One or More Anticancer Therapeutics As indicated above, the present invention contemplates the use of interleukin 17E in combination with one or more anticancer therapeutics as part of a combination therapy regimen for the treatment of cancer. The efficacy of the combinations of interleukin 17E and one or more anticancer therapeutics can be tested using standard techniques including those outlined above for interleukin 17E alone. Additional controls may be included in such assays, such as cells treated with interleukin 17E alone and/or the anticancer therapeutic(s) alone in order to determine whether the effect of the combination is greater than the effect of the interleukin 17E and/or the anticancer therapeutic alone.

In one embodiment of the present invention, the use of a combination comprising interleukin 17E with one or more anticancer therapeutics is more effective than each of the components when used alone. Improved efficacy can be manifested, for example, as a less-than-additive effect, wherein the effect of the combination is greater than the effect of each component alone, but less than the sum of the effects of the components, or it may be an additive effect, wherein the effect of the combination is equivalent to the sum of the effects of the components when used individually, or it may be a more-than-additive effect, wherein the effect of the combination is greater than the sum of the effects of each component used alone. Greater than additive effects may also be described as synergistic.

Such improved efficacy can result in an increase in the ability of the combination to inhibit tumour growth or the proliferation of neoplastic cells when compared to the effect of each component alone and/or in lower doses of one or more of the components being required to bring about a certain effect (i.e. a decrease in the median effective dose or $ED_{50}$), and/or decreased toxicity phenomena associated with one or more of the components (i.e. an increase in the median lethal dose or $LD_{50}$). The improved efficacy can also result in an improved therapeutic index or clinical therapeutic index of the combination when compared to the therapeutic index/clinical therapeutic index of each component alone.

As used herein, the term "therapeutic index" is defined as $LD_{50}/ED_{50}$, where "$ED_{50}$" is the amount of a compound that produces 50% of the maximum response or effect associated with the compound, or the amount that produces a pre-determined response or effect in 50% of a test population, and "$LD_{50}$" is the amount of a compound that has a lethal effect in 50% of a test population. Thus, a compound with a high therapeutic index can typically be administered with greater safety than one with a low therapeutic index. The $LD_{50}$ is determined in preclinical trials, whereas the $ED_{50}$ can be determined in preclinical or clinical trials. Preclinical trials are conducted using an appropriate animal model, such as those described herein. The therapeutic index can also be determined based on doses that produce a therapeutic effect and doses that produce a toxic effect (for example, the $ED_{90}$ and $LD_{10}$, respectively).

"Clinical therapeutic index" differs from the definition of therapeutic index in that some indices of relative safety or relative effectiveness in patients in a clinical setting cannot be defined explicitly and uniquely. A combination is considered to demonstrate an improved Clinical Therapeutic Index, therefore, when it meets one of the following criteria as defined by the Food and Drug Administration: demonstrates increased safety (or patient acceptance) at an accepted level of efficacy within the recommended dosage range, or demonstrates increased efficacy at equivalent levels of safety (or patient acceptance) within the recommended dosage range, as compared to each of the components in the combination. Alternatively, during clinical studies, the dose or the concentration (for example, in solution, blood, serum, plasma) of a drug required to produce toxic effects can be compared to the concentration required to achieve the desired therapeutic effects in the population in order to evaluate the clinical therapeutic index. Methods of clinical studies to evaluate the clinical therapeutic index are well known to workers skilled in the art.

In one embodiment of the present invention, the use of a combination comprising interleukin 17E and one or more anticancer therapeutics results in therapeutic synergy, wherein "therapeutic synergy" is demonstrated when a combination is therapeutically superior to one of the components of the combination when used at that component's optimum dose [as defined in T. H. Corbett et al., (1982) *Cancer Treatment Reports,* 66:1187]. To demonstrate the efficacy of a combination, it may be necessary to compare the maximum tolerated dose of the combination with the maximum tolerated dose of each of the separate components in the study in question. This efficacy may be quantified using techniques and equations commonly known to workers skilled in the art [see, for example, T. H. Corbett et al., (1977) *Cancer,* 40, 2660.2680; F. M. Schabel et al., (1979) Cancer Drug Development, Part B, *Methods in Cancer Research,* 17:3-51, New York, Academic Press Inc.].

Pharmaceutical Compositions

The present invention provides for pharmaceutical compositions comprising interleukin 17E and optionally one or more anticancer therapeutics and one or more non-toxic pharmaceutically acceptable carriers, diluents, excipients and/or adjuvants.

If desired, other active ingredients may be included in the compositions. As indicated above, such compositions are used in the treatment of various cancers in a subject, including a human.

The pharmaceutical compositions can be formulated for administration by a variety of routes. For example, the compositions can be formulated for oral, topical, rectal or parenteral administration or for administration by inhalation or spray. The term parenteral as used herein includes subcutaneous injections, intravenous, intramuscular, intrathecal, intrasternal injection or infusion techniques.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed.

Pharmaceutical compositions for oral use can also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-β-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavouring agents or one or more sweetening agents, such as sucrose or saccharin.

Pharmaceutical compositions can be formulated as oily suspensions by suspending the active compound(s) in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above. Additional excipients, for example, sweetening, flavouring and colouring agents, can also be included in these compositions.

Pharmaceutical compositions of the invention can also be formulated as oil-in-water emulsions. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions can also optionally contain sweetening and flavouring agents.

Pharmaceutical compositions can be formulated as a syrup or elixir by combining the active ingredient(s) with one or more sweetening agents, for example glycerol, propylene glycol, sorbitol or sucrose. Such formulations can also optionally contain one or more demulcents, preservatives, flavouring agents and/or colouring agents.

The pharmaceutical compositions can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, Pa. (2000).

The pharmaceutical compositions of the present invention described above include interleukin 17E and optionally one or more anticancer therapeutics in an amount effective to achieve the intended purpose. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other mammals, including humans using standard methods known in those of ordinary skill in the art.

Uses

The present invention contemplates the use of interleukin 17E to treat, stabilize or prevent cancer. In this context, interleukin 17E may exert either a cytotoxic or cytostatic effect resulting in a reduction in the size of a tumour, the slowing or prevention of an increase in the size of a tumour, an increase in the disease-free survival time between the disappearance or removal of a tumour and its reappearance, prevention of an initial or subsequent occurrence of a tumour (e.g. metastasis), an increase in the time to progression, reduction of one or more adverse symptom associated with a tumour, or an increase in the overall survival time of a subject having cancer. Interleukin 17E can be used alone or in combination with one or more anticancer therapeutics.

Accordingly, one embodiment of the present invention provides for the use of interleukin 17E alone for the treatment of cancer. Another embodiment of the present invention provides for the use of interleukin 17E in combination with one or more anti-cancer therapeutic for the treatment of cancer. Another embodiment of the present invention provides for the use of interleukin 17E in combination with one or more immunotherapeutics, one or more chemotherapeutics, or a combination thereof, for the treatment of cancer. Another embodiment of the present invention provides the use of interleukin 17E in combination with one or more non-specific immunotherapeutics for the treatment of cancer. Another embodiment of the present invention provides for the use of interleukin 17E in combination with BD-BRM for the treatment of cancer.

Examples of cancers which may be may be treated in accordance with the present invention include, but are not limited to haematologic neoplasms, including leukaemias and lymphomas; carcinomas, including adenocarcinomas; melanomas and sarcomas. Carcinomas, adenocarcinomas and sarcomas are also frequently referred to as "solid tumours." Examples of commonly occurring solid tumours include, but are not limited to, cancer of the brain, breast, cervix, colon, head and neck, kidney, lung, ovary, pancreas, prostate, stomach and uterus, non-small cell lung cancer and colorectal cancer. Various forms of lymphoma also may result in the formation of a solid tumour and, therefore, are also often considered to be solid tumours.

The term "leukaemia" refers broadly to progressive, malignant diseases of the blood-forming organs. Leukaemia is typically characterized by a distorted proliferation and development of leukocytes and their precursors in the blood and bone marrow but can also refer to malignant diseases of other blood cells such as erythroleukaemia, which affects immature red blood cells. Leukaemia is generally clinically classified on the basis of (1) the duration and character of the disease—acute or chronic; (2) the type of cell involved—myeloid (myelogenous), lymphoid (lymphogenous) or monocytic, and (3) the increase or non-increase in the number of abnormal cells in the blood—leukaemic or aleukaemic (subleukaemic). Leukaemia includes, for example, acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, aleukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "sarcoma" generally refers to a tumour which originates in connective tissue, such as muscle, bone, cartilage or fat, and is made up of a substance like embryonic connective tissue and is generally composed of closely packed cells embedded in a fibrillar or homogeneous substance. Sarcomas include soft tissue sarcomas, chondrosarcoma, fibrosarcoma, lymphosarcoma, melano sarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented haemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colorectal carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, non-small cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "carcinoma" also encompasses adenocarcinomas. Adenocarcinomas are carcinomas that originate in cells that make organs which have glandular (secretory) properties or that originate in cells that line hollow viscera, such as the gastrointestinal tract or bronchial epithelia. Examples include, but are not limited to, adenocarcinomas of the breast, lung, colon, pancreas and prostate.

Additional cancers encompassed by the present invention include, for example, Hodgkin's Disease, Non-Hodgkin's lymphoma, multiple myeloma, neuroblastoma, rhabdomyosarcoma, primary thrombocytosis, primary macroglobulinemia, small-cell lung tumours, primary brain tumours, malignant pancreatic insulanoma, malignant carcinoid, urinary bladder cancer, premalignant skin lesions, gliomas, testicular cancer, thyroid cancer, esophageal cancer, genitourinary tract cancer, malignant hypercalcemia, endometrial cancer, adrenal cortical cancer, mesothelioma and medulloblastoma.

One embodiment of the present invention provides for the use of interleukin 17E alone or in combination with one or more anticancer therapeutics in the treatment of a solid tumour. Another embodiment of the present invention provides for the use of interleukin 17E alone or in combination with one or more anticancer therapeutics in the treatment of a solid tumour which is a peritoneal or gyneological malignancy. Another embodiment of the present invention provides for the use of interleukin 17E alone or in combination with one or more anticancer therapeutics in the treatment of a solid tumour selected from the group consisting of breast cancer, prostate cancer, pancreatic cancer, melanoma, ovarian cancer, ear, nose and throat (ENT) cancer, endometrial cancer, lung cancer, colon and Kaposi's sarcoma.

As interleukin 17E induced eosinophil recruitment and infiltration is particularly effective in mucosal tissues, one embodiment of the present invention contemplates the use of interleukin 17E for the treatment of cancers associated with mucosal tissue. In another embodiment, the present invention contemplates the use of interleukin 17E for the treatment of other cancers susceptible to eosinophil infiltration including but not limited to colon cancer, breast cancer, ovarian cancer, cervical cancer, endometrial cancer, lung cancer, gastric cancer, oral cancer, oesophageal cancer, prostate cancer and Hodgkin's disease.

One embodiment of the present invention provides for the use of interleukin 17E alone, or in combination with one or more anticancer therapeutics, in the treatment of melanoma. Another embodiment of the present invention provides for the use of interleukin 17E alone or in combination with one or more anticancer therapeutics in the treatment of pancreatic cancer. Another embodiment of the present invention provides for the use of interleukin 17E alone or in combination with one or more anticancer therapeutics in the treatment of ovarian cancer. Another embodiment of the present invention provides for the use of interleukin 17E alone or in combination with one or more anticancer therapeutics in the treatment of lung cancer. Another embodiment of the present invention provides for the use of interleukin 17E alone or in combination with one or more anticancer therapeutics in the treatment of colon cancer. In another embodiment of the present invention, the one or more anticancer therapeutics is one or more immunotherapeutics, one or more chemotherapeutics or a combination thereof.

In accordance with the present invention, interleukin 17E alone, or in combination with one or more anticancer therapeutics, can be used to treat various stages and grades of cancer development and progression. The present invention, therefore, contemplates the use of interleukin 17E alone, or in combination with one or more anticancer therapeutics, in the treatment of early stage cancers including early neoplasias that may be small, slow growing, localized and/or nonaggressive, for example, with the intent of curing the disease or causing regression of the cancer, as well as in the treatment of intermediate stage and in the treatment of late stage cancers including advanced and/or metastatic and/or aggressive neoplasias, for example, to slow the progression of the disease, to reduce metastasis or to increase the survival of the patient. Similarly, interleukin 17E alone, or in combination with one or more anticancer therapeutics, may be used in the treatment of low grade cancers, intermediate grade cancers and or high grade cancers.

The present invention also contemplates that interleukin 17E alone, or in combination with one or more anticancer therapeutics, can be used in the treatment of indolent cancers, recurrent cancers including locally recurrent, distantly recurrent and/or refractory cancers (i.e. cancers that have not responded to treatment), metastatic cancers, locally advanced cancers and aggressive cancers. Thus, an "advanced" cancer includes locally advanced cancer and metastatic cancer and refers to overt disease in a patient, wherein such overt disease is not amenable to cure by local modalities of treatment, such as surgery or radiotherapy. The term "metastatic cancer" refers to cancer that has spread from one part of the body to another. Advanced cancers may also be unresectable, that is, they have spread to surrounding tissue and cannot be surgically removed.

One skilled in the art will appreciate that many of these categories may overlap, for example, aggressive cancers are typically also metastatic. "Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, such as small cell lung carcinoma (SCLC) nearly all cases present rapidly growing cancers which are considered to be aggressive. The term can thus cover a subsection of a certain cancer type or it may encompass all of other cancer types.

Interleukin 17E alone, or in combination with one or more anticancer therapeutics, may also be used to treat drug resistant cancers, including multidrug resistant tumours. As is known in the art, the resistance of cancer cells to chemotherapy is one of the central problems in the management of cancer.

Certain cancers, such as prostate and breast cancer, can be treated by hormone therapy, i.e. with hormones or anti-hormone drugs that slow or stop the growth of certain cancers by blocking the body's natural hormones. Such cancers may develop resistance, or be intrinsically resistant, to hormone therapy. The present invention further contemplates the use of interleukin 17E alone, or in combination with one or more anticancer therapeutics, in the treatment of such "hormone-resistant" or "hormone-refractory" cancers.

The present invention contemplates the use of interleukin 17E alone, or in combination with one or more anticancer therapeutics, as part of a primary therapy or an adjuvant therapy. "Primary therapy" or "first-line therapy" refers to treatment upon the initial diagnosis of cancer in a subject. Exemplary primary therapies may involve surgery, a wide range of chemotherapies, immunotherapy and radiotherapy. When first-line or primary therapy is not systemic chemotherapy or immunotherapy, then subsequent chemotherapy or immunotherapy may be considered as "first-line systemic therapy." In one embodiment of the present invention, interleukin 17E alone or in combination with one or more anticancer therapeutics is used for first-line systemic therapy.

"Adjuvant therapy" refers to a therapy that follows a primary therapy and that is administered to subjects at risk of relapsing. Adjuvant systemic therapy is typically begun soon after primary therapy to delay recurrence, prolong survival or cure a subject. Treatment of a refractory cancer may be termed a "second-line therapy" and is a contemplated use of the present invention, in addition to first-line therapy.

The present invention further contemplates the use of interleukin 17E as a "sensitizing agent," which selectively inhibits the growth of cancer cells. In this case, interleukin 17E does not have a cytotoxic effect on the cancer cell, but provides a means of weakening the cancer cells, and thereby facilitates the benefit from conventional anti-cancer therapeutics.

As indicated above and shown in the Examples provided herein, interleukin 17E is capable of exerting its anti-cancer effects in the absence of a T-cell response. As such, the present invention contemplates the use of interleukin 17E in immunocompromised subjects, such as those with a reduced level of T-cells or T-cell function. Accordingly, the present invention contemplates the use of interleukin 17E to cancer patients with varying levels of immunocompetence. For example, it is well known in the art that cancer patients may have suppressed immune systems. Similarly, AIDS patients and other immunocompromised patients can be susceptible to cancer. One embodiment of the present invention, therefore, provides for the use of interleukin 17E to treat cancer in immunocompromised, immune suppressed or immuno-incompetent patients.

Administration

Interleukin 17E may be administered to a subject by a variety of routes including orally, topically, parenterally, by inhalation or spray, or rectally/vaginally in dosage unit formulations. The term parenteral as used herein includes subcutaneous injections, intravenous, intramuscular, intrathecal, intrasternal injection or infusion techniques. In one embodiment, interleukin 17E is administered systemically to a subject, for example, by bolus injection or infusion into a subject's bloodstream or by oral administration. When interleukin 17E is used in conjunction with one or more anticancer therapeutics, interleukin 17E can be administered prior to, or after, administration of the anticancer therapeutic(s), or they can be administered concomitantly. A worker skilled in the art would readily appreciate that the routes by which the anticancer therapeutic(s) can be administered will depend on which anticancer therapeutic is used. For example, the anticancer therapeutic(s) may be administered parenterally, by inhalation, or by oral administration. Appropriate routes of administration, doses and treatment regimens for standard anticancer therapeutics are known in the art.

The present invention also contemplates that a polynucleotide encoding interleukin 17E can be directly administered in vivo, where it is expressed to produce the encoded interleukin 17E polypeptide. Methods for expressing polypeptides in vivo are known in the art. For example, a "naked" nucleic acid molecule (polynucleotide) can be directly injected (Felgner and Rhodes, (1991) Nature 349:351-352; U.S. Pat. No. 5,679,647) or by injection of a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis (see, for example, Wu and Wu, (1987) J. Biol. Chem. 262:4429-4432), which can be used to target cell types specifically expressing the receptors. Alternatively, a nucleic acid-ligand complex can be formed in which the ligand comprises a fusogenic viral peptide to disrupt endosomes, allowing the nucleic acid to avoid lysosomal degradation; or the nucleic acid molecule can be targeted in vivo for cell specific uptake and expression by targeting a specific receptor (see, for example, International Patent Applications WO 92/06180, WO 92/22635, WO92/20316, WO93/14188 and WO 93/20221). The present invention also contemplates the intracellular introduction of the nucleic acid molecule and subsequent incorporation within host cell DNA for expression by homologous recombination (see, for example, Koller and Smithies (1989) Proc. Natl. Acad. Sci. USA 86:8932-8935; Zijlstra et al. (1989) Nature 342:435-438).

In one embodiment of the present invention, the anticancer therapeutic for use in combination with interleukin 17E is BD-BRM. Alternatively, BD-BRM can be used to stimulate production of endogenous interleukin 17E. The dose range and administration route for BD-BRM is known in the art. For example, BD-BRM may be administered by intramuscular, oral or intravenous administration. An appropriate dosage range for BD-BRM is from about 0.01 to 20 mg/kg of body weight daily. In the case of intravenous administration, an appropriate dosage of BD-BRM is about 0.05 to 1 mg/kg of body weight daily, and in the case of oral administration the dosage is about 1 to 5 mg/kg of body weight daily. For intramuscular administration, a dosage of about 0.05 to 0.2 mg/kg of body weight daily may be used.

The dosage of interleukin 17E to be administered is not subject to defined limits, but it will usually be an effective amount. The interleukin 17E may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. It will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms.

Clinical Trials in Cancer Patients

One skilled in the art will appreciate that, following the demonstrated effectiveness of interleukin 17E in vitro and in animal models, it should be submitted to standard GLP animal toxicology and pharmacokinetic studies and then be entered into Clinical Trials in order to further evaluate its efficacy in the treatment of cancer and to obtain regulatory approval for therapeutic use. As is known in the art, clinical trials progress through phases of testing, which are identified as Phases I, II, III, and IV.

Initially, the selected interleukin 17E will be evaluated in a Phase I trial, which is usually an open-label trial. Typically Phase I trials are used to determine the best mode of administration (for example, by pill or by injection), the frequency of administration, and the toxicity for the interleukin 17E polypeptide. Phase I studies frequently include laboratory tests, such as blood tests and biopsies, to evaluate the effects of interleukin 17E in the body of the patient. For a Phase I trial, a small group of cancer patients are treated with a specific dose of the interleukin 17E polypeptide. During the trial, the dose is typically increased group by group in order to determine the maximum tolerated dose (MTD) and the dose-limiting toxicities (DLT) associated with interleukin 17E. This process determines an appropriate dose to use in a subsequent Phase II trial.

A Phase II trial can be conducted to further evaluate the effectiveness and safety of interleukin 17E. Phase II trials are usually open-label, but may also be blinded. In Phase II trials, interleukin 17E is administered to groups of patients with either one specific type of cancer or with related cancers, using the dosage found to be effective in Phase I trials.

Phase III trials focus on determining how the selected interleukin 17E compares to the standard, or most widely accepted, treatment. Phase III trials are generally blinded. In Phase III trials, patients are randomly assigned to one of two or more "arms". In a trial with two arms, for example, one arm will receive the standard treatment (control group) and the other arm will receive interleukin 17E treatment (investigational group).

Phase IV trials are used to further evaluate the long-term safety and effectiveness of interleukin 17E. Phase IV trials are less common than Phase I, II and III trials and will take place after interleukin 17E has been approved for standard use.

Eligibility of Patients for Clinical Trials

Participant eligibility criteria can range from general (for example, age, sex, type of cancer) to specific (for example, type and number of prior treatments, tumour characteristics, blood cell counts, organ function). Eligibility criteria may also vary with trial phase. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I cancer trials usually comprise 15 to 30 participants for whom other treatment options have not been effective. Phase II trials typically comprise up to 100 participants who have already received chemotherapy, surgery, or radiation treatment, but for whom the treatment has not been effective. Participation in Phase II trials is often restricted based on the previous treatment received. Phase III trials usually comprise hundreds to thousands of participants. This large number of participants is necessary in order to determine whether there are true differences between the effectiveness of the therapy under evaluation and the standard treatment. Phase III may comprise patients ranging from those newly diagnosed with cancer to those with extensive disease in order to cover the disease continuum.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

Assessment of Patients Prior to Treatment

Prior to commencement of the study, several measures known in the art can be used to first classify the patients. Patients can first be assessed, for example, using the Eastern Cooperative Oncology Group (ECOG) Performance Status (PS) scale. ECOG PS is a widely accepted standard for the assessment of the progression of a patient's disease as measured by functional impairment in the patient, with ECOG PS 0 indicating no functional impairment, ECOG PS 1 and 2 indicating that the patients have progressively greater functional impairment but are still ambulatory and ECOG PS 3 and 4 indicating progressive disablement and lack of mobility.

Patients' overall quality of life can be assessed, for example, using the McGill Quality of Life Questionnaire (MQOL) (Cohen et al (1995) *Palliative Medicine* 9: 207-219). The MQOL measures physical symptoms; physical, psychological and existential well-being; support; and overall quality of life. To assess symptoms such as nausea, mood, appetite, insomnia, mobility and fatigue the Symptom Distress Scale (SDS) developed by McCorkle and Young ((1978) *Cancer Nursing* 1: 373-378) can be used.

Patients can also be classified according to the type and/or stage of their disease and/or by tumour size.

Pharmacokinetic Monitoring

To fulfil Phase I criteria, distribution of the candidate therapeutics are monitored, for example, by chemical analysis of samples, such as blood or urine, collected at regular intervals. For example, samples can be taken at regular intervals up until about 72 hours after the start of infusion.

If analysis is not conducted immediately, the samples can be placed on dry ice after collection and subsequently transported to a freezer to be stored at $-70°$ C. until analysis can be conducted. Samples can be prepared for analysis using standard techniques known in the art.

Pharmacokinetic data can be generated and analyzed in collaboration with an expert clinical pharmacologist and used to determine, for example, clearance, half-life and maximum plasma concentration.

Monitoring of Patient Outcome

The endpoint of a clinical trial is a measurable outcome that indicates the effectiveness of a therapy under evaluation. The endpoint is established prior to the commencement of the trial and will vary depending on the type and phase of the clinical trial. Examples of endpoints include, for example, tumour response rate—the proportion of trial participants whose tumour was reduced in size by a specific amount, usually described as a percentage; disease-free survival—the amount of time a participant survives without cancer occurring or recurring, usually measured in months; overall survival—the amount of time a participant lives, typically measured from the beginning of the clinical trial until the time of death. For advanced and/or metastatic cancers, disease stabilization—the proportion of trial participants whose disease has stabilized, for example, whose tumour(s) has ceased to grow and/or metastasize, can be used as an endpoint. Other endpoints include toxicity and quality of life.

Tumour response rate is a typical endpoint in Phase II trials. However, even if a treatment reduces the size of a participant's tumour and lengthens the period of disease-free survival, it may not lengthen overall survival. In such a case, side effects and failure to extend overall survival might outweigh the benefit of longer disease-free survival. Alternatively, the participant's improved quality of life during the tumour-free interval might outweigh other factors. Thus, because tumour response rates are often temporary and may not translate into long-term survival benefits for the participant, response rate is a reasonable measure of a treatment's effectiveness in a Phase II trial, whereas participant survival and quality of life are typically used as endpoints in a Phase III trial.

Combination Products

The present invention further provides combination products comprising interleukin 17E, or a polynucleotide encoding interleukin 17E, in combination with one or more anti-cancer therapeutics.

The combination products of the present invention can comprise one or more compositions. For example, the combination product can be a single composition comprising interleukin 17E and one or more anti-cancer therapeutics. Alternatively, the combination products can comprise one composition comprising interleukin 17E and one or more additional compositions comprising the anticancer therapeutic(s). The present invention further contemplates that the compositions included in the combination product can be formulated for administration to the subject to be treated via the same or different routes. Similarly, the compositions included in the combination product can be formulated for sequential or concurrent administration to the subject.

In one embodiment of the present invention, there is provided a combination product comprising interleukin 17E, or a polynucleotide encoding interleukin 17E, in combination with one or more chemotherapeutics and/or one or more immunotherapeutics. In another embodiment of the present invention, there is provided a combination product comprising interleukin 17E, or a polynucleotide encoding interleukin 17E, in combination with one or more immunotherapeutics. In another embodiment of the present invention, there is provided a combination product comprising interleukin 17E, or a polynucleotide encoding interleukin 17E, in combination with one or more non-specific immunotherapeutic agents. In another embodiment of the present invention, there is provided a combination production comprising interleukin 17E, or a polynucleotide encoding interleukin 17E, in combination with BD-BRM.

Kits

The present invention additionally provides for therapeutic kits or packs containing interleukin 17E, or a polynucleotide encoding interleukin 17E, and optionally one or more anticancer therapeutics. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit may optionally contain instructions or directions outlining the method of use or dosing regimen for the interleukin 17E and optionally the one or more anticancer therapeutics.

When the components of the kit are provided in one or more liquid solutions, the liquid solution can be an aqueous solution, for example a sterile aqueous solution. In this case the container means may itself be an inhalant, syringe, pipette, eye dropper, or other such like apparatus, from which the composition may be administered to a patient or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or similar medically approved delivery vehicle.

The invention will now be described with reference to specific examples. It will be understood that the following examples are intended to describe embodiments of the invention and are not intended to limit the invention in any way.

EXAMPLES

Example 1

Identification IL-17E in Serum of Mice Treated with a BD-BRM Composition

Proteomic approaches were used to investigate the changes of protein expression in serum of tumour bearing mice treated with a BD-BRM composition.

Drugs:

BD-BRM was obtained from bovile bile (derived from U.S. cattle approximately 24 months of age; USDA inspected) by a standardized process including ethanol precipitation, column purification, heat reduction, ether extraction, and tyndallization, which remove most bile salts and large peptides. The BD-BRM composition contains 5% (w/v) solid material and is comprised of inorganic (95-99% of the dry weight) and organic compounds of molecular weights of <3000 Daltons (1-5% of the dry weight). BD-BRM is formulated as a sterile injectable solution, buffered with monobasic and dibasic sodium phosphate.

Cells and Animals:

Human melanoma cell line C8161 was grown in RPMI 1640 medium (Wisent Inc., St. Bruno, QC) with 10% fetal bovine serum, penicillin (100 U/ml), streptomycin (100 mg/ml) (Wisent Inc.) at 37° C. under 95% air and 5% $CO_2$, and maintained with routine media changes. Adherent C8161 cells were passaged by trypsinization with 0.025% trypsin. CD-1 athymic nude mice and C57BL/6 (6-8 weeks old, 20-25 g, female) were purchased from Charles River (Montreal, QC).

Evaluation of Antitumour Activity in a Murine Model of Human Tumour Xenograft:

Human tumour xenografts were established in mice. Briefly, human tumour cells were harvested at approximately 80% confluence in cell culture medium and resuspended in sterile PBS. Ten million tumour cells in 100 µl were subcutaneously implanted into the right flank of CD-1 athymic nude mice. When tumours reached a volume of 50-100 mm³, mice were randomly separated into two groups of 10 animals and treated with BD-BRM until the endpoint of the experiment. Anti-tumour activity was evaluated and tumour volume was estimated by caliper measurements, using the formula: Length×Width×Height×/2. Tumour weight was determined from tumour tissue surgically excised from the animal on the last day of the experiment. The percentage of inhibition (%)= (mean tumour weight of control animals−mean tumour weight of drug-treated group)/mean tumour weight of controls×100. A p value of $\leq 0.05$ was considered to be statistically significant.

Two-Dimensional (2-D) Gel Electrophoresis:

The serum collected from the mice was prepared with Aurum Serum Protein Mini Kit (Bio-Rad) to remove albumin and immunoglobulin according to the manufacturer's instruction. The resultant sample was diluted in ReadyPrep Rehydration/Sample Buffer (Bio-Rad) and was subjected to 2-D gel electrophoresis. First-dimension isoelectric focusing (IEF) was carried out on a Protean IEF cell system as described by the manufacturer (Bio-Rad Laboratories, Hercules, Calif.). Samples containing up to 20 µg of protein for analytical gels were diluted to up to 125 µl with dehydration solution (8 M urea, 2% CHAPS, 50 mM dithiothreitol, 0.2% (w/v) Bio-Lyte 4/7 ampholytes (Bio-Rad) and Bromophenol blue (trace). Pre-cast immobilized pH gradient (IPG) strip (7 cm, pH 4-7, linear gradient) (Bio-Rad) was used for the first-dimension separation. Strips were applied by overnight rehydration at 50 V. Then a gradient was applied from 250 V to 4000 V overnight. All IEF steps were carried out at 20° C. After the first-dimension IEF, IPG gel strips were placed in an equilibration solution (6 M urea, 2% SDS, 20% glycerol, 0.375 M Tris-HCl, pH 8.8) containing 2% (w/v) dithiothreitol and shaken for 10 minutes. The gels were then transferred to the equilibration solution containing 2.5% (w/v) iodoacetamide to alkylate thiols and shaken for a further 10 minutes before being placed on a 10% polyacrylamide gel slab. Separation in the second dimension was carried out using Tris-glycine buffer containing 10% SDS, at a current of 200 V for 40 minutes.

For silver staining, the gels were immersed in methanol: acetic acid:water (50:5:45) for 20 minutes followed by washing once in 50% methanol and once with deionized water for 10 minutes per wash. Gels were pretreated for 1 min in a solution of 2% $Na_2S_2O_3$ and followed by 3 washes of 1 min in deionized water. Proteins were stained with 0.1% silver nitrite for 20 min at 4° C., followed by 2 washes with deionized water for 1 min per wash. Gels were developed by incubation in 0.04% formalin (35% formaldehyde in water) in 2% sodium carbonate. When the desired intensity was attained, the developer was discarded and reaction stopped by 5% acetic acid. Protein patterns in the gel after silver staining were recorded as digitalized images using a high-resolution scanner. Gel image matching was done with Quantity One software (Bio-Rad).

Western Blot Analysis:

The serum sample was prepared as described above. Protein concentration in the lysates was quantified with a Bio-Rad protein assay kit using bovine serum albumin as the standard. Western blot was performed. Briefly, total protein lysates (40 µg/lane) were resolved on 10% SDS-polyacrylamide gels and protein transferred to polyvinylidene difluoride membranes. Blots were treated with blocking agent, 5% non-fat milk in Tris-buffered saline, for 1 h at room temperature. Protein expression was subsequently detected with primary antibodies against the different antigens. After washing with Tris-buffered saline/Tween 20, three times, a secondary antibody conjugated to horseradish peroxidase (Santa Cruz Biotechnology and Amersham Biosciences Inc., Piscataway, N.J.) at a dilution of 1:10,000 was added and incubated at room temperature for 1 h. The blots were washed and the immune complexes detected using an enhanced chemiluminescence detection reagent kit (Amersham Biosciences Inc.) and exposed to Kodak X-OMAT AR film for autoradiography.

Results:

Mice bearing human melanoma C8161 xenograft were treated intraperitoneally with BD-BRM or PBS for 4 weeks. Briefly, human melanoma C8161 cells were subcutaneously injected into the right flank of CD-1 nude mice as described above. The mice were then administered i.p. with 0.2 ml of PBS or BD-BRM daily when tumours reached a volume of 50-100 mm$^3$. BD-BRM significantly inhibited tumour growth as compared to PBS group.

The sera were collected from the mice and analyzed by 2-D gel electrophoresis. FIG. 1 shows the silver-stained 2-D electrophoresis maps of sera from PBS-treated (FIG. 1A) or BD-BRM-treated (FIG. 1B) mice. The intensity of one particular spot was increased in the serum of BD-BRM-treated mice (circled in FIG. 1B) as compared to PBS-treated mice. This spot was subsequently excised from the gel and analyzed by MALDI-TOF after in-gel digestion. The protein was identified as mouse IL-17E.

The serum sample was also run on SDS-PAGE gel and transferred onto PVDF membrane that was probed by anti-mouse IL-17E antibody [anti-mouse IL-17E (207710; IgG2b) from R&D systems, (Birmingham, Ala.)]. As shown in FIG. 1C, an increased IL-17E was also identified in BD-BRM-treated mice with molecular weight approximately 23 Kd. The level of beta-actin on each lane was comparable, indicating equivalent amounts of serum loaded on the gels. The size of IL-17E on the Western blot is very similar to the spot detected on silver-stained 2-D gel

Example 2

Increased Level of IL-17E in Serum of Mice Treated with a BD-BRM Composition To confirm increased expression of IL-17E in mice following BD-BRM treatment, the sera were collected from mice in antitumour efficacy studies of BD-BRM as described in the previous example, and analyzed for IL-17E protein by ELISA. Briefly, human melanoma C8161 cells were subcutaneously injected into the right flank of CD-1 nude mice. The mice were then administered i.p. with 0.2 ml of PBS (n=8) or BD-BRM (n=9) daily when tumours reached a volume of 50-100 mm$^3$. At the end of experiment serum was collected from mice. IL-17E in the sera was determined by ELISA.

Figure 2:
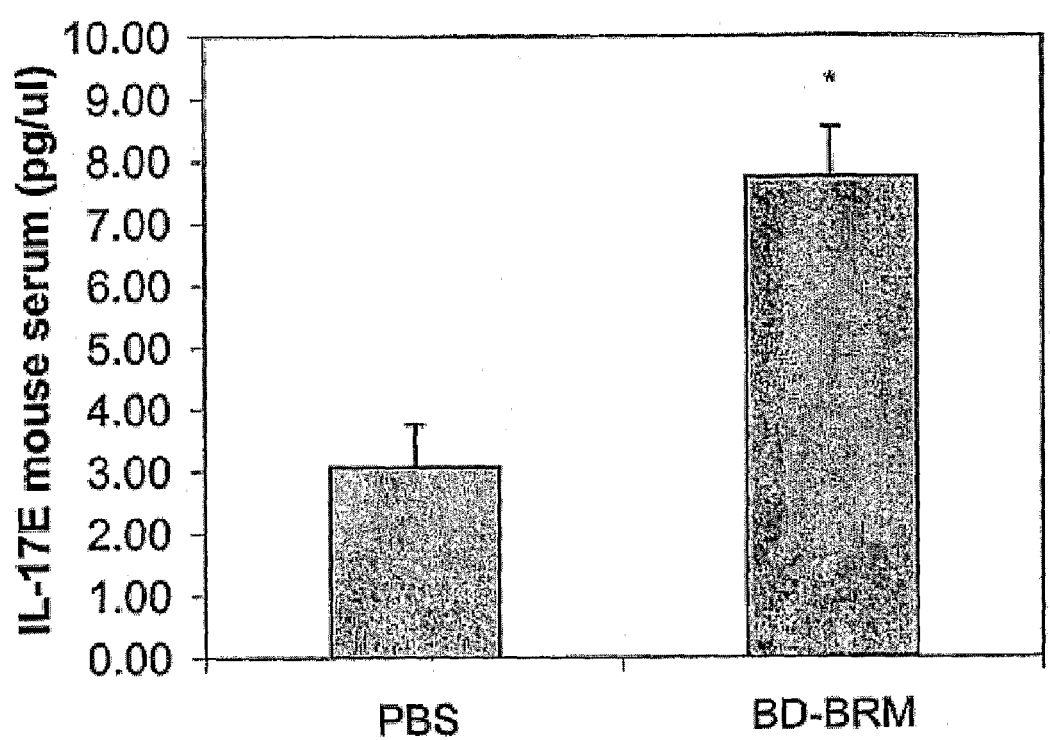
FIG. 2 depicts differences in interleukin 17E expression in sera from CD-1 nude mice bearing human melanoma tumour cells treated with a bile-derived biological response modifier (BD-BRM) composition or PBS.

As shown in FIG. 2, IL-17E was increased in the sera of BD-BRM-treated mice as compared to those in the PBS controls (p<0.001). The level of IL-17E was elevated from 3.07 pg/µl in PBS-treated mice to 7.73 pg/µl in BD-BRM-treated mice. The data represent 3 independent experiments.

Example 3

BD-BRM Composition Induces IL-17E from Spleen Cells In Vitro

Splenocytes isolated from mice treated with BD-BRM were evaluated to determine if BD-BRM was capable of directly inducing IL-17E from splenocytes.

Cell Isolation:

Single cell suspensions of spleen cells, from spleens of C57BL/6 mice, were obtained by meshing and passing through a cell strainer (70 µm; Bectin Dickinson) to separate fibrous tissue. Erythrocytes were lysed with ACK (0.155 M ammonium chloride, 0.1 mM disodium EDTA, 0.01 M potassium bicarbonate, pH 7.3) for 5 minutes on ice.

In Vitro Stimulation:

Cells were isolated from C57BL/6 mice. Approximately 2×10$^7$ cells/well were plated in triplicate in 6 well tissue culture plates after red blood cell lysis. The cells were treated with or without 5% BD-BRM for various time paints as indicated. At each time point, adherent and nonadherent cells were harvested and pooled for further analysis.

Reverse Transcription-Polymerase Chain Reaction (RT-PCR):

For RT-PCR, RNA was isolated using TRIZOL (Invitrogen, Burlington, ON). Total RNA (2-4 µg) was treated with DNase I to remove any contaminating genomic DNA, and then reverse transcribed into cDNA using 200 units of Superscript II reverse transcriptase (Invitrogen) in the presence of oligonucleotides (dT)$_{12-18}$ according to manufacturer's instructions. Amplification of each target cDNA was performed with JumpStart™ Taq PCR kits (Sigma-Aldrich, St. Louis, Mo.) in the ABI PRISM 7900HT sequence detection system according to the protocols provided by the manufacturer (Applied Biosystems, Foster City, Calif.). PCR products were quantified fluorometrically using SYBR Green (Bio-Rad, Mississauga, ON). Beta actin expression in each sample was used as a control. Two different primer sets were designed and synthesized for each investigated gene using Primer Express version 2.0 (Applied Biosystems). A standard curve of each primer set was generated using mouse genomic DNA. One primer set was chosen for each gene to perform all the subsequent PCR to ensure better PCR efficiency and standard curve lineage. The primer sets utilized were as follows:

```
                                           [SEQ ID NO: 9]
β-actin forward: TGG CTG AGG ACT TTG TAC ATT GTT

[SEQ ID NO: 10]
β-actin reverse: GGG ACT TCC TGT AAC CAC TTA TTT CA

[SEQ ID NO: 11]
IL-17E forward: TGC TGC CCC AGC AAA GAG

[SEQ ID NO: 12]
IL-17E reverse: GAC ACA GAT GCA GAG CTC CAC TT.
```

Figure 3:
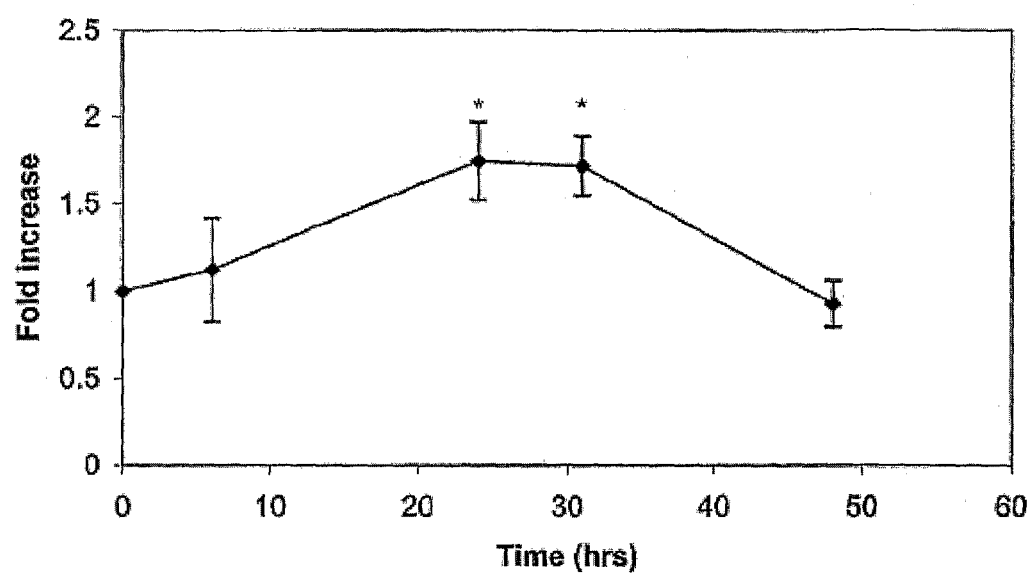
FIG. 3 depicts expression of interleukin 17E in splenocytes isolated from C57BL/6 mice treated with a bile-derived biological response modifier (BD-BRM) composition in vitro relative to splenocytes treated with PBS.

Results:

Expression of IL-17E in splenocytes from normal (C57BL/6) mice treated in vitro with BD-BRM for various time periods, was evaluated at each time point and examined by real-time PCR as described above. Briefly, splenocytes were isolated from C57BL/6 mice, and plated in triplicate in 6 well tissue culture plates after red blood cell lysis as described above. The cells were treated with or without 5% BD-BRM for various time points. At each time point, adherent and nonadherent cells were harvested and pooled, RNA was extracted by Trizol method, followed by cDNA preparation. Real time PCR was subsequently performed from the cDNA. Values were normalized to beta actin controls, and then compared to unstimulated samples. Results demonstrated that BD-BRM induced IL-17E expression from splenocytes, which peaked between 24 and 32 hours post-stimulation (FIG. 3), with 1.74- and 1.72-fold increase as compare to PBS-treated group, respectively. There was a difference in IL-17E production of splenocytes from BD-BRM-treated mice and PBS-treated mice, with p value 0.02 and 0.01 at 24 and 32 hours post-stimulation, respectively. Results represent 5-6 experiments per time point.

Example 4

B Cells and T Cells Are Capable of Producing IL-17E in Response to BD-BRM

The splenocytes isolated from C57BL/6 mice are composed of various immune cell populations including B cells, T cells, macrophages and NK cells. In order to determine which cell type(s) were predominantly producing IL-17E in splenocytes upon BD-BRM stimulation, different cell populations were isolated from the spleen and exposed to BD-BRM.

B Cell and T Cell Isolation:

The isolation of splenic B and T cells was performed using EasySep CD19 positive selection protocol for B cells, and EasySep CD90.2 positive selection protocol for T cells (StemCell Technologies, BC) according to manufacturer's instructions. The procedures yielded ≧96% purity.

Flow Cytometric Analysis:

For cell surface marker staining, $1 \times 10^6$ cells/sample were incubated with antigen specific antibodies in 100 µl of staining solution (PBS containing 2% FCS) on ice for 30 minutes. The cells were subsequently washed twice with staining solution and either fixed with 0.5% paraformaldehyde in PBS. Intracellular cytokine staining was performed according to manufacturer's instructions, (eBioscience). Briefly, following last wash, cells were fixed by adding 100 µl of Fixation solution for 20 minutes in the dark at room temperature. Cells were washed once in Permeabilization buffer and subsequently resuspended in Permeabilization buffer for 5 minutes prior to addition of anti-cytokine antibody. Anti-IL-17E were conjugated to biotin, and used at a concentration of 1/20. After a 20 minute incubation in the dark at room temperature, cells were washed once and resuspended again in Permeabilization buffer, followed by incubation with the secondary antibody, Phycoerythrin-Cy5.5-conjugated Streptavidin (eBioscience) for 20 minutes as previously described. Cells were washed once more in Permeabilization buffer, resuspended in 0.5 ml of staining solution and stored at 4° C. for analysis. Samples were analyzed by flow cytometry using CellQuest software (FACSCalibur, Becton Dickinson, San Jose, Calif.).

Figure 4:
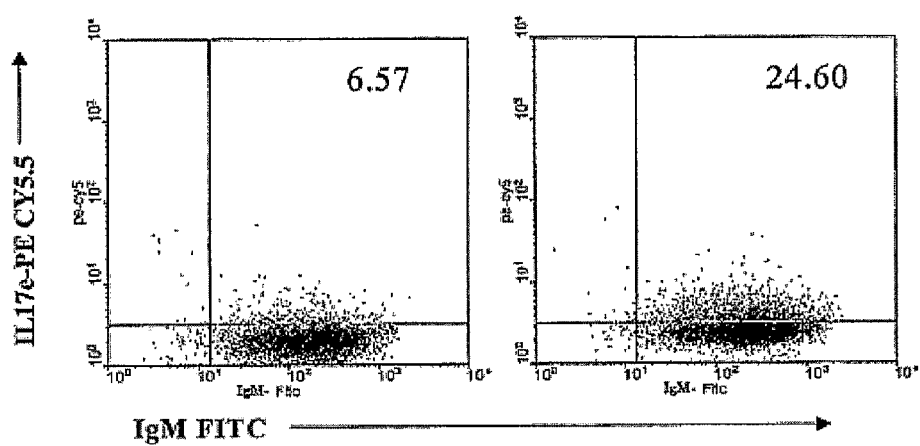
FIG. 4 depicts expression of interleukin 17E in B cells (FIG. 4A) and in T cells (FIG. 4B) isolated from spleens collected from C57BL/6 mice and with or without in vitro bile-derived biological response modifier (BD-BRM) composition treatment.
Figure 4:
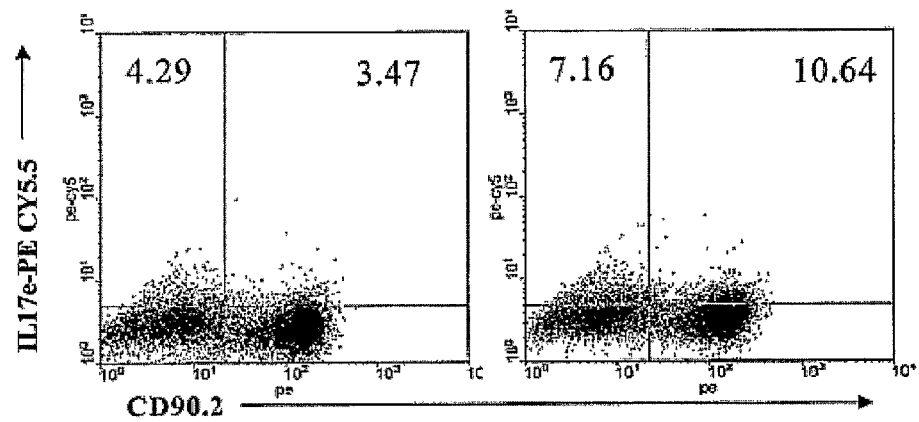

B cells were isolated from splenocytes and plated in 6 well culture with or without 5% BD-BRM. After 24 hours, cells were harvested, surface stained with anti-IgM antibodies [fluorescein isothiocyanate (FITC)-anti-mouse IgM (eB121-15F9; IgG2a from eBioscience (San Diego, Calif.)], followed by intracellular staining using either isotype control, IgG2b coupled to biotin or anti-IL-17E coupled to biotin, followed by phycoerythrin (PE)-Cy5.5-conjugated streptavidin. Samples were then analyzed by Flow Cytometry (FIG. 4A). T cells were isolated from splenocytes using the EasySep murine T cell isolation Kit, by CD90.2 expression. After 48 hour culture, harvested T cells were stained for IL-17E intracellularly as described above (FIG. 4B).

Flow cytometric analysis of intracellular cell staining of IL-17E demonstrated that splenic B cells treated with BD-BRM for 24 hours in vitro expressed a higher level of IL-17E as compared to controls (24.60% vs 6.57%) (FIG. 4A). Splenic T cells were also shown similarly to express IL-17E after 48 hour in vitro treatment with BD-BRM (10.64% vs 3.47%) (FIG. 4B). Other cell types, such as macrophages and NK cells were enriched for flow cytometric analysis, but IL-17E was not induced from these populations upon exposure to BD.

Figure 5:
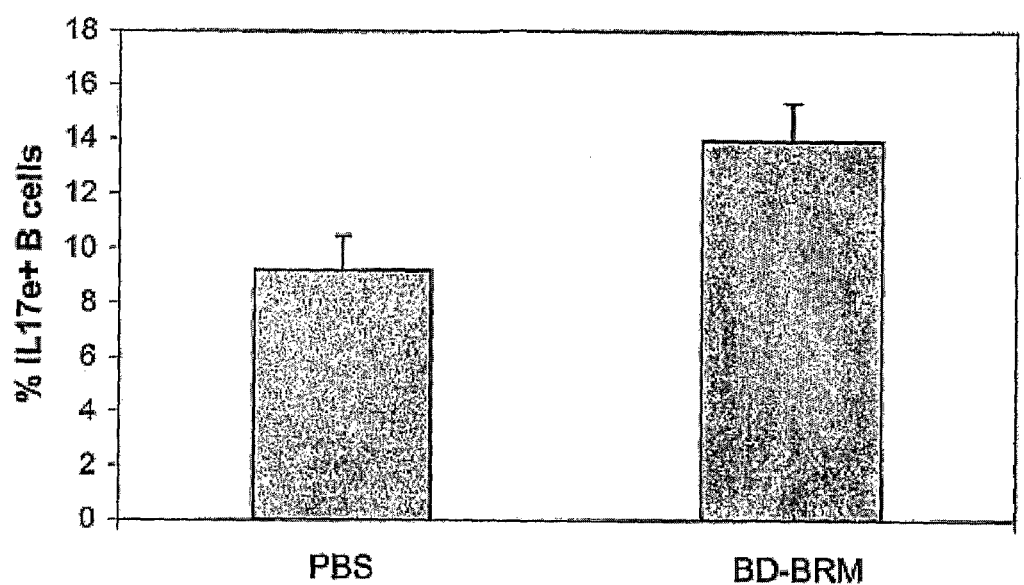
FIG. 5 depicts expression of interleukin 17E in B cells isolated from spleens collected from CD-1 nude mice bearing human melanoma tumours treated with PBS or a bile-derived biological response modifier (BD-BRM) composition.

The high expression of IL-17E from splenic B cells was also observed from C8161-tumour bearing CD-1 nude mice that have a T-cell functional deficiency. Briefly, the CD1 nude mice bearing human melanoma C8161 xenograft were treated i.p. for 4 weeks with either PBS or BD-BRM daily (0.2 ml/d/ip). Splenocytes were isolated from individual spleens, and surface stained with anti-IgM followed by intracellular staining for IL-17E. The percentage of IL-17E positive stained cells from IgM+ gated cells was tabulated. *p=0.04; n=5. Flow cytometric analysis demonstrated that the percentage of splenic B cells that expressed IL17E was higher in BD-BRM-treated mice compared to PBS-treated mice (9.20 vs 13.96%, p=0.04) (FIG. 5).

Example 5

Increased Activated Splenic B Cells in Mice Treated with a BD-BRM Composition

As demonstrated in the preceding examples, IL-17E production was increased in BD-BRM-treated mice and B cells were capable of producing IL-17E. The increase in B cells was examined in BD-BRM-treated CD-1 nude mice. Briefly, the mice with human melanoma xenografts were treated for 4 weeks with either BD-BRM or PBS, as described in the preceding examples. Splenocytes were examined by flow cytometry for B cells using anti-IgM antibodies.

Antibodies and Reagents:

Antibodies fluorescein isothiocyanate (FITC)-anti-mouse IgM (eB121-15F9; IgG2a), phycoerythrin (PE) anti-mouse CD86 (GL1; IgG2a) and PE anti-mouse CD80 (16-10A1; hamster IgG) were purchased from eBioscience (San Diego, Calif.).

Flow Cytometric Analysis:

Flow cytometry was performed as described above. Briefly, splenocytes were isolated individually from CD1-nude C8161 tumour bearing mice treated 4 weeks with BD-BRM or PBS. Red blood cells were removed, followed by surface staining with (A) anti-IgM antibody-FITC or (B) anti-IgM-FITC and anti-CD80-PE+anti-CD86-PE by flow cytometry.

Figure 6:
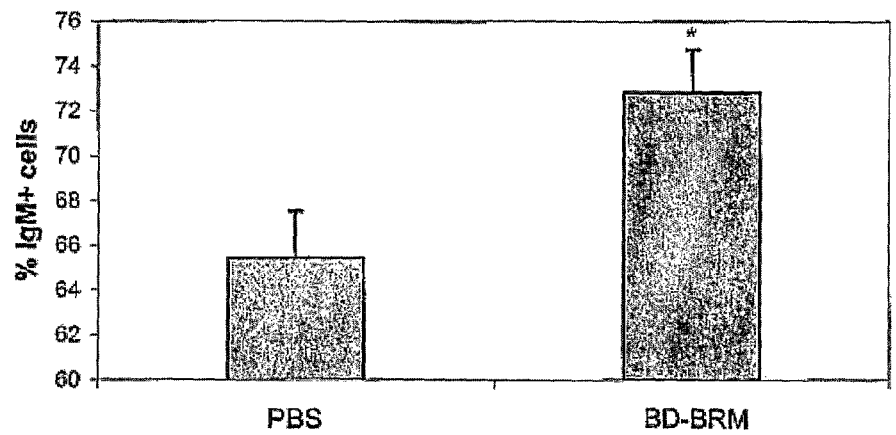
FIG. 6 depicts detection of activated splenic B cells isolated from CD-1 nude mice bearing human melanoma tumours treated with PBS or a bile-derived biological response modifier (BD-BRM) composition, percent IgM positive (FIG. 6A) and percent IgM, CD80 and CD86 positive (FIG. 6B).
Figure 6:
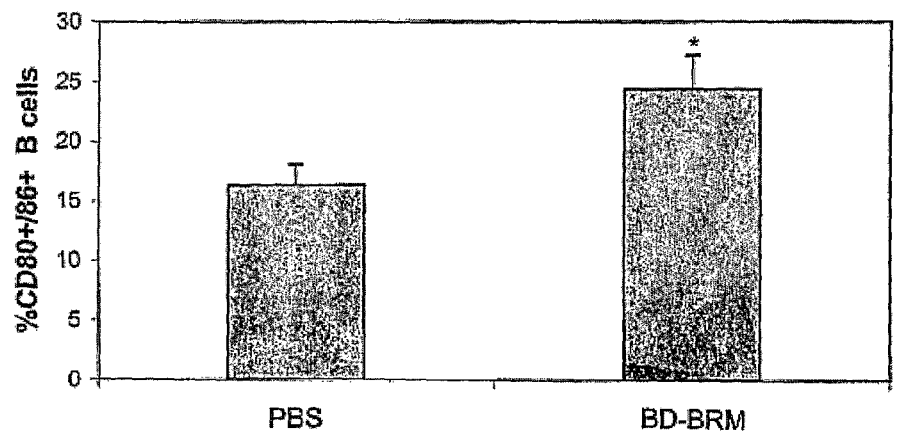

Results:

B cells were significantly increased in the spleens of BD-BRM-treated mice as compared to controls (72.84±1.9 vs 65.44±2.1%, p=0.011) (FIG. 6A). Furthermore, by double staining the B cells with the activation markers, CD80 and CD86, there was also an increase in activated B cells in the spleen following BD-BRM treatment as compared to PBS treatment (24.37±2.8 vs 16.31±1.7%, p=0.022) (FIG. 6B). These results demonstrate that BD-BRM treatment results in increased activated B cells. The p values for A and B are 0.011 and 0.02 respectively; n=30.

Example 6

BD-BRM Induces Blood Eosinophilia

Eosinophils in the blood of BD-BRM treated mice were examined using the surface marker for mouse eotaxin receptor, CCR3, which has been shown to be expressed exclusively on murine eosinophils.

Briefly, peripheral blood was isolated individually from CD1-nude C8161 tumour bearing mice treated for 4 weeks with BD-BRM or PBS, as described in the preceding examples. Red blood cells were removed from the blood, followed by surface staining with anti-CCR3 antibody-PE (83101; IgG2a) from R&D systems, (Birmingham, Ala.), analyzed by flow cytometry, as described above.

Figure 7:
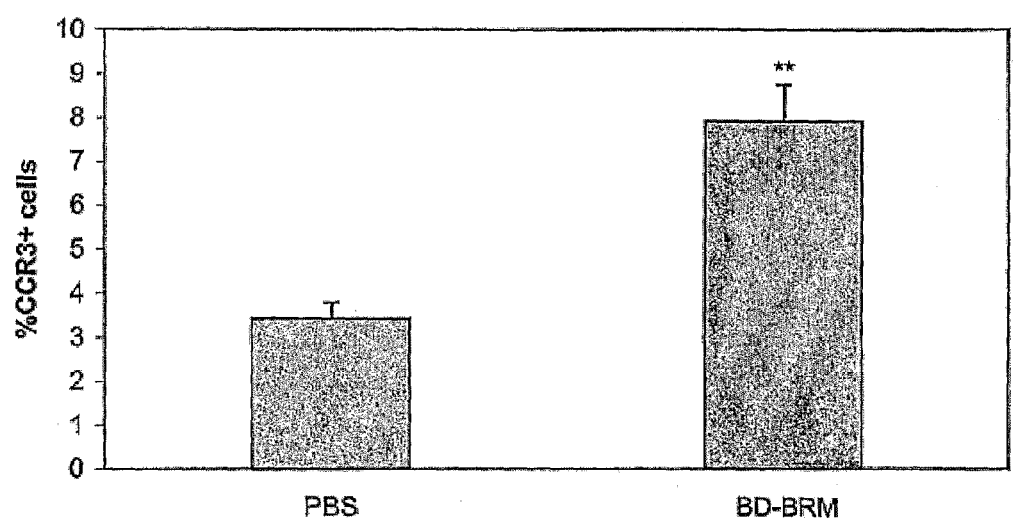
FIG. 7 depicts detection of CCR3 positive eosinophils in peripheral blood isolated from CD-1 nude mice bearing human melanoma tumours treated with PBS or a bile-derived biological response modifier (BD-BRM) composition.

As shown in FIG. 7, higher percentages of CCR3+ cells resulted from BD-BRM treated mice as compared to controls (3.42 vs 7.92%).

Example 7

Increased Eosinophil Infiltration Into Tumours in Mice Treated with a BD-BRM Composition Histochemical Detection of Eosinophils and Computer-Assisted Image Analysis:

Tumours were excised from CD-1 nude mice bearing human melanoma C8161 xenografts that had been treated with either PBS or BD-BRM as described in Example 1. The tumours were fixed in PLP fixative (2% paraformaldehyde containing 0.075M lysine and 0.01M sodium periodate solution) overnight at 4° C. The samples were then dehydrated in graded alcohols, embedded in low melting point paraffin and 5 μm sections were cut on a rotary microtome. Paraffin sections were stained for eosinophils using Sirius red method as described previously. Briefly, the sections were deparaffinized, stained with haematoxylin for 2 seconds, differentiated in distilled water and treated with 70% ethanol for 2 seconds, then stained with 0.5% Sirius red (Sigma) solution at room temperature for 1 hour. After dehydration with increasing concentration of ethanol, the sections were mounted with permount (Fisher Scientific company).

Figure 8:
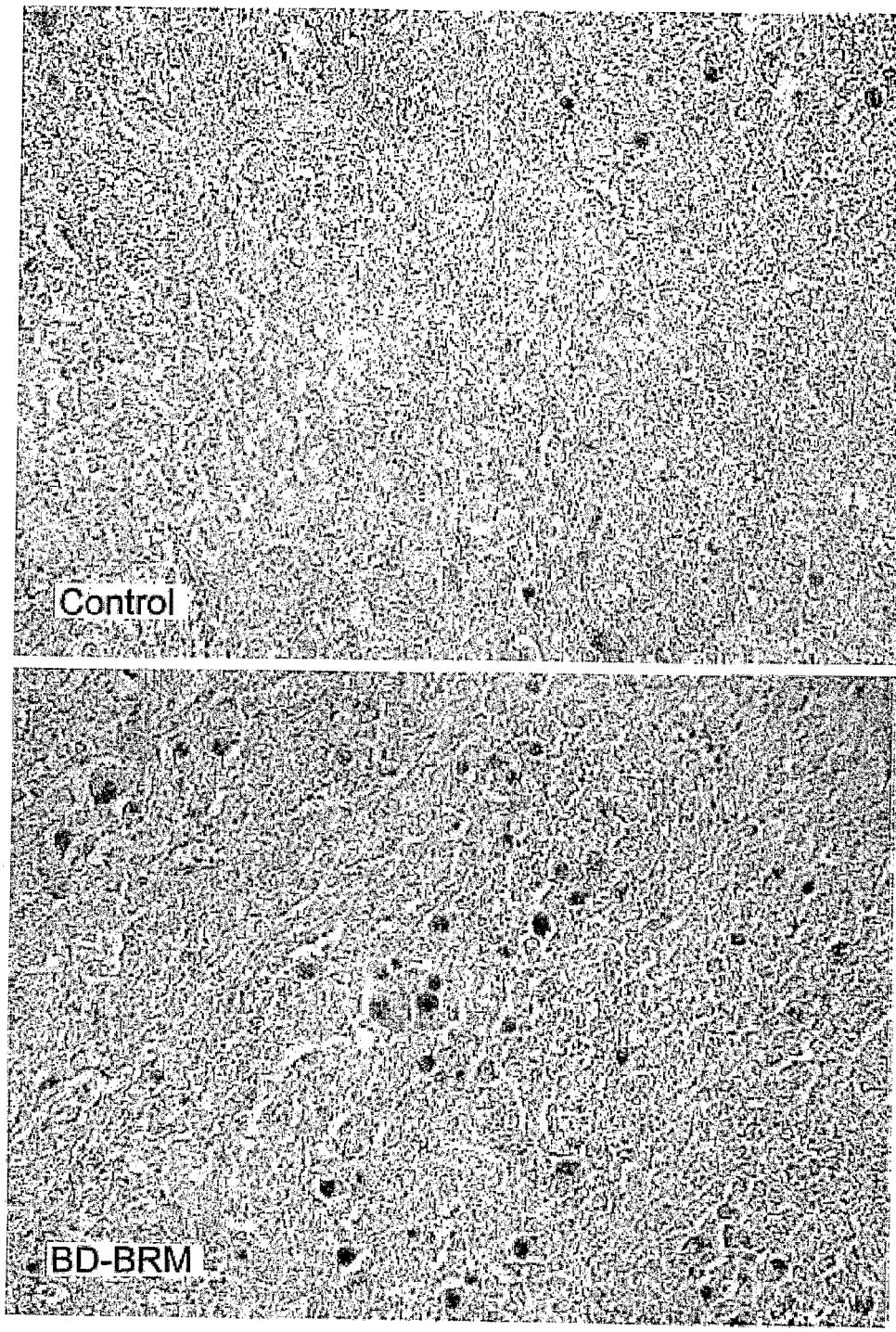
FIG. 8 depicts histochemical identification of eosinophil infiltration in tumours excised from CD-1 nude mice bearing human melanoma tumours treated with PBS or a bile-derived biological response modifier (BD-BRM) composition.

Histochemistry results revealed that there was an increased eosinophil infiltration in tumours isolated from BD-BRM-treated mice as compared with controls (FIG. 8).

Figure 9:
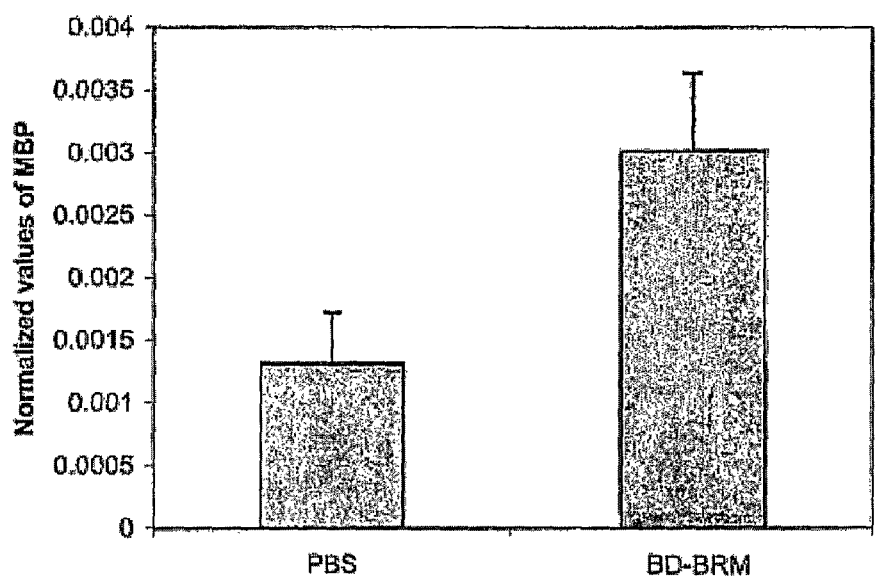
FIG. 9 depicts expression of major basic protein (MBP) (FIG. 9A) and eosinophil peroxidase (EPO) (FIG. 9B) in tumours isolated from CD-1 nude mice bearing human melanoma tumours treated with PBS or a bile-derived biological response modifier (BD-BRM) composition.
Figure 9:
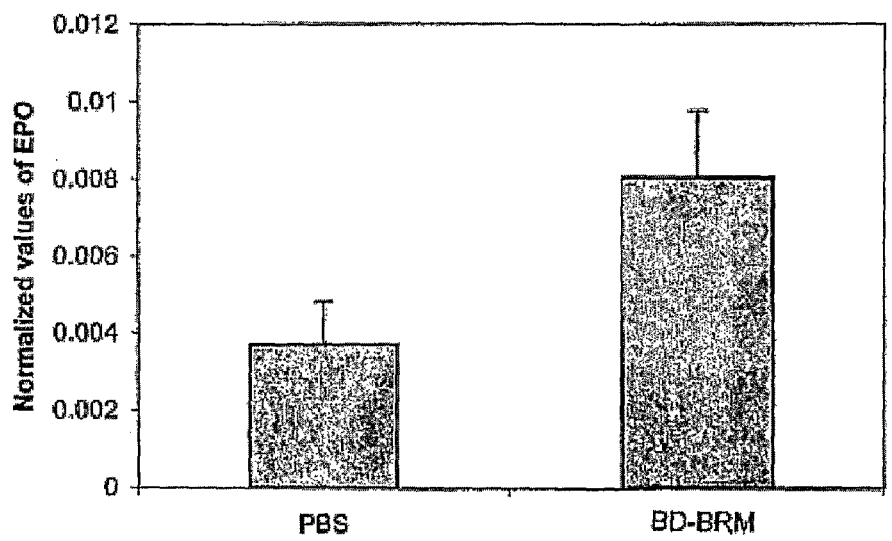

Eosinophil infiltration of tumours was further analyzed by real-time RT-PCR for eosinophil mediators, major basic protein (MBP) and eosinophil peroxidase (EPO). Briefly, CD-1 nude mice bearing human melanoma C8161 xenograft were treated i.p. for 4 weeks with either PBS or BD-BRM daily (0.2 ml/d/ip). Tumours were isolated from the mice, followed by RNA isolation and cDNA preparation as described above. Real-time PCR was performed for MBP (FIG. 9A) or EPO (FIG. 9B). Values obtained were normalized to beta-actin. Results demonstrate that both markers were increased in tumours isolated from BD-BRM-treated mice compared to PBS controls (FIG. 9). This demonstrated that BD-BRM induced the recruitment of eosinophils to the tumours.

Example 8

Induction of IL-5 in Tumours from Mice Treated with a BD-BRM Composition

Expression of IL-5 and eotaxin was determined in tumours from BD-BRM-treated mice, via RT-PCR as described above. Both IL-5 and eotaxin can cooperate to mobilize and recruit eosinophils from the bone marrow into the tissue through the blood. They also promote activation of eosinophils.

Figure 10:
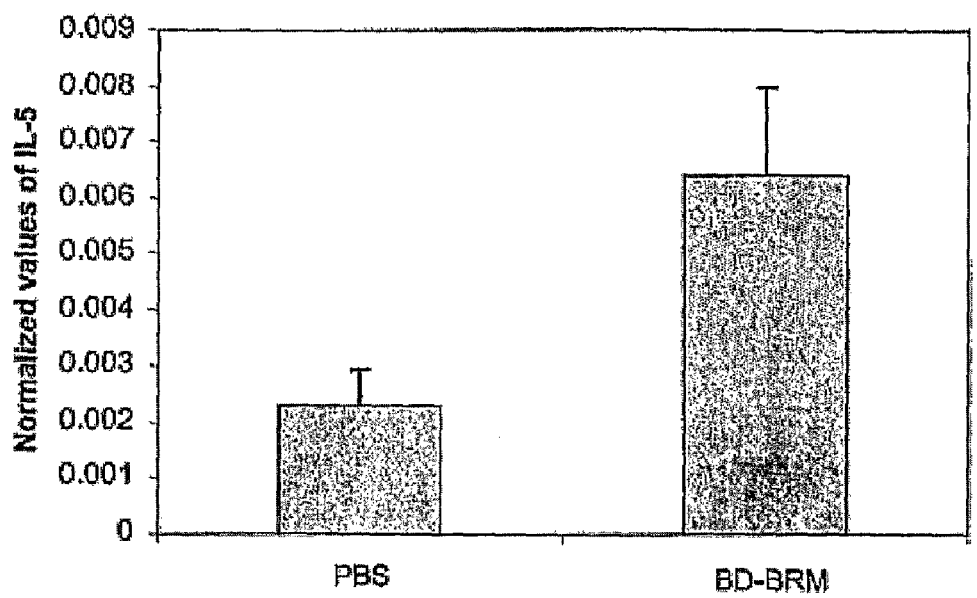
FIG. 10 depicts expression of interleukin-5 (IL-5) (FIG. 10A) and eotaxin (FIG. 10B) in tumours isolated from CD-1 nude mice bearing human melanoma tumours treated with PBS or a bile-derived biological response modifier (BD-BRM) composition.
Figure 10:
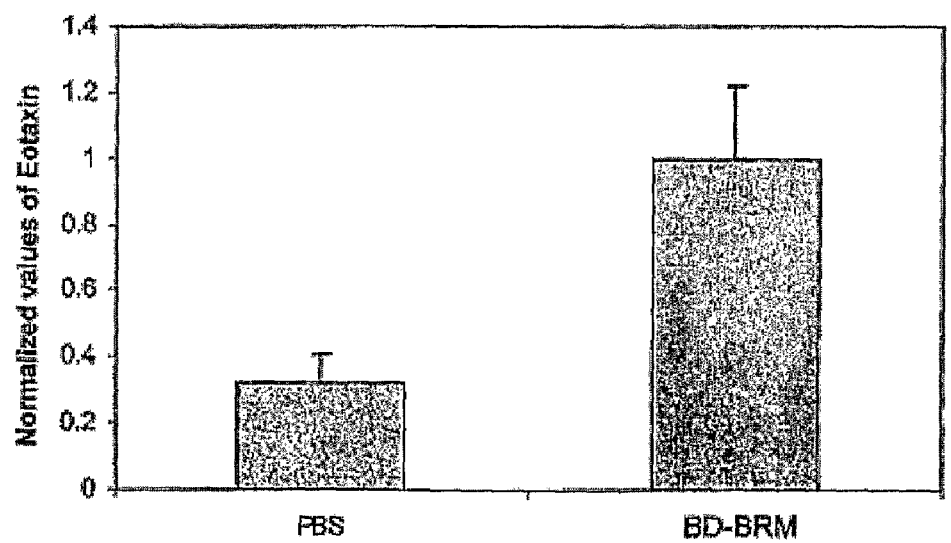

As shown in FIG. 10, both IL-5 (FIG. 10A) and Eotaxin (FIG. 10B) were increased in tumours from mice treated with BD-BRM as described in Example 1. The results demonstrated that the recruitment of eosinophils to tumours of BD-BRM treated mice was associated with IL-5 and eotaxin expression.

Example 9

Antitumour Efficacy of Human Interleukin 17E in a Melanoma Xenograft Model

The role of endogenous interleukin 17E in tumour growth inhibition as demonstrated in Examples 1-4 indicated that interleukin 17E has anti-cancer activity. Accordingly, the ability of interleukin 17E to inhibit tumour growth was examined as outlined in the following Example and in Examples 10-12.

Recombinant human IL-17E was obtained from Pepro-Tech, Inc., and is present in the preparation as a 33.8 kDA disulphide linked homodimer of two 145 amino acid polypeptide chains. The predominant form of IL-17E in this preparation is the form starting at Tyr 33 of the human sequence provided by GenBank Accession No. AAG40848. Human melanoma C8161 cells ($10^6$ cells in 100 μl PBS) were subcutaneously implanted into the right flank of CD-1 athymic nude mice. When tumours reached a volume of 50-100 $mm^3$, mice were randomly separated into two groups of 10 animals and treated as follows:

Group I: 100 μl of PBS intraperitoneally (i.p.) per mouse every other day until the endpoint of the experiment; and
Group II: 0.04 mg/kg of recombinant human IL-17E intraperitoneally (i.p.) every other day until the endpoint of the experiment.

The size of the tumours was measured by caliper measurements throughout the experiment. Tumour volume was determined using the formula (Length×Width×Height/2). T-tests were performed to assess the statistical significance of differences in tumour sizes. A p value of $\leq 0.05$ was considered to be statistically significant.

Figure 11:
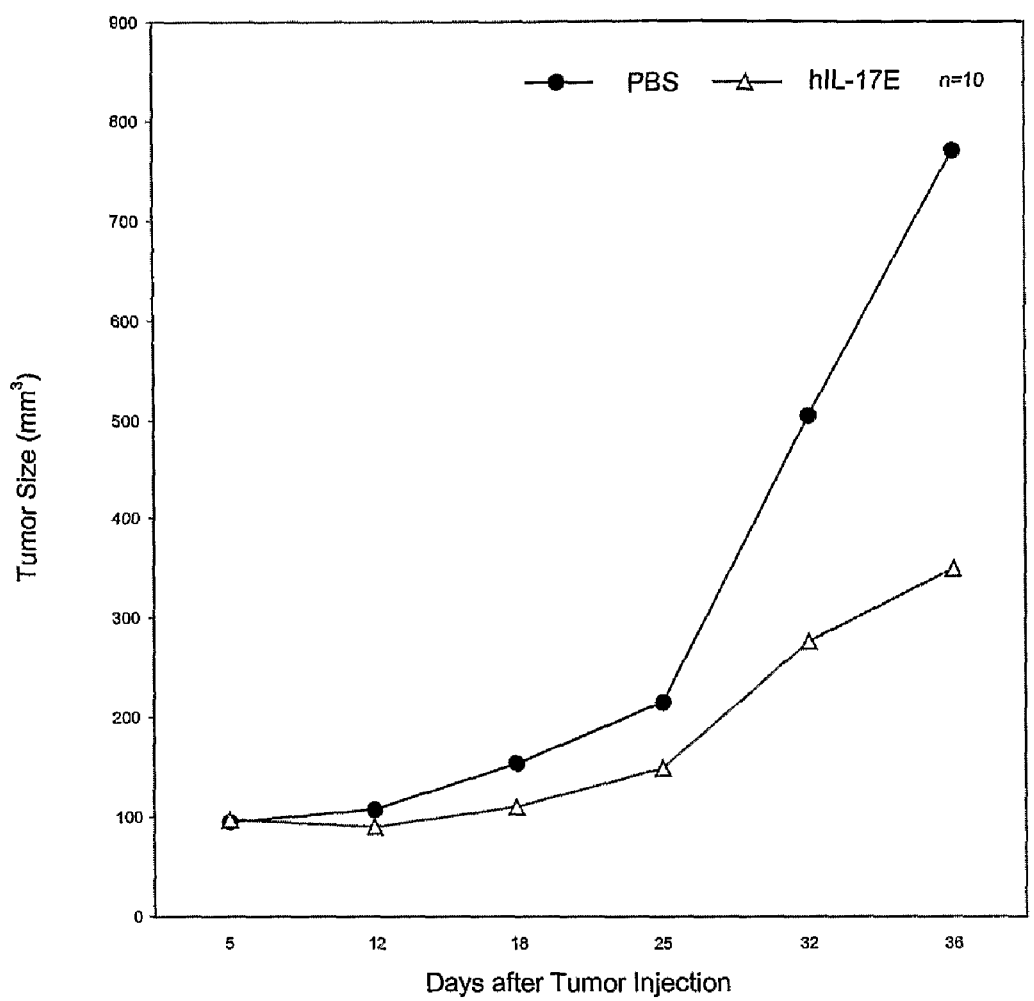
FIG. 11 depicts the effects of human interleukin 17E on human melanoma (C8161) tumour growth.

Human IL-17E was able to significantly inhibit tumour growth as compared to PBS (FIG. 11).

Example 10

Antitumour Efficacy of Murine Interleukin 17E in a Pancreatic Cancer Xenograft Model The ability of murine interleukin 17E to inhibit human pancreatic cancer growth was examined as follows. Human pancreatic cancer MiaPaCa-2 cells ($10^6$ cells in 100 μl PBS) were subcutaneously implanted into the right flank of CD-1 athymic nude mice. Murine IL-17E was obtained from R&D Systems, Inc., and is present in the preparation as a disulphide linked homodimer. The predominant form of IL-17E in this preparation is the form starting at Val 17 of the murine sequence provided as GenBank Accession No. NP 542767. When tumours reached a volume of 50-100 mm$^3$, mice were randomly separated into two groups of 8 animals and treated as follows:

Group I: 200 ml of PBS intraperitoneally (i.p.) per mouse every day until the endpoint of the experiment; and Group II: 0.04 mg/kg of murine IL-17E intraperitoneally (i.p.) every third day until the endpoint of the experiment.

The size of the tumours was measured by caliper measurements throughout the experiment. Tumour weight was determined from tumour tissue surgically excised from the animal on the last day of the experiment. T-tests were performed to assess the statistical significance of differences in tumour sizes. A p value of $\leq 0.05$ was considered to be statistically significant.

Figure 12A:
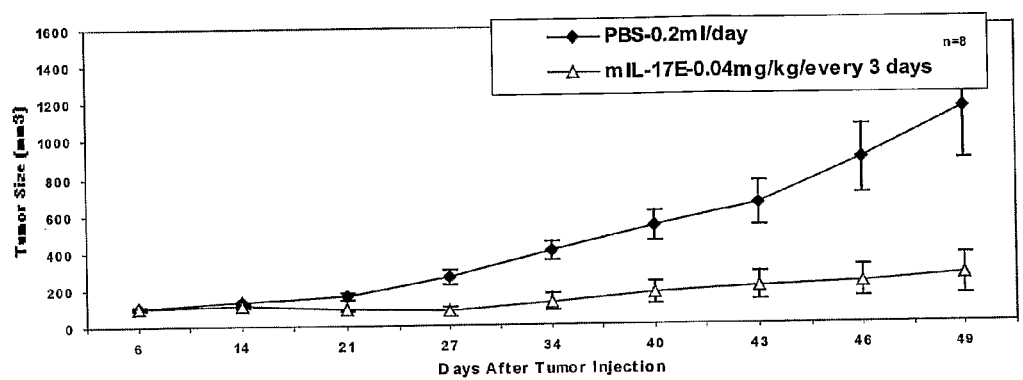
FIG. 12 depicts the effects of murine interleukin 17E on (A) tumour volume and (B) tumour weight in mice bearing human pancreatic (MiaPaCa2) xenografts.
Figure 12B:
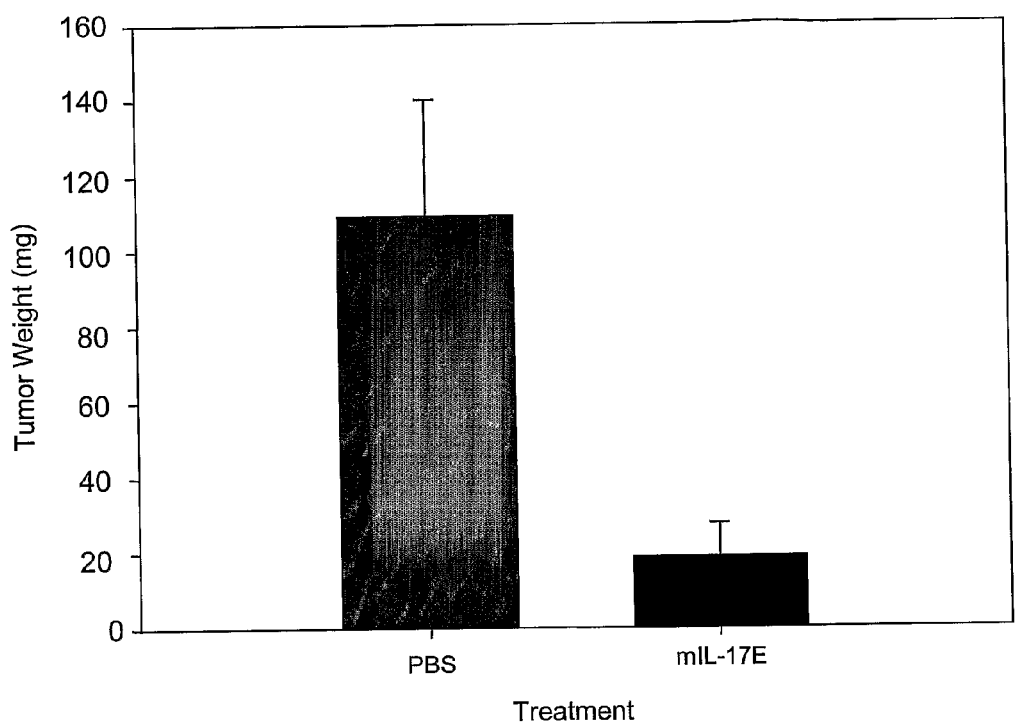

Murine IL-17E was able to significantly inhibit tumour growth as compared to PBS (FIGS. 12A and B).

Example 11

Dose-Response Antitumour Effect of Human Interleukin 17E

The effect of human IL-17E dosage on antitumour efficacy was examined using a murine xenograft model of human melanoma tumour growth. Human melanoma C8161 cells ($10^6$ cells in 100 µl PBS) were subcutaneously implanted into the right flank of CD-1 athymic nude mice. When tumours reached a volume of 50-100 mm$^3$, mice were randomly separated into four groups of 10 animals and treated as follows:

Group I: 100 µl of PBS subcutaneously (s.c.) per mouse every other day until the endpoint of the experiment;

Group II: 0.144 mg/kg of recombinant human IL-17E (PeproTech, Inc.) subcutaneously (s.c.) every other day until the endpoint of the experiment;

Group III: 0.016 mg/kg of recombinant human IL-17E subcutaneously (s.c.) every other day until the endpoint of the experiment; and Group IV: 0.0018 mg/kg of recombinant human IL-17E subcutaneously (s.c.) every other day until the endpoint of the experiment.

Figure 13:
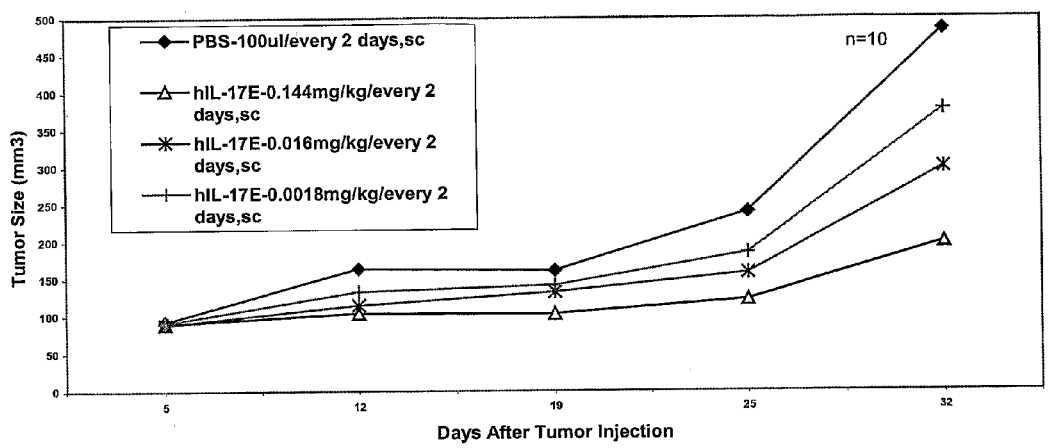
FIG. 13 depicts the dose response antitumour effect of human interleukin 17E on human melanoma (C8161) tumour growth.

Increasing doses of human IL-17E demonstrated a greater antitumour effect against human melanoma growth, indicating a dose-response effect (FIG. 13).

Example 12

Antitumour Efficacy of Interleukin 17E Alone and in Combination with BD-BRM

The antitumour efficacy of interleukin 17E alone and in combination with BD-BRM was examined using a murine xenograft model of human melanoma. The human melanoma cell line C8161 was a gift from Dr. D. R. Welch (Pennsylvania State University, Hershey, Pa.). Cells were grown in RPMI 1640 medium (Wisent Inc., St. Bruno, QC) with 10% fetal bovine serum, penicillin (100 u/ml), streptomycin (100 mg/ml) (Wisent Inc.) at 37° C. under 95%, air and 5% $CO_2$, and maintained with routine media changes. Adherent C8161 cells were passaged by trypsinization with 0.025% trypsin. CD-1 athymic nude mice and C57BL/6 (6-8-weeks old, 20-25 g, female) were purchased from Charles River (Montreal, QC). Animal protocols were in compliance with the Guide for the Care and Use of Laboratory Animals in Canada. Murine IL-17E was obtained from R&D Systems, Inc., and is present in the preparation as a disulphide linked homodimer. The predominant form of IL-17E in this preparation is the form starting at Val 17 of the murine sequence provided as GenBank Accession No. NP 542767.

Human tumour xenografts were established in mice as follows. Briefly, human melanoma C8161 cells were harvested at approximately 80% confluence and $10^6$ cells in 100 µl PBS were subcutaneously implanted into the right flank of CD-1 athymic nude mice. When tumours reached a volume of 50-100 mm$^3$, mice were randomly separated into the four groups of 10 animals and treated as follows:

Group I: 200 µl of PBS intraperitoneally (i.p) daily until the endpoint of the experiment;

Group II: 200 µl of BD-BRM intraperitoneally (i.p) daily until the endpoint of the experiment;

Group III: 1 µg/mouse/day of murine IL-17E intraperitoneally (i.p) daily for the first 10 days after the tumours reached a volume of 50-100 mm$^3$; and Group IV: 1 µg/mouse/day of murine IL-17E intraperitoneally (i.p) daily for the first 10 days after the tumours reached a volume of 50-100 mm$^3$ and 200 ul of BD-BRM intraperitoneally (i.p) daily until the endpoint of the experiment.

Tumour volume was estimated by caliper measurements, using the formula: (Length×Width×Height)/2. Tumour weight was determined from tumour tissue surgically excised from the animal on the last day of the experiment. The percentage of inhibition (%)=[(mean tumour weight of control animals-mean tumour weight of drug-treated group)/(mean tumour weight of controls)]×100. A p-value of $\leq 0.05$ was considered to be statistically significant.

Figure 14A:
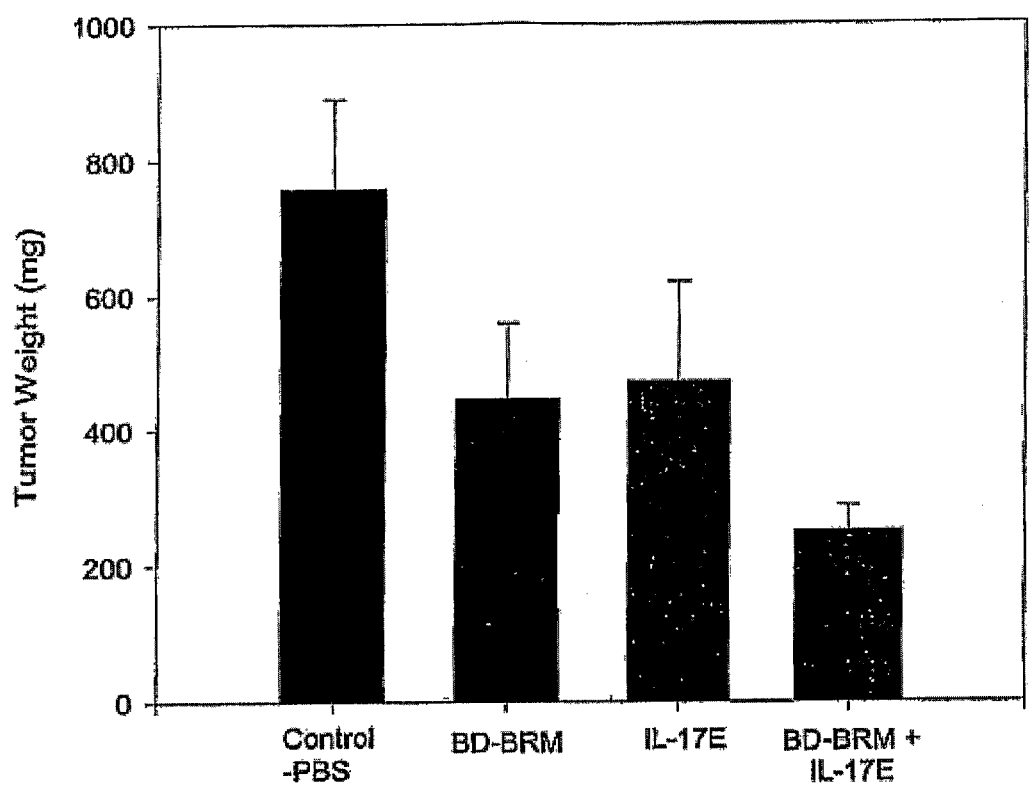
FIG. 14 depicts the effects of interleukin 17E alone and in combination with a bile-derived biological response modifier (BD-BRM) composition on (A) tumour weight and (B) tumour volume in mice bearing C8161 human melanoma xenografts.
Figure 14B:
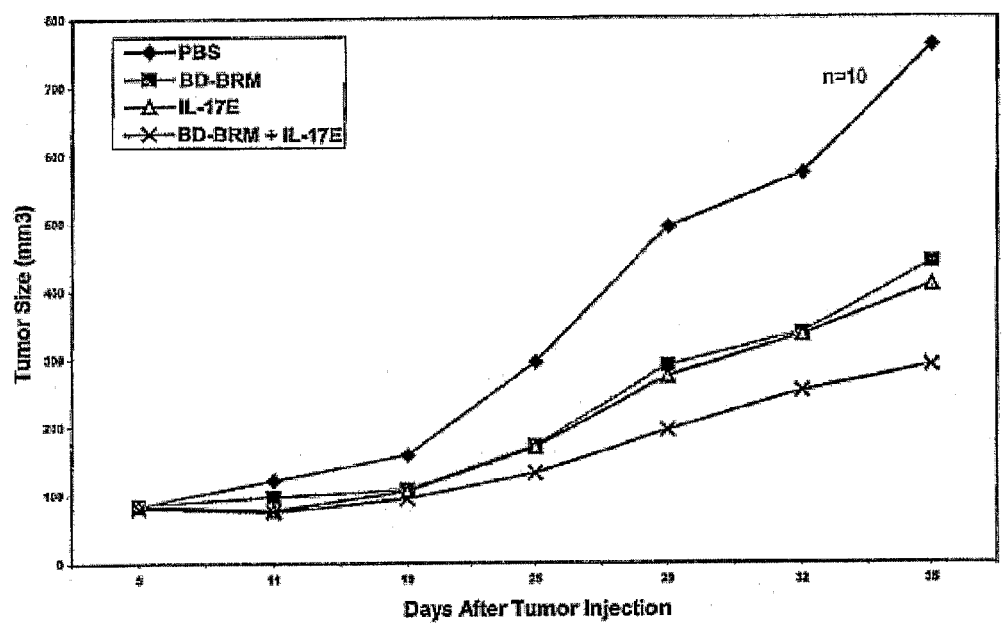

Interleukin 17E both alone and in combination with BD-BRM significantly inhibited tumour growth as compared to the PBS group (FIGS. 14A and B).

Example 13

Interleukin 17E Induced Blood Eosinophilia in Tumour Xenografted Mice

In order to confirm that the effect of BD-BRM on blood eosinophilia as described in Example 6 is due to the activity of interleukin 17E the following experiment was performed.

It has been previously demonstrated that interleukin 17E overexpression in mice induces eosinophilia (Kim et al. (2002) *Blood* 100:2330-2340). Accordingly, blood of mice treated with interleukin 17E alone or in combination with BD-BRM was analyzed by flow cytometry for the presence of eosinophils by surface staining with an antibody for mouse eotaxin receptor, CCR3, which has been shown to be expressed exclusively on murine eosinophils.

Briefly, CD1-nude C8161 tumour bearing mice were treated with PBS or interleukin 17E alone or in combination with BD-BRM as described in Example 12, and peripheral blood was isolated individually from the mice. Red blood cells were removed from the blood, followed by surface staining with anti-CCR3 antibody-PE (83101; IgG2a) from R&D Systems, (Birmingham, Ala.), and analysis by flow cytometry using the following method.

$1\times10^6$ cells/sample were incubated with the anti-CCR3 antibody-PE in 100 µl of staining solution (PBS containing 2% FCS) on ice for 30 minutes. The cells were subsequently washed twice with staining solution and fixed with 0.5% paraformaldehyde in PBS. Samples were analyzed by flow cytometry using CellQuest software (FACSCalibur, Becton Dickinson, San Jose, Calif.).

Figure 15:
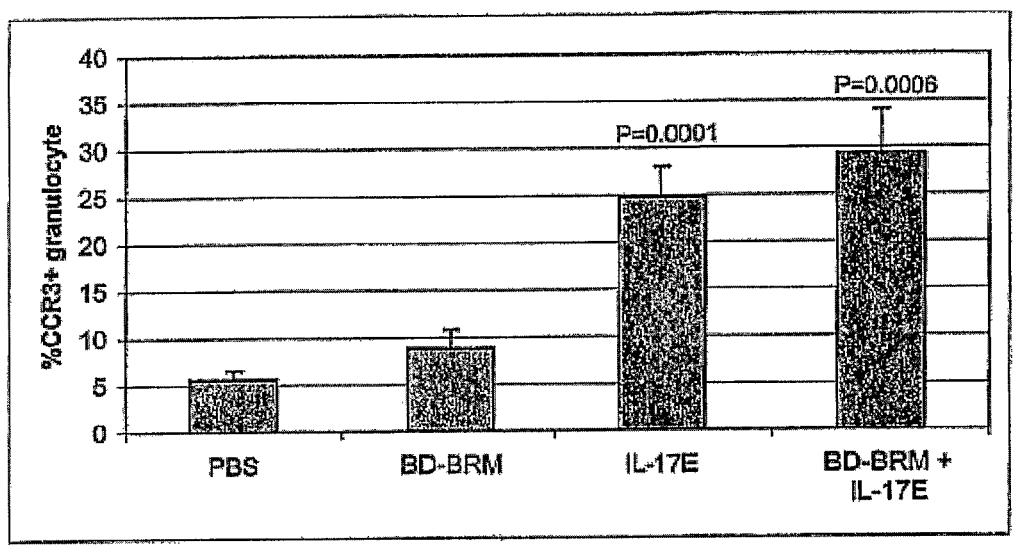
FIG. 15 depicts the effects of interleukin 17E alone and in combination with bile-derived biological response modifier (BD-BRM) composition on the number of eosinophils in the blood of mice bearing C8161 human melanoma xenografts.

The results demonstrated that the groups treated with either IL-17E or IL-17E in combination with BD-BRM had significantly increased blood eosinophilia (FIG. 15).

Example 14

Interleukin 17E Increases Eosinophils in the Spleen of Tumour Xenografted Mice It has been previously demonstrated that interleukin 17E overexpression in mice results in a significant increase in eosinophils in lymphohematopoietic tissues including the spleen (Kim et al. (2002) *Blood* 100:2330-2340). Accordingly, the number of eosinophils in the spleen of mice treated with interleukin 17E alone or in combination with BD-BRM was determined.

Briefly, single cell suspensions of spleen cells were obtained by meshing and passing through a cell strainer (70 um; Bectin Dickinson) to separate fibrous tissue. Erythrocytes were lysed with ACK (0.155 M ammonium chloride, 0.1 mM disodium EDTA, 0.01 M potassium bicarbonate, pH 7.3) for 5 minutes on ice. The single cell suspensions of spleen cells were then analyzed by flow cytometry for the presence of eosinophils by surface staining with an antibody to CCR3 using the method as described in Example 13.

Figure 16:
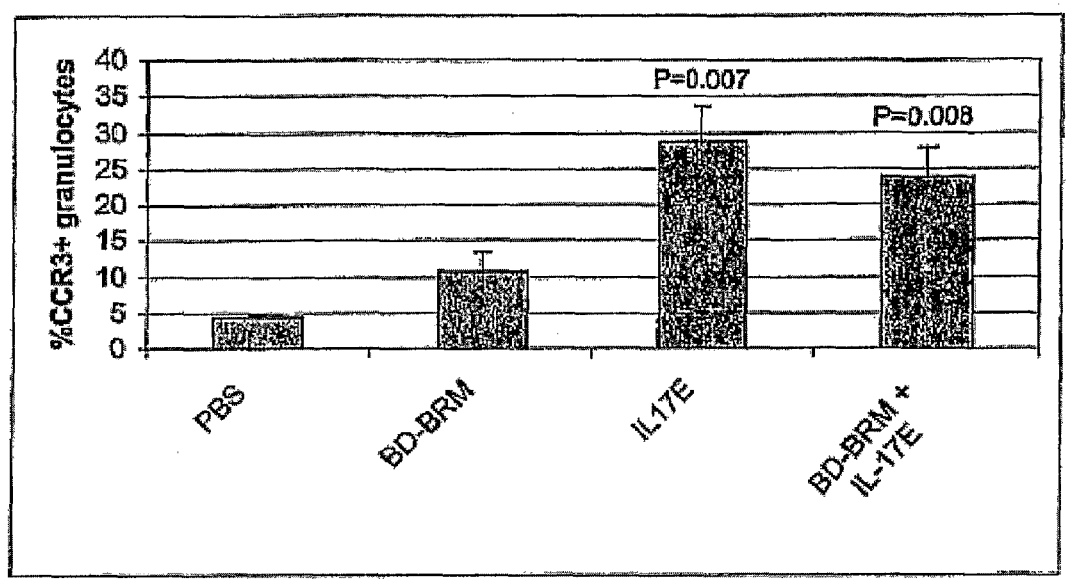
FIG. 16 depicts the effects of interleukin 17E alone and in combination with bile-derived biological response modifier (BD-BRM) composition on the number of eosinophils in the spleen of mice bearing C8161 human melanoma xenografts.

The percentage of CCR3+ cells in the granulocyte population were found to be significantly increased in the spleens of mice treated with either IL-17E or IL-17E in combination with BD-BRM (FIG. 16). The data suggest that administration of IL-17E results in the mobilization and recruitment of eosinophils into the blood and tissue (i.e. spleen).

Example 15

Increased Eosinophil Infiltration Into Tumours in Mice Treated with Interleukin 17E Alone or in Combination with a BD-BRM Composition As described in Example 7 above, treatment of mice bearing human melanoma xenografts with BD-BRM resulted in increased eosinophil infiltration into the tumour. In order to confirm this effect is due to the activity of interleukin 17E, the following experiment was performed.

Histochemical Detection of Eosinophils and Computer-Assisted Image Analysis.

Tumours were excised from CD-1 nude mice bearing human melanoma C8161 xenografts that had been treated with either PBS or BD-BRM, with or without recombinant murine IL-17E as described previously above. The tumours were fixed in PLP fixative and paraffin sections of tumours were prepared and stained for eosinophils using the Sirius Red method as described above.

Figure 17:
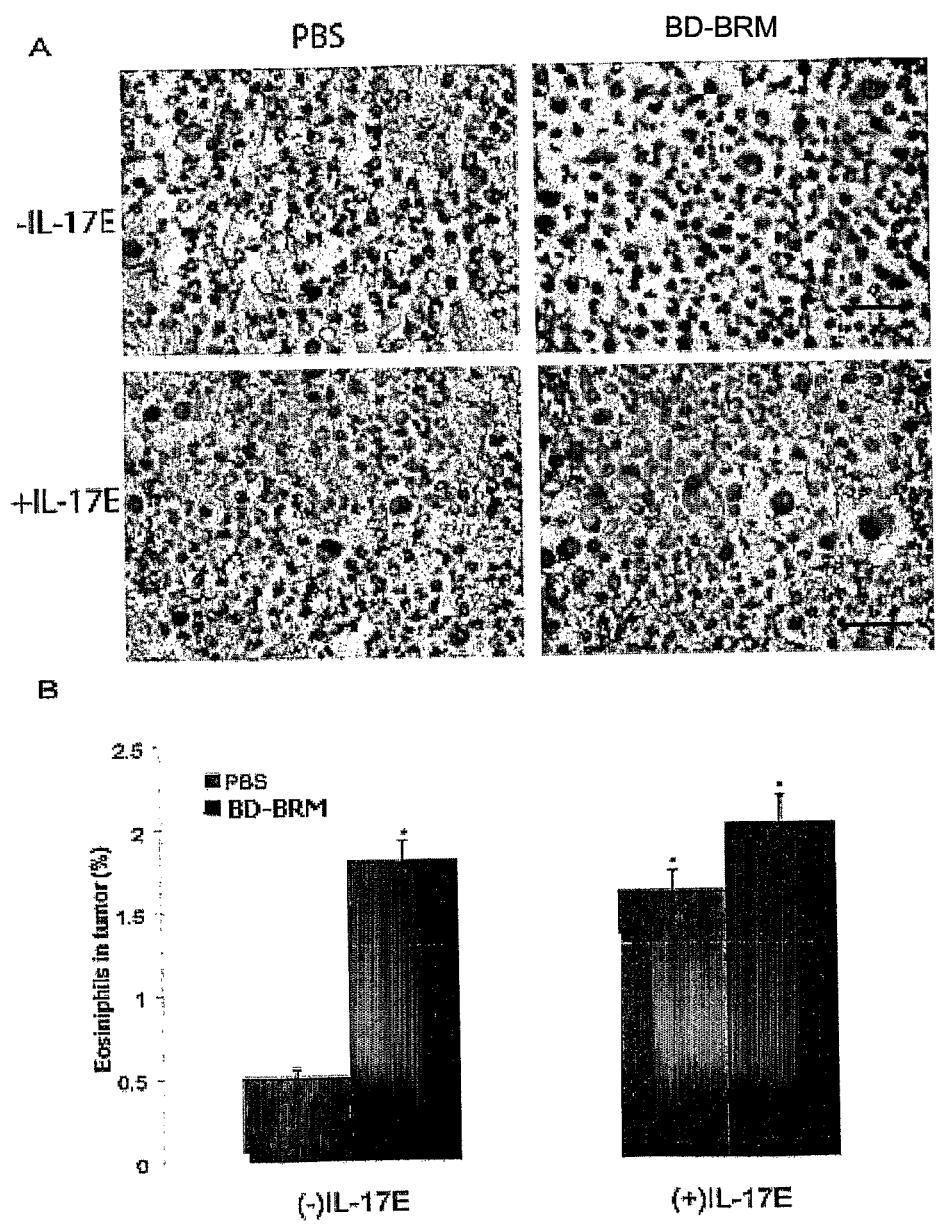
FIG. 17 depicts eosinophil infiltration into human melanoma C8161 tumours in response to treatment with PBS or a bile-derived biological response modifier (BD-BRM) composition, alone or in combination with interleukin 17E. (A) depicts representative micrographs and (B) depicts number of eosinophils per square millimeter of tumour tissue.

Histochemistry results showed there was increased eosinophil infiltration in tumours from mice treated with either IL-17E or BD-BRM, compared to mice treated with PBS, as seen in representative micrographs of sections (FIG. 17A). The scale bar in the bottom right panel represents 25 µm.

The number of eosinophils per square millimeter of tumour tissue was determined by computer-assist image analysis. Quantitative image analysis of data obtained from six tumor samples per group demonstrated that the average number of eosinophils per field was 0.5% in the PBS control group, 1.8% in the BD-BRM-treated group, 1.6% in the IL-17E group and 2.0% in the combination BD-BRM+IL-17E group. Results revealed that there was a significant increase in eosinophil infiltration into tumors isolated from mice treated with BD-BRM, IL-17E alone or combination of BD-BRM and 1'-17E as compared with PBS controls (p<0.05). Mean values±standard error are shown in FIG. 17B. (*p<0.05 compared to PBS control).

Example 16

Antitumour Efficacy of Interleukin 17E Alone or in Combination with Dacarbazine (DTIC) in a Melanoma Xenograft Model The antitumour efficacy of human interleukin 17E alone or in combination with dacarbazine (DTIC) was examined in a melanoma xenograft model. Human melanoma C8161 cells ($10^6$ cells in 100 µl PBS) were subcutaneously implanted into the right flank of CD-1 athymic nude mice. When tumours reached a volume of 50-100 mm$^3$, mice were randomly separated into five groups of 10 animals and treated as follows:

Group I: 100 µl of PBS intravenously (i.v.) per mouse every other day until the endpoint of the experiment;

Group II: 0.04 mg/kg murine IL-17E (R& D Systems, Inc.) intravenously (i.v.) per mouse every other day until the endpoint of the experiment;

Group III: 0.04 mg/kg human IL-17E intravenously (i.v.) per mouse every other day until the endpoint of the experiment;

Group IV: 80 mg/kg dacarbazine intraperitoneally (i.p.) per mouse every day for 5 days until the endpoint of the experiment; and Group V: 0.04 mg/kg human IL-17E intravenously (i.v.) per mouse every other day in combination with 80 mg/kg dacarbazine intraperitoneally (i.p.) per mouse every day for 5 days until the endpoint of the experiment.

The size of the tumours was measured by caliper measurements throughout the experiment. Tumour weight was determined from tumour tissue surgically excised from the animal on the last day of the experiment. T-tests were performed to assess the statistical significance of differences in tumour sizes. A p value of $\leq 0.05$ was considered to be statistically significant.

Figure 18A:
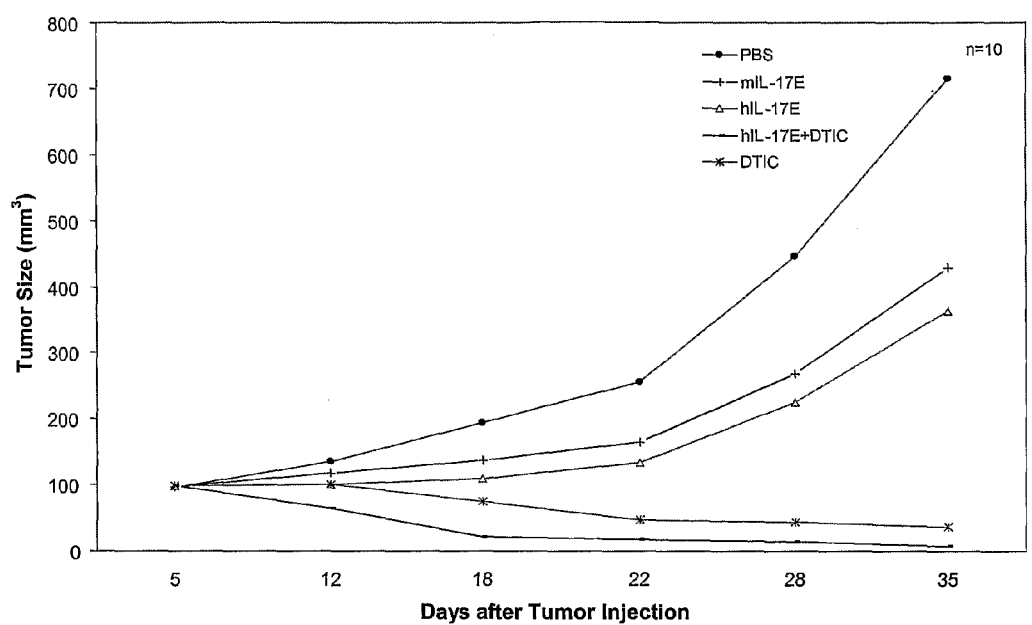
FIG. 18 depicts the effects of interleukin 17E alone or in combination with dacarbazine (DTIC) on (A) tumour volume and (B) tumour weight in mice bearing human melanoma (C8161) xenografts.
Figure 18B:
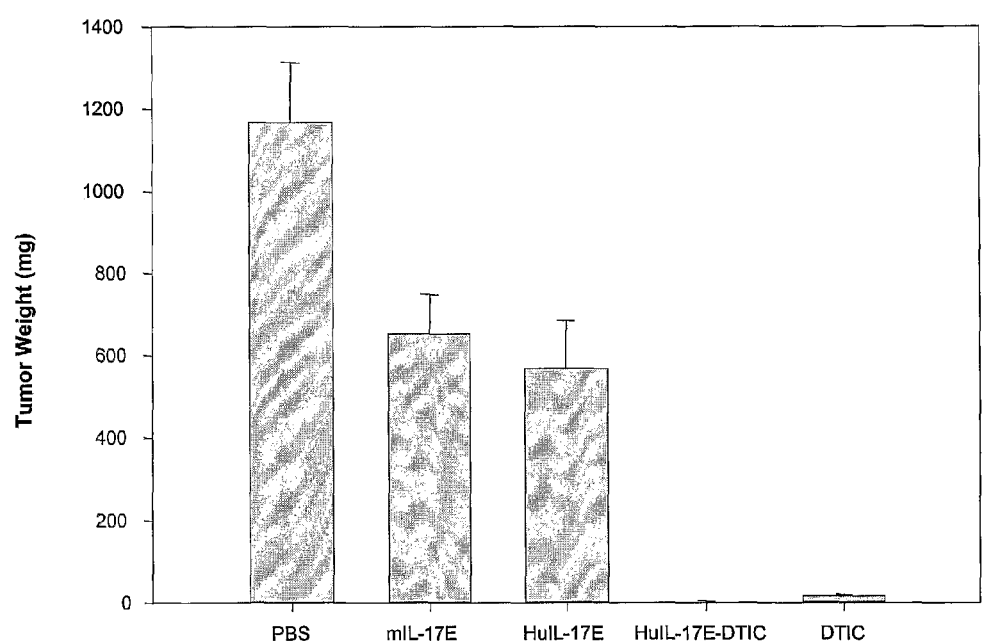

IL-17E both alone and in combination with DTIC significantly inhibited tumour growth as compared to PBS. The combination of human IL-17E and DTIC had a greater antitumour effect than either agent alone (FIGS. 18A and B).

Example 17

Antitumour Efficacy of Human Interleukin 17E Alone or in Combination with Cisplatin in an Ovarian Cancer Xenograft Model The antitumour efficacy of human interleukin 17E alone or in combination with cisplatin was examined in an ovarian cancer xenograft model. Human ovarian cancer SK-OV-3 cells ($10^6$ cells in 100 µl PBS) were subcutaneously implanted into the right flank of CD-1 athymic nude mice. When tumours reached a volume of 50-100 mm$^3$, mice were randomly separated into four groups of 10 animals and treated as follows:

Group I: 100 µl of PBS intravenously (i.v.) per mouse every other day until the endpoint of the experiment;

Group II: 0.04 mg/kg human IL-17E (PeproTech Inc.) intravenously (i.v.) per mouse every other day until the endpoint of the experiment;

Group III: 4 mg/kg cisplatin intravenously (i.v.) per mouse once per week until the endpoint of the experiment; and Group IV: 0.04 mg/kg human IL-17E intravenously (i.v.) per mouse every other day in combination with 4 mg/kg cisplatin intravenously (i.v.) per mouse once per week until the endpoint of the experiment.

The size of the tumours was measured by caliper measurements throughout the experiment. T-tests were performed to assess the statistical significance of differences in tumour sizes. A p value of 0.05 was considered to be statistically significant.

Figure 19:
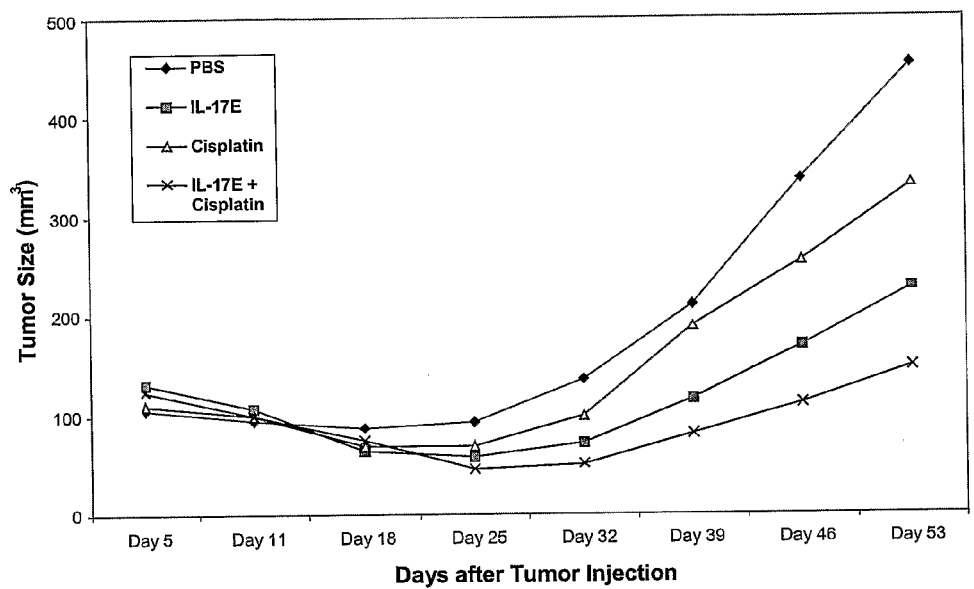
FIG. 19 depicts the effects of interleukin 17E alone or in combination with cisplatin on human ovarian cancer (SK-OV-3) xenografts.

IL-17E both alone and in combination with cisplatin significantly inhibited tumour growth as compared to PBS. The combination of human IL-17E and cisplatin had a greater antitumour effect than either agent alone (FIG. 19).

Example 18

Antitumour Efficacy of Human Interleukin 17E Alone or in Combination with Either Taxotere® or Tarceva® in a Lung Cancer Xenograft Model The antitumour efficacy of human interleukin 17E alone or in combination with either Taxotere® (doecetaxel) or the EGFR kinase inhibitor Tarceva® (erlotinib) was examined in a lung cancer xenograft model. Human lung carcinoma H460 cells ($10^6$ cells in 100 µl PBS) were subcutaneously implanted into the right flank of CD-1 athymic nude mice. When tumours reached a volume of 50-100 mm$^3$, mice were randomly separated into seven groups of 10 animals and treated as follows:
Group I: 100 µl of PBS intravenously (i.v.) per mouse every other day until the endpoint of the experiment;
Group II: 0.04 mg/kg human IL-17E (PeproTech Inc.) intravenously (i.v.) per mouse every other day until the endpoint of the experiment;
Group III: 10 mg/kg Taxotere® intravenously (i.v.) per mouse given once only at the beginning of the experiment;
Group IV: 25 mg/kg Tarceva® orally (p.o.) per mouse every other day until the endpoint of the experiment;
Group V: 100 mg/kg Tarceva® orally (p.o.) per mouse every day for 5 days, followed by a one week rest period, then every day for 5 days;
Group VI: 0.04 mg/kg human IL-17E intravenously (i.v.) per mouse every other day until the endpoint of the experiment, in combination with 10 mg/kg Taxotere® intravenously (i.v.) per mouse given once only at the beginning of the experiment; and
Group VII: 0.04 mg/kg human IL-17E intravenously (i.v.) per mouse every other day in combination with 25 mg/kg Tarceva® orally (p.o.) per mouse every day until the endpoint of the experiment.

The size of the tumours was measured by caliper measurements throughout the experiment. Tumour weight was determined from tumour tissue surgically excised from the animal on the last day of the experiment. T-tests were performed to assess the statistical significance of differences in tumour sizes. A p value of $\leq 0.05$ was considered to be statistically significant.

Figure 20A:
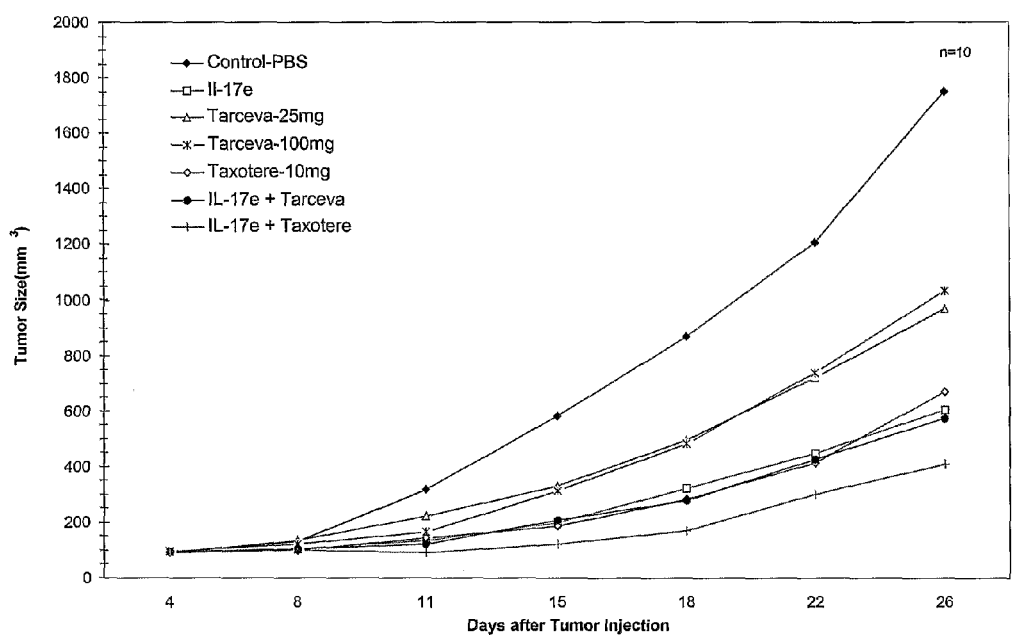
FIG. 20 depicts the effects of interleukin 17E alone or in combination with either Taxotere or Tarceva on (A) tumour volume and (B) tumour weight in CD-1 athymic nude mice bearing human lung cancer tumour (H460) xenografts.
Figure 20B:
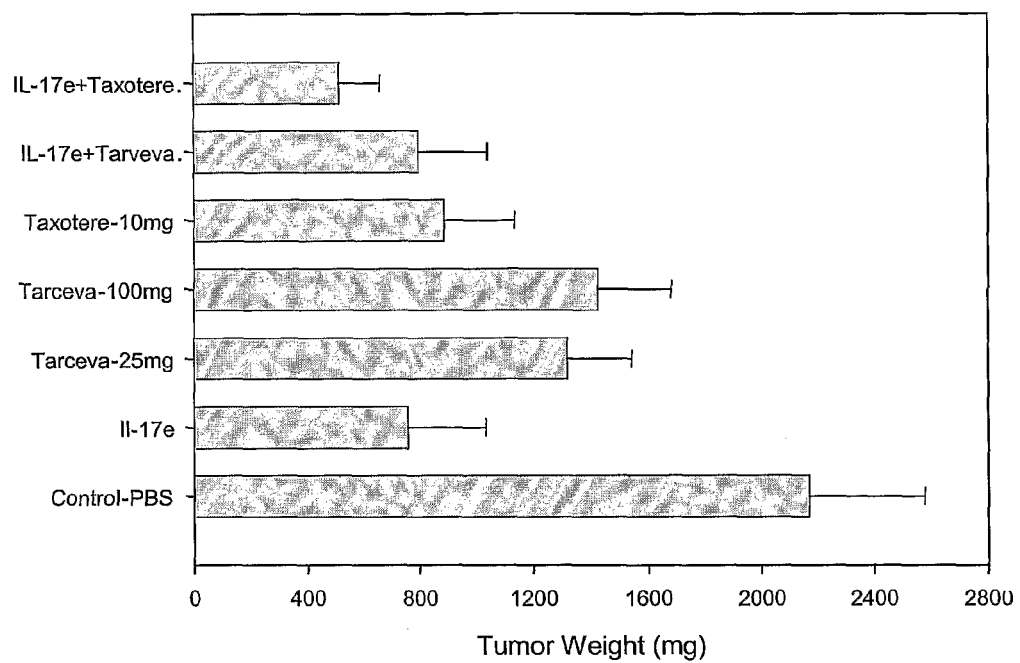

IL-17E both alone and in combination with either Taxotere® or Tarceva® significantly inhibited tumour growth as compared to PBS. The combination of human IL-17E and either Taxotere® or Tarceva® had a greater antitumour effect than either agent alone (FIGS. 20A and B).

Example 19

Antitumour Efficacy of Human Interleukin 17E Alone or in Combination with Either CPT-11 or Avastin in a Colon Cancer Xenograft Model The antitumour efficacy of human interleukin 17E alone or in combination with either CPT-11 (docetaxel) or the anti-VEGF antibody Avastin® (bevacizumab) was examined in a colon cancer xenograft model. Human colon adenocarcinoma HT-29 cells ($10^6$ cells in 100 µl PBS) were subcutaneously implanted into the right flank of CD-1 athymic nude mice. When tumours reached a volume of 50-100 mm$^3$, mice were randomly separated into six groups of 10 animals and treated as follows:
Group. I: 100 µl of PBS intravenously (i.v.) per mouse every other day until the endpoint of the experiment;
Group 0.04 mg/kg human IL-17E intravenously (i.v.) per mouse every other day until the endpoint of the experiment;
Group III: 20 mg/kg CPT-11 intravenously (i.v.) per mouse every day for 5 days starting at the beginning of the experiment;
Group IV: 10 µg/kg Avastin® intraperitoneally (i.p.) per mouse every other day until the endpoint of the experiment; and
Group V: 0.04 mg/kg human IL-17E intravenously (i.v.) per mouse every other day until the endpoint of the experiment, in combination with 20 mg/kg CPT-11 intravenously (i.v.) per mouse every day for 5 days starting at the beginning of the experiment.
Group VI: 0.04 mg/kg human IL-17E intravenously (i.v.) per mouse every other day in combination with 10 µg/kg Avastin® intraperitoneally (i.p.) per mouse every other day until the endpoint of the experiment.

The size of the tumours was measured by caliper measurements throughout the experiment. Tumour weight was determined from tumour tissue surgically excised from the animal on the last day of the experiment. T-tests were performed to assess the statistical significance of differences in tumour sizes. A p value of 0.05 was considered to be statistically significant.

Figure 21A:
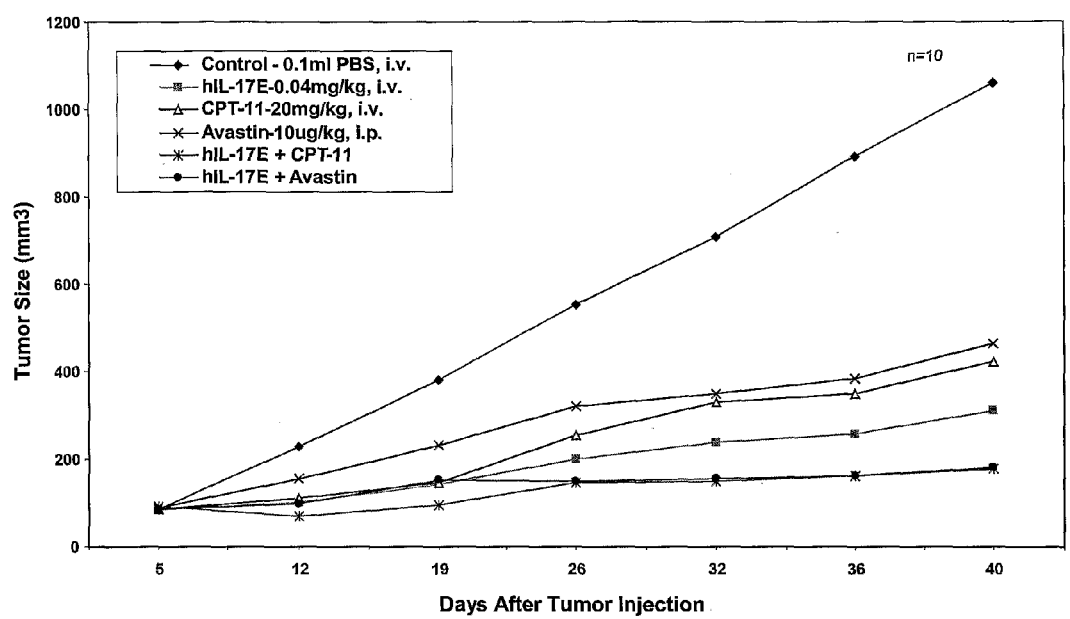
FIG. 21 depicts the effects of interleukin 17E alone or in combination with either CPT-11 or Avastin on (A) tumour volume and (B) tumour weight in CD-1 athymic nude mice bearing human colon cancer (HT-29) xenografts.
Figure 21B:
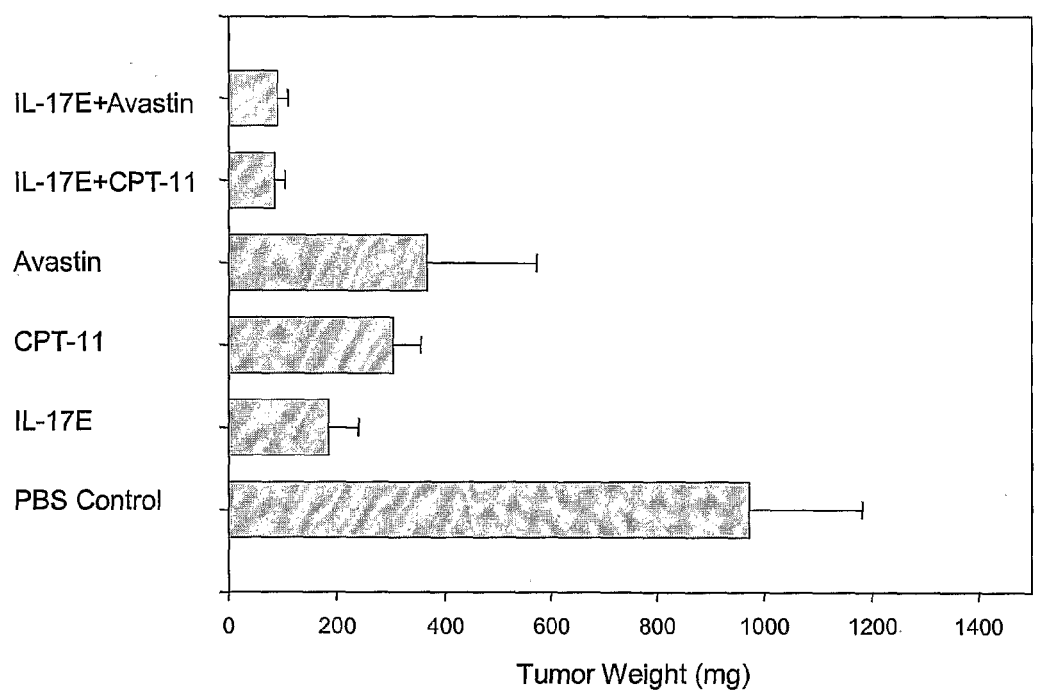

IL-17E both alone and in combination with either CPT-11 or Avastin® significantly inhibited tumour growth as compared to PBS. The combination of human IL-17E and either CPT-11 or Avastin® had a greater antitumour effect than either agent alone (FIGS. 21A and B).

Example 20

Increased Serum Interleukin 5 in Mice Treated with Interleukin 17E

The expression of IL-5 in serum was examined in tumour-engrafted mice treated with IL-17E. CD1-nude mice were engrafted with either C8161 human melanoma cells or Mia-PaCa2 pancreatic cancer cells and treated with either PBS or murine IL-17E as described previously. Serum samples were collected individually from each mouse at the endpoint of the experiment, and IL-5 levels were determined by ELISA assay (BD OptEIA; BD Biosciences), according to the manufacturer's instructions. Immunoassay plates were coated with anti-mouse IL-5 monoclonal antibody as a capture antibody and incubated with serial dilutions of mouse sera. Plates were washed three times with wash buffer and blocked for 1 hr at room temp. Plates were incubated with biotinylated anti-mouse IL-5 monoclonal antibody and avidin-horseradish peroxidase conjugate for 1 hour, followed by seven washes. Substrate solution was added for 30 minutes, followed by stop solution, prior to measurement of absorbance (450/570 nm). Statistical analysis was performed to compare IL-5 levels. P values <0.05 were considered to be significant.

Figure 22:
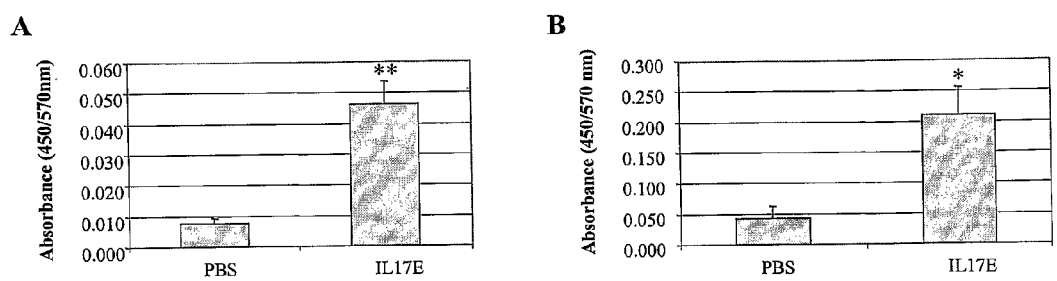
FIG. 22 depicts the effect of interleukin 17E treatment on serum IL-5 levels in (A) human melanoma C8161 and (B) human pancreatic cancer MiaPaCa2 tumour-engrafted mice.

Serum levels of IL-5 were significantly higher in mice treated with murine IL-17E as compared to PBS in mice engrafted with either human melanoma cells (FIG. 22A) or human pancreatic cancer cells (FIG. 22B).

Example 21

Effect of Interleukin 17E on Eosinophils and B Cells in Spleens of Mice Treated with Interleukin 17E The effect of interleukin 17E on increased percentage of splenic eosinophils and B cells and the proportion of activated splenic B cells was examined. CD1-nude mice engrafted with C8161 human melanoma cells were treated with either PBS, murine IL-17E, or human IL-17E as described previously. At the endpoint of the experiment, spleens were isolated from treated mice, stained with markers specific for eosinophils (CCR3+), B cells (either IgM+ or CD19+), and B cell activation (CD-80+, CD86+), and examined by flow cytometry. Flow cytometry was performed as described in Example 4 above.

The percentage of eosinophils was determined by surface staining the granulocyte-gated population with phycoerythrin (PE)-conjugated anti-mouse CCR3. The percentage of B cells in the spleen was examined by surface staining with phycoerythrin (PE)-conjugated anti-mouse CD19. The proportion of activated splenic B cells was determined by staining with FITC-conjugated anti-mouse IgM together with PE-conjugated anti-mouse CD80 and PE-conjugated anti-mouse CD86. Statistical analysis was performed to compare eosinophil and B cell numbers/activation. P values <0.01 were considered to be significant.

Figure 23:
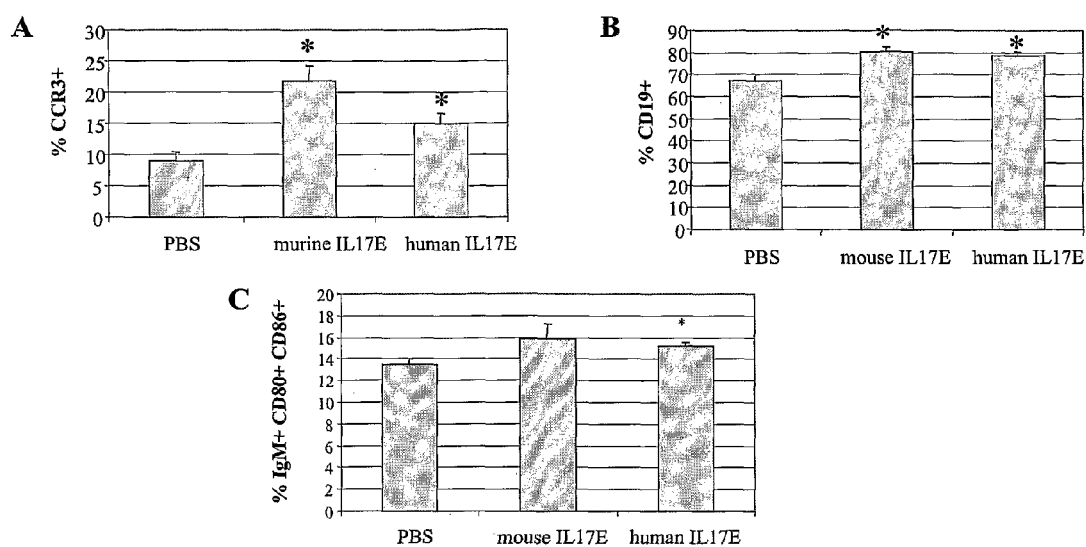
FIG. 23 depicts the effect of interleukin 17E on splenic eosinophil numbers and B-cell numbers and activation. (A) depicts percentage of splenic eosinophils; (B) depicts percentage splenic B cells and (C) proportion of activated B cells.

The percentage of splenic eosinophils (FIG. 23A) and splenic B cells (FIG. 23B) were significantly increased in mice treated with either murine or human IL-17E as compared to PBS. In addition, the proportion of activated B cells in the spleen was significantly increased in mice treated with either murine or human IL-17E as compared to PBS (FIG. 23C).

Example 22

Effect of Interleukin 17E on Numbers and Activation of B Cells in Tumour-Engrafted Mice In order to confirm that the effect of BD-BRM on splenic B cells as described in Example 5 is due to interleukin 17E activity, the effect of interleukin 17E on numbers and activation status of splenic B cells was examined. CD1-nude mice engrafted with C8161 human melanoma cells were treated with either PBS or murine IL-17E as described previously. At the endpoint of the experiment, spleens were isolated from treated mice, stained with markers specific for B cells (IgM+), and B cell activation (CD-80+, CD86+), and examined by flow cytometry. Flow cytometry was performed as described in Example 4 above.

Splenocytes were analyzed for the percentage of B cells by surface staining with FITC-conjugated anti-mouse IgM antibodies. Activated B cells were determined by surface staining with FITC-conjugated-anti-mouse IgM antibodies, and PE-conjugated-anti-mouse CD80 and PE-conjugated-anti-mouse CD86. Statistical analysis was performed to compare B cell numbers/activation. P values <0.01 were considered to be significant.

Figure 24:
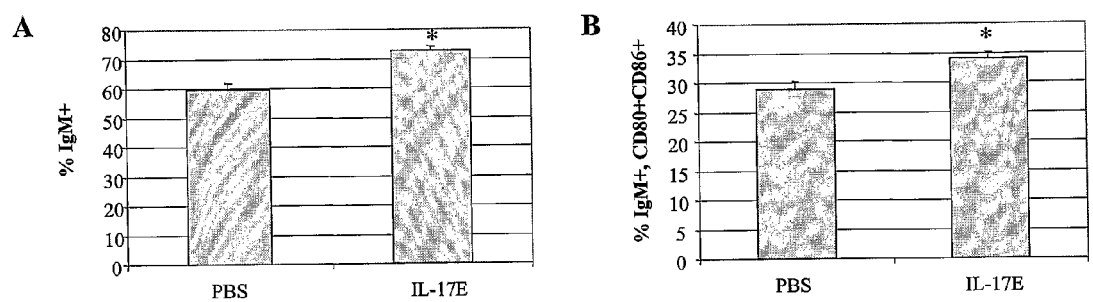
FIG. 24 depicts the effect of interleukin 17E on (A) splenic B cell numbers and (B) activation.

The percentage of splenic B cells (FIG. 24A) was significantly increased in mice treated with murine IL-17E as compared to PBS. In addition, the proportion of activated B cells in the spleen was significantly increased in mice treated with murine IL-17E as compared to PBS (FIG. 24B).

Example 23

Antitumor Efficacy of Interleukin 17E Using Different Routes of Administration The effect of different routes of administration (intraperitoneal and intravenous) on the antitumour efficacy of interleukin 17E was examined using amurine xenograft model of human melanoma. Human melanoma C8161 cells ($10^6$ cells in 100 µl PBS) were subcutaneously implanted into the right flank of CD-1 athymic nude mice. When tumours reached a volume of 50-100 mm$^3$, mice were randomly separated into four groups of 10 animals and treated as follows:

Group I: 200 ml of PBS intraperitoneally (i.p.) per mouse every day until the endpoint of the experiment;

Group II: 0.04 mg/kg of murine IL-17E intraperitoneally (i.p.) per mouse every other day until the endpoint of the experiment;

Group 200 ml of PBS intravenously (i.v.) per mouse every day until the endpoint of the experiment; and Group IV: 0.04 mg/kg of murine IL-17E intravenously (i.v.) every other day until the endpoint of the experiment.

Tumour weight was determined from tumour tissue surgically excised from the animal on the last day of the experiment.

Figure 25:
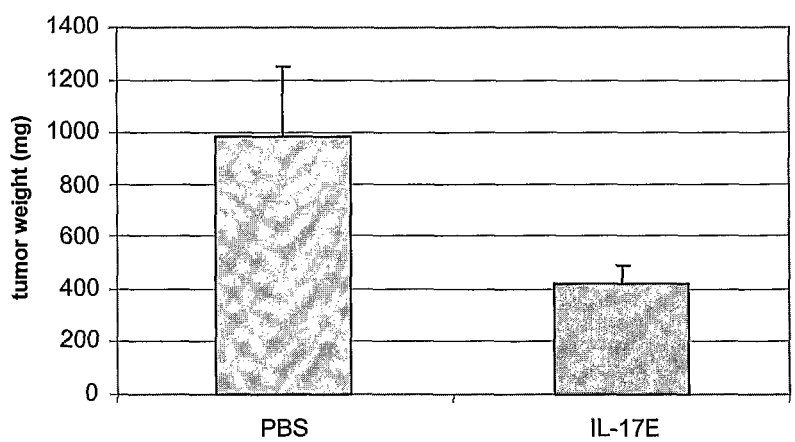
FIG. 25 depicts the antitumour effect of murine interleukin 17E when administered by either (A) intraperitoneally or (B) intravenously to CD-1 athymic nude mice bearing human melanoma (C8161) tumour xenografts.
Figure 25:
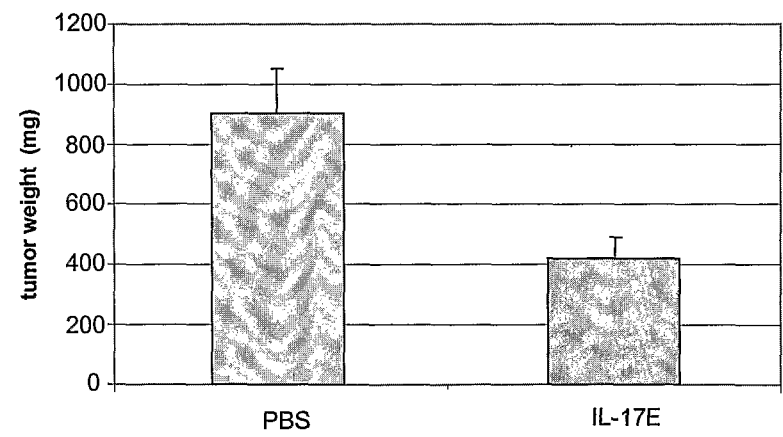

Murine IL-17E was able to inhibit tumour growth when administered either intraperitoneally or intravenously. Both routes of administration showed approximately equivalent antitumour efficacy as compared to PBS (FIGS. 25A and B).

Example 24

Binding of Human and Murine Interleukin 17E to the Murine Interleukin 17E Receptor The ability of human and murine interleukin 17E to bind to the IL-17E receptor was examined using the murine pre-B cell line 70Z/3 (Paige, C. J., et al. (1981) Nature 292:631-3). Fluorescence-Activated Cell Sorter (FACS) Analysis:

$1\times10^6$ 70Z/3 cells/sample were incubated with either murine or human IL-17E (1 µg/$10^6$ cells) for 30 minutes at 4° C. After washing twice, cells that had been incubated with murine IL-17E were incubated with biotin-conjugated goat anti-mouse IL17E and phycoerythrin (PE)-Cy5.5-conjugated streptavidin. Cells that had been incubated with human IL-17E were incubated with biotin-conjugated goat anti-human IL17E-biotin and phycoerythrin (PE)-Cy5.5-conjugated streptavidin. As negative controls, cells were stained with antibodies as described without preincubation with human or murine IL-17E. Samples were then fixed with 0.5% paraformaldehyde prior to FACS analysis.

Figure 26:
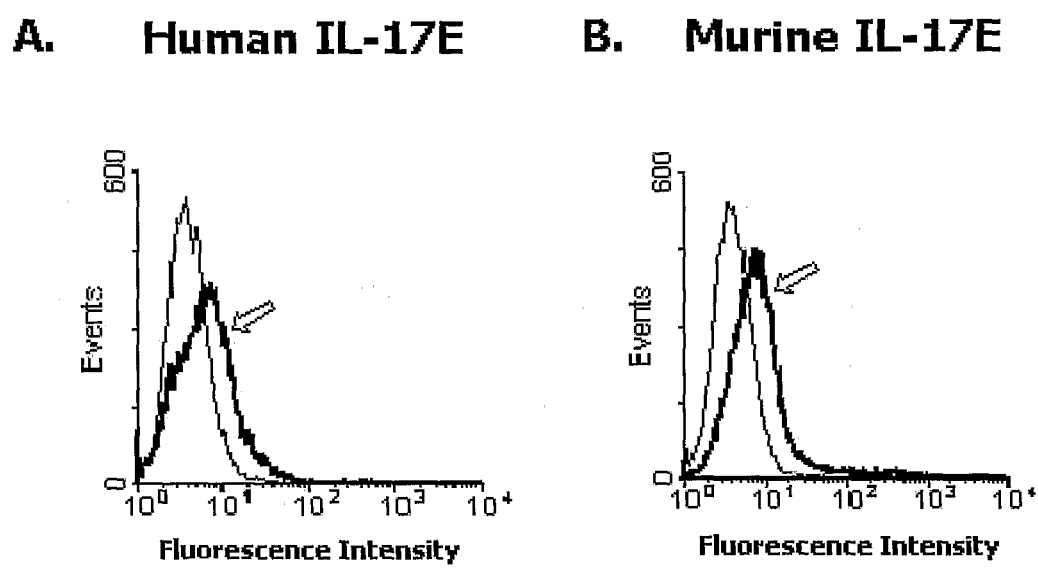
FIG. 26 depicts fluorescence-activated cell sorter (FACS) curves showing receptor binding of human interleukin 17E (A) and murine interleukin 17E (B) to murine interleukin 17E receptor in pre-B cell line 70Z/3. Arrows indicate cells that have been stained as interleukin 17E-positive. Cells stained without preincubation with interleukin 17E (negative controls) are indicated by the thin line curves.

FACS analysis revealed that both human and murine IL-17E bound to the murine IL-17E receptor present on the pre-B cell line 70Z/3, as indicated in FIG. 26.

Example 25

Effect of Immune Absorption of Interleukin 17E on Antitumour Efficacy

To further confirm that the antitumour effect demonstrated by murine and human IL-17E was due to the IL-17E polypeptide, IL-17E preparations were depleted of IL-17E in vitro using anti-IL-17E antibodies. Immunodepleted IL-17E preparations were then used to examine antitumour efficacy using a murine xenograft model of human pancreatic cancer.

IL-17E Depletion:

25 µg of murine or human IL-17E were reconstituted with 200 µl PBS. For before samples, 8 µl (1 µg) was removed from each sample. 1 µg of rat anti-murine IL17E or goat anti-human IL-17E was added to murine IL-17E or human IL17E, respectively, and samples were incubated for 2 hours gently rocking at 4° C. 50 µl of Protein A-Sepharose (1:1 slurry) was subsequently added, and further mixed for another 2 hours at 4° C. Samples were pelleted by centrifugation, and supernatants were transferred to new tubes. A second depletion of the supernatant was performed as described above using appropriate antibodies and beads for 1 hour at 4° C. with rotating. Samples were separated by electrophoresis on SDS-PAGE gels and analyzed by either Western blotting or silver staining to show a reduction in IL-17E levels in immunodepleted samples. Samples that had been through two rounds of IL-17E immuno depletion (twice-absorbed) were used in antitumor efficacy experiments.

The ability of immunodepleted interleukin 17E samples to inhibit human pancreatic cancer growth was examined as follows. Human pancreatic cancer MiaPaCa-2 cells ($10^6$ cells in 100 µl PBS) were subcutaneously implanted into the right flank of CD-1 athymic nude mice. When tumours reached a volume of 50-100 mm$^3$, mice were randomly separated into six groups of 10 animals and treated as follows:

Group I: 200 µl of PBS intraperitoneally (i.p.) per mouse every day until the endpoint of the experiment;
Group II: 200 µl of twice-absorbed PBS (PBS-D) intraperitoneally (i.p.) per mouse every day until the endpoint of the experiment;
Group III: 0.04 mg/kg of murine IL-17E intraperitoneally (i.p.) every other day until the endpoint of the experiment;
Group IV: 0.04 mg/kg of twice-absorbed murine IL-17E (mIL-17E-D) intraperitoneally (i.p.) every other day until the endpoint of the experiment;
Group V: 0.04 mg/kg of human IL-17E intraperitoneally (i.p.) every other day until the endpoint of the experiment; and
Group VI: 0.04 mg/kg of twice-absorbed human IL-17E (hIL-17E-D) intraperitoneally (i.p.) every other day until the endpoint of the experiment.

The size of the tumours was measured by caliper measurements throughout the experiment. Tumour weight was determined from tumour tissue surgically excised from the animal on the last day of the experiment. T-tests were performed to assess the statistical significance of differences in tumour sizes. A p value of $\leq 0.05$ was considered to be statistically significant.

Figure 27A:
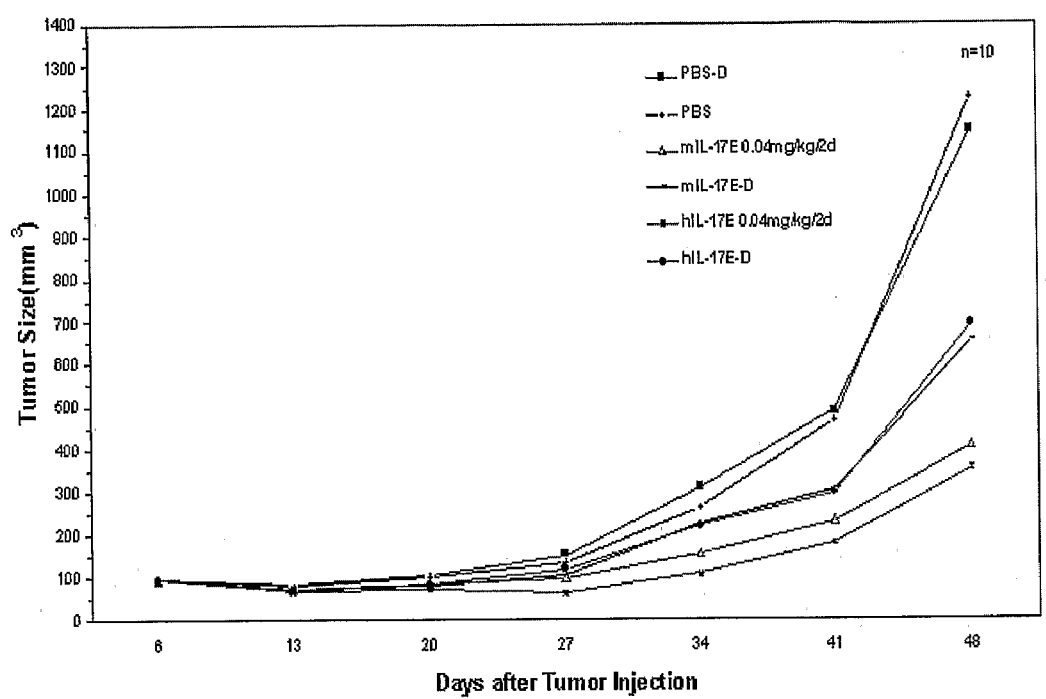
FIG. 27 depicts the antitumour effect of immunodepleted murine and human interleukin 17E samples on (A) tumour volume and (B) tumour weight in CD-1 athymic mice bearing human pancreatic cancer MiaPaCa2 xenografts.
Figure 27B:
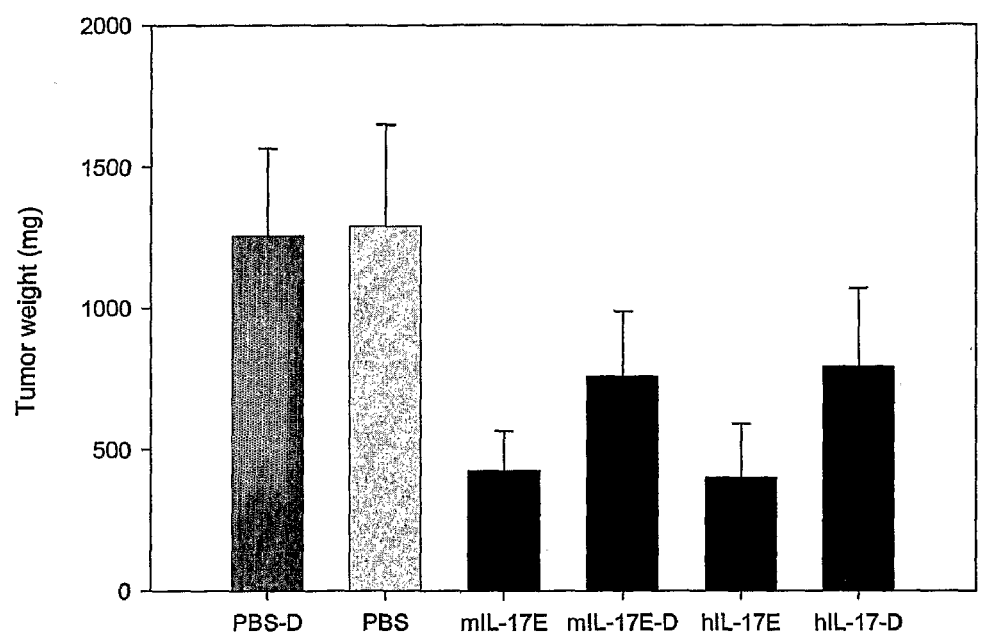

Immunodepleted murine and human IL-17E samples demonstrated reduced antitumor efficacy compared to non-immunodepleted samples (FIGS. 27A and B). The size of tumours from mice treated with non-immunodepleted IL-17E was significantly different than those from mice treated with PBS. By comparison, the size of tumours from mice treated with immunodepleted IL-17E samples were not significantly different than those from mice treated with PBS.

Example 26

Ability of Interleukin 17E to Activate Signaling Pathways in a B Cell Lymphoma Model The effect of IL-17E on activation of signaling pathways in B cells was examined using the B cell lymphoma cell line WEHI-231 (Lanier L. L., et al. (1981) *J. Immunol.* 126:626-31). Specifically, the activation status of the protein tyrosine kinase Lyn and the B cell linker protein BLNK (Tsubata, T., et al., (2001) *Int Rev Immunol* 20:675-8) were examined. An increased level of the phosphorylated forms of these proteins is indicative of activation.

A total of $1.5 \times 10^6$ cells per sample were stimulated in vitro with 0.21 µg of either human IL-17E or murine IL17E at 37° C. Cells were lysed at time points t=0, 2, and 5 minutes in lysis buffer for 30 minutes on ice, followed by centrifugation for 10 minutes. Samples containing approximately 25 µg of protein were separated by SDS-PAGE, followed by transfer to membranes for Western blotting.

For detection of phosphorylated BLNK, Western blots were incubated with rabbit anti-phospho-BLNK antibodies, followed by horseradish peroxidase (HRP)-conjugated anti-rabbit antibodies.

For detection of Lyn, Western blots were incubated with rabbit anti-Lyn antibodies, followed by horseradish peroxidase (HRP)-conjugated anti-rabbit antibodies. All blots were exposed to autoradiography film and developed to detect proteins of interest by chemiluminescence.

To assess equivalence in protein loading among lanes in both experiments, blots were stripped of antibodies and incubated with mouse anti-GAPDH antibodies and HRP-conjugated anti-mouse antibodies, followed by chemiluminescence-based detection.

Figure 28:
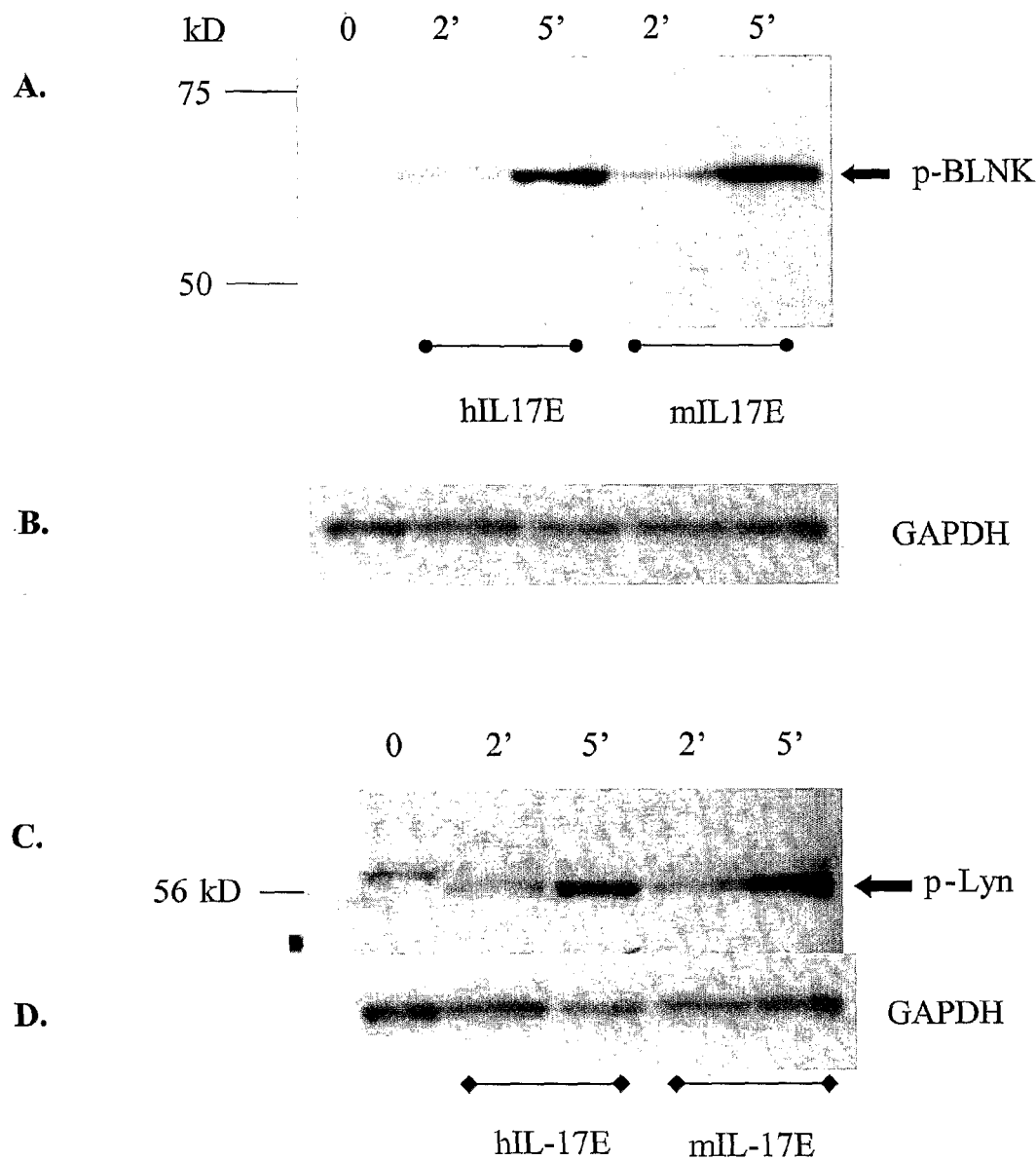
FIG. 28A depicts a Western blot showing induction of BLNK phosphorylation in B cell lymphoma cell line WEHI-231 following in vitro exposure to either human interleukin 17E (hIL-17E) or murine interleukin 17E (mIL-17E). Times of exposure (0, 2, 5 minutes) are indicated. Arrow indicates phosphorylated BLNK (p-BLNK). Molecular weight markers in kilodaltons (kD) are shown. Levels of GAPDH are shown to indicate equivalent loading among lanes (FIG. 28B).
FIG. 28C depicts a Western blot showing induction of Lyn phosphorylation in B cell lymphoma cell line WEHI-231 following in vitro exposure to either human interleukin 17E (hIL-17E) or murine interleukin 17E (mIL-17E). Times of exposure (0, 2, 5 minutes) are indicated. Arrow indicates phosphorylated Lyn (p-Lyn) at the expected molecular weight of approximately 56 kD. Levels of GAPDH are shown to indicate equivalent loading among lanes (FIG. 28D).

Results: Levels of both phosphorylated BLNK protein and phosphorylated Lyn protein were increased in WEHI-231 cells following incubation with either human or murine IL-17E, as indicated by arrows in the figures (FIGS. 28A and C). Levels of the phosphorylated forms of both proteins increased over the time course. Equivalent loading of protein among lanes is demonstrated in FIGS. 28B and D.

Example 27

Ability of Interleukin 17E to Promote Interaction of Interleukin 17E Receptor with Protein Tyrosine Kinase Lyn in a B Cell Lymphoma Model The effect of interleukin 17E on the induction of interaction of its receptor IL17BR with the protein tyrosine kinase Lyn was examined using the B cell lymphoma cell line WEHI-231.

A total of $5 \times 10^6$ cells per sample were incubated with 0.1 µg of human IL17E (hIL-17E) for 5 minutes at 37° C. Cells were lysed in lysis buffer for 30 minutes on ice, followed by centrifugation for 10 minutes. The tyrosine kinase Lyn was immunoprecipitated from 350 µg of protein lysate using rabbit anti-Lyn antibodies coupled to Protein A Sepharose beads. Immunoprecipitated samples containing approximately 25 µg of protein were separated by SDS-PAGE, followed by transfer to membranes for Western blotting.

For detection of phosphorylated Lyn, blots were incubated with anti-phosphotyrosine antibodies, followed by horseradish peroxidase (HRP)-conjugated anti-mouse antibodies.

For detection of IL17BR, blots were incubated with biotin-conjugated-rat anti-IL17BR antibodies, followed by HRP-conjugated streptavidin.

To assess equivalent loading of Lyn, blots were incubated with rabbit anti-Lyn antibodies, followed by HRP-conjugated-anti-rabbit antibodies.

All blots were exposed to autoradiography film and developed to detect chemiluminescence.

Figure 29:
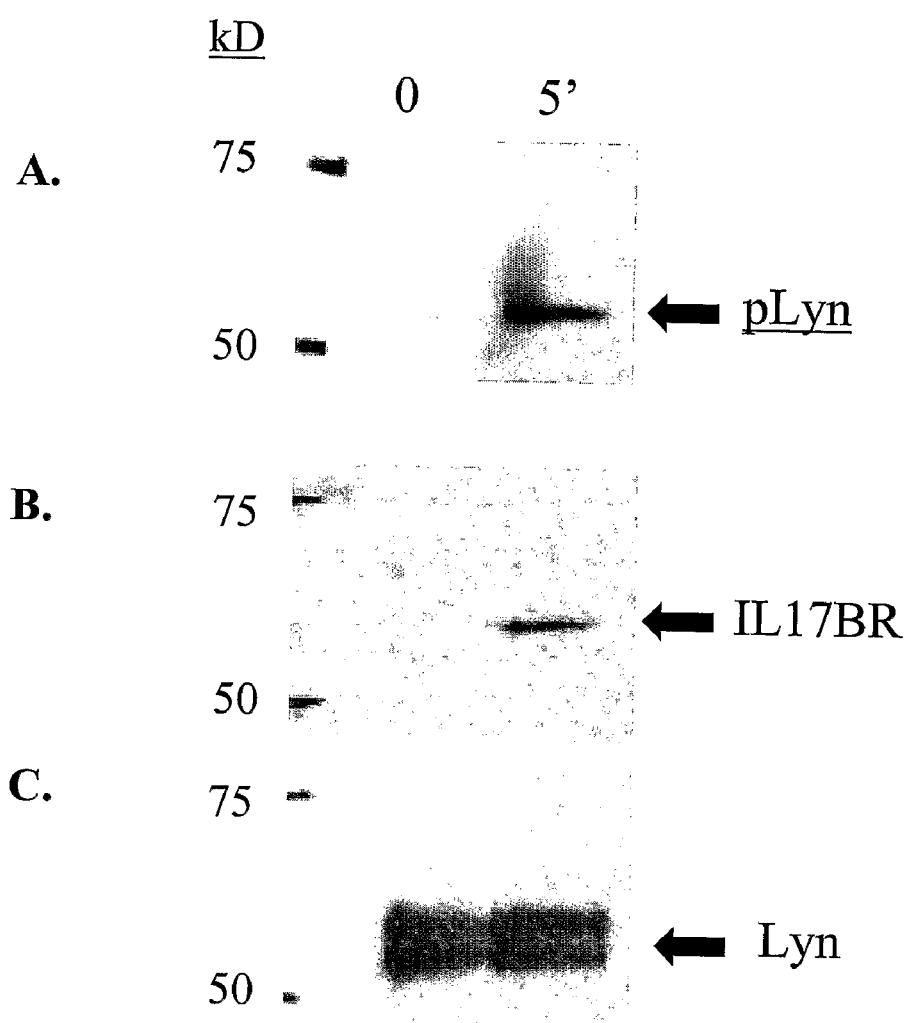
FIG. 29 depicts coimmunoprecipitation of Lyn and IL17BR in B cell lymphoma cell line WEHI 231 following exposure to human interleukin 17E. Times of exposure (0 and 5 minutes) are indicated. Arrows indicate phosphorylated Lyn (p-Lyn.

Results: Lyn and IL17BR were coimmunoprecipitated from WEHI-231 cells following exposure of cells to human IL-17E, indicating that these proteins interact in response to IL-17E (FIGS. 29A and B). Equivalent loading of Lyn protein among lanes is demonstrated in FIG. 29C.

Example 28

Ability of Interleukin 17E to Activate the NF-kappaB Pathway

The ability of both human and murine interleukin 17E to activate proteins in the Nuclear Factor-kappa B (NF-kappaB) pathway was examined using the B cell lymphoma cell line WEHI-231. Murine IL-17E has previously been shown to activate the NF-kappa B pathway (Lee, J., et al., (2001) J Biol Chem 276:1660-4). Activation of the NK-kappaB pathway was assessed by increased phosphorylation of the protein IkappaB alpha. Non-phosphorylated Ikb alpha is complexed with NF-kappaB in the cell cytoplasm in an inactive state in non-stimulated cells. The activation of NF-kappa B is associated with the phosphorylation of IkappaB alpha in response to certain stimuli.

A total $5\times10^6$ cells per sample were stimulated with 0.7 µg of either human IL-17E (hIL-17E) or murine IL-17E (mIL-17E) at 37° C. Cells were lysed at time points t=0, 2, and 5 minutes in lysis buffer for 30 minutes on ice, followed by centrifugation for 10 minutes. Samples containing approximately 40 µg of protein were separated by SDS-PAGE, followed by transfer to membranes for Western blotting.

Blots were incubated with rabbit anti-phospho-IkappaB-alpha antibodies, followed by horesradish peroxidase (HRP)-conjugated anti-rabbit antibodies. Blots were exposed to autoradiography film and developed to detect phosphorylated IkB (at approximately 41 kD) by chemiluminescence.

To assess equivalence in protein loading among lanes in both experiments, blots were stripped of antibodies and incubated with mouse anti-GAPDH antibodies and HRP-conjugated anti-mouse antibodies, followed by chemiluminescence-based detection.

Figure 30:
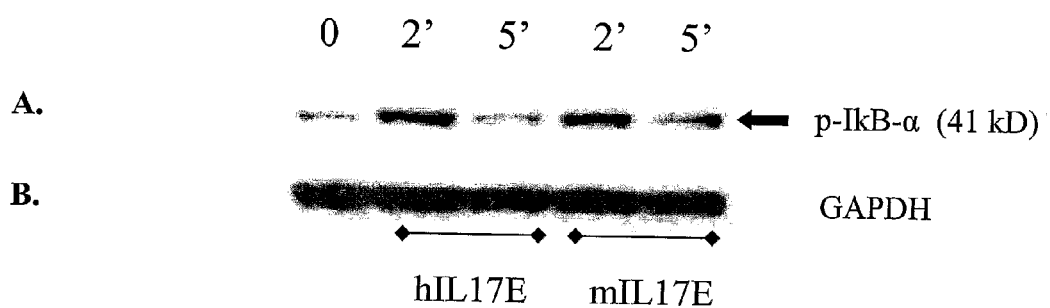
FIG. 30A depicts increased levels of phosphorylated IkappaB (p-IkB; indicated by arrow) in B cell lymphoma cell line WEHI 231 following exposure to either human interleukin 17E or murine interleukin 17E. Times of exposure (0, 2, 5 minutes) are indicated. Levels of GAPDH are shown to indicate equivalent loading among lanes (FIG. 30B).

Results: Levels of phosphorylated IkappaB alpha (p-IkB-α) were increased in WEHI-231 cells following incubation with either human or murine IL-17E, as indicated in FIG. 30A. Equivalent loading of GAPDH among lanes is shown (FIG. 30B).

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A method of treating a tumour in a subject in need thereof comprising administering an effective amount of an interleukin 17E (IL-17E) polypeptide to said subject.

2. The method according to claim 1, wherein said tumour is a tumour associated with a mucosal tissue.

3. The method according to claim 1, wherein said tumour is a colon tumour, breast tumour, ovarian tumour, cervical tumour, endometrial tumour, lung tumour, gastric tumour, oral tumour, oesophageal tumour, or prostate tumour.

4. The method according to claim 1, wherein said tumour is a solid tumour.

5. The method according to claim 4, wherein said tumour is a melanoma, a pancreatic tumour, an ovarian tumour, a lung tumour, a breast tumour or a colon tumour.

6. The method according to claim 4, wherein said tumour is a pancreatic tumour.

7. The method according to claim 1, wherein said IL-17E polypeptide has the amino acid sequence of the mature polypeptide as set forth in SEQ ID NO:1, SEQ ID NO:2 or SEQ ID NO:3.

8. The method according to claim 1, wherein said IL-17E polypeptide has an amino acid sequence as set forth in SEQ ID NO:1, from amino acid 33 to 177.

9. The method according to claim 1, wherein said IL-17E polypeptide is the mature form of human IL-17E.

10. A method of treating a tumour in a subject in need thereof comprising administering an effective amount of an interleukin 17E (IL-17E) polypeptide in combination with an effective amount of one or more anti-cancer therapeutics to said subject.

11. The method according to claim 10, wherein said tumour is a tumour associated with a mucosal tissue.

12. The method according to claim 10, wherein said tumour is a colon tumour, breast tumour, ovarian tumour, cervical tumour, endometrial tumour, lung tumour, gastric tumour, oral tumour, oesophageal tumour, or prostate tumour.

13. The method according to claim 10, wherein said tumour is a solid tumour.

14. The method according to claim 13, wherein said tumour is a melanoma, a pancreatic tumour, an ovarian tumour, a lung tumour, a breast tumour or a colon tumour.

15. The method according to claim 13, wherein said tumour is a pancreatic tumour.

16. The method according to claim 10, wherein said IL-17E polypeptide has the amino acid sequence of the mature polypeptide as set forth in SEQ ID NO:1, SEQ ID NO:2 or SEQ ID NO:3.

17. The method according to claim 10, wherein said IL-17E polypeptide has an amino acid sequence as set forth in SEQ ID NO:1, from amino acid 33 to 177.

18. The method according to claim 10, wherein said IL-17E polypeptide is the mature form of human IL-17E.

19. The method according to claim 10, wherein said one or more anticancer therapeutics is one or more chemotherapeutic drugs, one or more immunotherapeutics, or a combination thereof.

20. The method according to claim 10, wherein at least one of said anticancer therapeutics is a chemotherapeutic.

21. The method according to claim 20, wherein said chemotherapeutic is a broad spectrum chemotherapeutic.

22. The method according to claim 10, wherein at least one of said anticancer therapeutics is an immunotherapeutic.

23. The method according to claim 22, wherein said immunotherapeutic is a monoclonal antibody.

24. The method according to claim 10, wherein at least one of said anticancer therapeutics is dacarbazine, cisplatin, docetaxel, erlotinib, paclitaxel, gemcitabine, CPT-11 or bevacizumab.

25. The method according to claim 10, wherein said one or more anticancer therapeutics is gemcitabine.

26. The method according to claim 10, wherein said tumour is a melanoma, and said one or more anticancer therapeutics is dacarbazine.

27. The method according to claim 10, wherein said tumour is a pancreatic tumour, and said one or more anticancer therapeutics is gemcitabine.

28. The method according to claim 10, wherein said tumour is an ovarian tumour, and said one or more anticancer therapeutics is cisplatin.

29. The method according to claim 10, wherein said tumour is a lung tumour, and said one or more anticancer therapeutics is docetaxel or erlotinib.

30. The method according to claim 10, wherein said tumour is a breast tumour, and said one or more anticancer therapeutics is cisplatin or paclitaxel.

31. The method according to claim 10, wherein said tumour is a colon tumour, and said one or more anticancer therapeutics is CPT-11 or bevacizumab.

\* \* \* \* \*

```
SEQUENCE LISTING

<160> NUMBER OF SEQ ID NOS: 12

<210> SEQ ID NO 1
<211> LENGTH: 177
<212> TYPE: PRT
<213> ORGANISM: Homo sapiens

<400> SEQUENCE: 1

Met Arg Glu Arg Pro Arg Leu Gly Glu Asp Ser Ser Leu Ile Ser Leu
 1               5                  10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser
        35                  40                  45

Glu Glu Leu Leu Arg Trp Ser Thr Val Pro Val Pro Pro Leu Glu Pro
    50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
        115                 120                 125

Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly
```

<210> SEQ ID NO 2
<211> LENGTH: 161
<212> TYPE: PRT
<213> ORGANISM: Homo sapiens

<400> SEQUENCE: 2

```
Met Tyr Gln Val Val Ala Phe Leu Ala Met Val Met Gly Thr His Thr
 1               5                  10                  15

Tyr Ser His Trp Pro Ser Cys Cys Pro Ser Lys Gly Gln Asp Thr Ser
             20                  25                  30

Glu Glu Leu Leu Arg Trp Ser Thr Val Pro Val Pro Pro Leu Glu Pro
         35                  40                  45

Ala Arg Pro Asn Arg His Pro Glu Ser Cys Arg Ala Ser Glu Asp Gly
     50                  55                  60

Pro Leu Asn Ser Arg Ala Ile Ser Pro Trp Arg Tyr Glu Leu Asp Arg
 65                  70                  75                  80

Asp Leu Asn Arg Leu Pro Gln Asp Leu Tyr His Ala Arg Cys Leu Cys
                 85                  90                  95

Pro His Cys Val Ser Leu Gln Thr Gly Ser His Met Asp Pro Arg Gly
            100                 105                 110

Asn Ser Glu Leu Leu Tyr His Asn Gln Thr Val Phe Tyr Arg Arg Pro
        115                 120                 125

Cys His Gly Glu Lys Gly Thr His Lys Gly Tyr Cys Leu Glu Arg Arg
    130                 135                 140

Leu Tyr Arg Val Ser Leu Ala Cys Val Cys Val Arg Pro Arg Val Met
145                 150                 155                 160

Gly
```

<210> SEQ ID NO 3
<211> LENGTH: 161
<212> TYPE: PRT
<213> ORGANISM: Homo sapiens

<400> SEQUENCE: 3

```
Met Tyr Gln Val Val Ala Phe Leu Ala Met Val Met Gly Thr His Thr
 1               5                  10                  15

Tyr Ser His Trp Pro Ser Cys Cys Pro Ser Lys Gly Gln Asp Thr Ser
             20                  25                  30

Glu Glu Leu Leu Arg Trp Ser Thr Val Pro Val Pro Pro Leu Glu Pro
         35                  40                  45

Ala Arg Pro Asn Arg His Pro Glu Ser Cys Arg Ala Ser Glu Asp Gly
     50                  55                  60

Pro Leu Asn Ser Arg Ala Ile Ser Pro Trp Arg Tyr Glu Leu Asp Arg
 65                  70                  75                  80

Asp Leu Asn Arg Leu Pro Gln Asp Leu Tyr His Ala Arg Cys Leu Cys
                 85                  90                  95

Pro His Cys Val Ser Leu Gln Thr Gly Ser His Met Asp Pro Arg Gly
            100                 105                 110

Asn Ser Glu Leu Leu Tyr His Asn Gln Thr Val Phe Tyr Arg Arg Pro
        115                 120                 125

Cys His Gly Glu Lys Gly Thr His Lys Gly Tyr Cys Leu Glu Arg Arg
    130                 135                 140

Leu Tyr Arg Val Ser Leu Ala Cys Val Cys Val Arg Pro Arg Val Met
145                 150                 155                 160

Ala
```

<210> SEQ ID NO 4
<211> LENGTH: 1335
<212> TYPE: DNA
<213> ORGANISM: Homo sapiens

<400> SEQUENCE: 4

```
ggcttgctga aaataaaatc aggactccta acctgctcca gtcagcctgc ttccacgagg      60
cctgtcagtc agtgcccgac ttgtgactga gtgtgcagtg cccagcatgt accaggtcag     120
tgcagagggc tgcctgaggg ctgtgctgag agggagagga gcagagatgc tgctgagggt     180
ggagggaggc caagctgcca ggtttggggc tgggggccaa gtggagtgag aaactgggat     240
cccaggggga gggtgcagat gagggagcga cccagattag gtgaggacag ttctctcatt     300
agccttttcc tacaggtggt tgcattcttg gcaatggtca tgggaaccca cacctacagc     360
cactggccca gctgctgccc cagcaaaggg caggacacct ctgaggagct gctgaggtgg     420
agcactgtgc ctgtgcctcc cctagagcct gctaggccca accgccaccc agagtcctgt     480
agggccagtg aagatggacc cctcaacagc agggccatct cccctggag atatgagttg      540
gacagagact tgaaccggct cccccaggac ctgtaccacg cccgttgcct gtgcccgcac     600
tgcgtcagcc tacagacagg ctcccacatg accccgggg caactcgga gctgctctac      660
cacaaccaga ctgtcttcta caggcggcca tgccatggcg agaagggcac ccacaagggc     720
tactgcctgg agcgcaggct gtaccgtgtt tccttagctt gtgtgtgtgt gcggccccgt     780
gtgatgggct agccggacct gctggaggct ggtcccttt tgggaaacct ggagccaggt      840
gtacaaccac ttgccatgaa gggccaggat gcccagatgc ttggcccctg tgaagtgctg     900
tctggagcag caggatcccg ggacaggatg ggggctttg gggaaaacct gcacttctgc     960
acattttgaa aagagcagct gctgcttagg gccgccggaa gctggtgtcc tgtcattttc    1020
tctcaggaaa ggttttcaaa gttctgccca tttctggagg ccaccactcc tgtctcttcc    1080
tcttttccca tccccctgcta ccctggccca gcacaggcac tttctagata tttccccctt    1140
gctggagaag aaagagcccc tggttttatt tgtttgttta ctcatcactc agtgagcatc    1200
tactttgggt gcattctagt gtagttacta gtcttttgac atggatgatt ctgaggagga    1260
agctgttatt gaatgtatag agatttatcc aaataaatat ctttatttaa aaatgaaaaa    1320
aaaaaaaaaa aaaaa                                                    1335
```

<210> SEQ ID NO 5
<211> LENGTH: 644
<212> TYPE: DNA
<213> ORGANISM: Homo sapiens

<400> SEQUENCE: 5

```
ctcaagtcac tccctaaaaa gacagtggaa ataaatttga ataaacaaaa caggcttgct      60
gaaaataaaa tcaggactcc taacctgctc cagtcagcct gcttccacga ggcctgtcag     120
tcagtgcccc acttgtgact gagtgtgcag tgcccagcat gtaccaggtg gttgcattct     180
tggcaatggt catgggaacc cacacctaca gccactggcc cagctgctgc cccagcaaag     240
ggcaggacac ctctgaggag ctgctgaggt ggagcactgt gcctgtgcct ccctagagc      300
ctgctaggcc caaccgccac ccagagtcct gtagggccat gaagatgga cccctcaaca     360
gcagggccat ctcccctgg agatatgagt tggacagaga cttgaaccgg ctcccccagg     420
acctgtacca cgcccgttgc ctgtgccgc actgcgtcag cctacagaca ggctcccaca     480
tggaccccg gggcaactcg gagctgctct accacaacca gactgtcttc taccggcggc     540
```

```
catgccatgg cgagaagggc acccacaagg gctactgcct ggagcgcagg ctgtaccgtg      600
tttccttagc ttgtgtgtgt gtgcggcccc gtgtgatggg ctag                      644

<210> SEQ ID NO 6
<211> LENGTH: 486
<212> TYPE: DNA
<213> ORGANISM: Homo sapiens

<400> SEQUENCE: 6
atgtaccagg tggttgcatt cttggcaatg tcatgggaa cccacaccta cagccactgg       60
cccagctgct gccccagcaa agggcaggac acctctgagg agctgctgag gtggagcact     120
gtgcctgtgc ctcccctaga gcctgctagg cccaaccgcc acccagagtc ctgtagggcc     180
agtgaagatg gaccctcaa cagcagggcc atctccccct ggagatatga gttggacaga     240
gacttgaacc ggctccccca ggacctgtac cacgcccgtt gcctgtgccc gcactgcgtc     300
agcctacaga caggctccca catggacccc cggggcaact cggagctgct ctaccacaac     360
cagactgtct tctaccggcg gccatgccat ggcgagaagg gcacccacaa gggctactgc     420
ctggagcgca ggctgtaccg tgtttccttg gcttgtgtgt gtgtgcggcc ccgggtcatg     480
gcttag                                                                486

<210> SEQ ID NO 7
<211> LENGTH: 169
<212> TYPE: PRT
<213> ORGANISM: Mus musculus

<400> SEQUENCE: 7

Met Tyr Gln Ala Val Ala Phe Leu Ala Met Ile Val Gly Thr His Thr
 1               5                  10                  15

Val Ser Leu Arg Ile Gln Glu Gly Cys Ser His Leu Pro Ser Cys Cys
            20                  25                  30

Pro Ser Lys Glu Gln Glu Pro Glu Glu Trp Leu Lys Trp Ser Ser
        35                  40                  45

Ala Ser Val Ser Pro Pro Glu Pro Leu Ser His Thr His His Ala Glu
    50                  55                  60

Ser Cys Arg Ala Ser Lys Asp Gly Pro Leu Asn Ser Arg Ala Ile Ser
65                  70                  75                  80

Pro Trp Ser Tyr Glu Leu Asp Arg Asp Leu Asn Arg Val Pro Gln Asp
                85                  90                  95

Leu Tyr His Ala Arg Cys Leu Cys Pro His Cys Val Ser Leu Gln Thr
            100                 105                 110

Gly Ser His Met Asp Pro Leu Gly Asn Ser Val Pro Leu Tyr His Asn
        115                 120                 125

Gln Thr Val Phe Tyr Arg Arg Pro Cys His Gly Glu Glu Gly Thr His
    130                 135                 140

Arg Arg Tyr Cys Leu Glu Arg Arg Leu Tyr Arg Val Ser Leu Ala Cys
145                 150                 155                 160

Val Cys Val Arg Pro Arg Val Met Ala
                165

<210> SEQ ID NO 8
<211> LENGTH: 985
<212> TYPE: DNA
<213> ORGANISM: Mus musculus

<400> SEQUENCE: 8
```

```
atgtaccagg ctgttgcatt cttggcaatg atcgtgggaa cccacaccgt cagcttgcgg      60
atccaggagg gctgcagtca cttgcccagc tgctgcccca gcaaagagca agaaccccg       120 gaggagtggc tgaagtggag ctctgcatct gtgtccccc  cagagcctct gagccacacc      180
caccacgcag aatcctgcag ggccagcaag gatggccccc tcaacagcag ggccatctct      240
ccttggagct atgagttgga cagggacttg aatcgggtcc cccaggacct gtaccacgct      300
cgatgcctgt gcccacactg cgtcagccta cagacaggct cccacatgga cccgctgggc      360
aactccgtcc cactttacca caaccagacg gtcttctacc ggcggccatg ccatggtgag      420
gaaggtaccc atcgccgcta ctgcttggag cgcaggctct accgagtctc cttggcttgt      480
gtgtgtgtgc ggccccgggt catggcttag tcatgctcac cacctgcctg aggctgatgc      540
ccggttggga gagagggcca ggtgtacaat caccttgcca atgcgggccg ggttcaagcc      600
ctccaaagcc ctacctgaag cagcaggctc ccgggacaag atggaggact tggggagaaa      660
ctctgacttt tgcacttttt ggaagcactt tgggaagga gcaggttccg cttgtgctgc       720
tagaggatgc tgttgtggca tttctactca ggaacggact ccaaaggcct gctgaccctg      780
gaagccatac tcctggctcc tttccctga  atcccccaac tcctggcaca ggcactttct      840
ccacctctcc ccctttgcct tttgttgtgt ttgtttgtgc atgccaactc tgcgtgcagc      900
caggtgtaat tgccttgaag gatggttctg aggtgaaagc tgttatcgaa agtgaagaga      960
tttatccaaa taaacatctg tgttt                                            985
```

```
<210> SEQ ID NO 9
<211> LENGTH: 24
<212> TYPE: DNA
<213> ORGANISM: Artificial Sequence
<220> FEATURE:
<223> OTHER INFORMATION: b-actin forward primer

<400> SEQUENCE: 9
tggctgagga ctttgtacat tgtt                                             24

<210> SEQ ID NO 10
<211> LENGTH: 26
<212> TYPE: DNA
<213> ORGANISM: Artificial Sequence
<220> FEATURE:
<223> OTHER INFORMATION: b-actin reverse primer

<400> SEQUENCE: 10
gggacttcct gtaaccactt atttca                                           26

<210> SEQ ID NO 11
<211> LENGTH: 18
<212> TYPE: DNA
<213> ORGANISM: Artificial Sequence
<220> FEATURE:
<223> OTHER INFORMATION: IL-17E forward primer

<400> SEQUENCE: 11
tgctgcccca gcaaagag                                                    18

<210> SEQ ID NO 12
<211> LENGTH: 23
<212> TYPE: DNA
```

```
<213> ORGANISM: Artificial Sequence
<220> FEATURE:
<223> OTHER INFORMATION: IL-17E reverse primer

<400> SEQUENCE: 12
gacacagatg cagagctcca ctt                                              23
```